United States Patent
Borgions et al.

(10) Patent No.: US 11,591,388 B2
(45) Date of Patent: Feb. 28, 2023

(54) PHARMACEUTICAL FORMULATIONS OF FCRN INHIBITORS SUITABLE FOR SUBCUTANEOUS ADMINISTRATION

(71) Applicant: argenx BV, Ghent (BE)

(72) Inventors: Filip Borgions, Herk-de-Stad (BE); Stephanie Lemoult, Copenhagen (DK); Kris Meerschaert, Ghent (BE)

(73) Assignee: argenx BV, Ghent (BE)

( * ) Notice: Subject to any disclaimer, the term of this patent is extended or adjusted under 35 U.S.C. 154(b) by 335 days.

(21) Appl. No.: 16/893,863

(22) Filed: Jun. 5, 2020

(65) Prior Publication Data
US 2020/0399363 A1     Dec. 24, 2020

Related U.S. Application Data

(60) Provisional application No. 62/858,806, filed on Jun. 7, 2019.

(51) Int. Cl.
*C07K 16/24* (2006.01)
*A61K 9/00* (2006.01)
(Continued)

(52) U.S. Cl.
CPC .......... *C07K 16/247* (2013.01); *A61K 9/0019* (2013.01); *A61K 39/39591* (2013.01);
(Continued)

(58) Field of Classification Search
None
See application file for complete search history.

(56) References Cited

U.S. PATENT DOCUMENTS

| 5,326,856 A | 7/1994 | Coughlin et al. |
| 5,624,821 A | 4/1997 | Winter et al. |

(Continued)

FOREIGN PATENT DOCUMENTS

| EP | 0227110 A2 | 7/1987 |
| EP | 0904107 B1 | 3/1999 |

(Continued)

OTHER PUBLICATIONS

"Auxiliary Request 1—Annotated Version" for European Patent No. 3087095 (Application No. 14827372.5), dated Oct. 28, 2020, 5 pages.

(Continued)

*Primary Examiner* — Michelle S Horning
(74) *Attorney, Agent, or Firm* — Dechert LLP; Andrew T. Wilkins; Sharla F. Flohr

(57) ABSTRACT

Provided are various aqueous formulations of the neonatal Fc receptor (FcRn) antagonist ARGX-113, including formulations useful as pharmaceutical compositions, methods for their preparation, devices comprising the various formulations, and uses thereof. In certain embodiments the formulations are suitable and useful for administration of ARGX-113 to a human subject. In certain embodiments the formulations are suitable and useful for subcutaneous administration of ARGX-113 to a human subject. The formulations can be used in the treatment of any condition that would benefit from inhibition of FcRn-mediated antibody recycling. Such conditions can include any one or more of various antibody-mediated autoimmune diseases, including, for example and without limitation, myasthenia gravis (MG) and immune thrombocytopenia (ITP).

21 Claims, 21 Drawing Sheets

Specification includes a Sequence Listing.

X-axis: Shear rate γ [1/s]
Left Y-axis: Viscosity η [Pa·s]
Right Y-axis: Shear stress τ [Pa]

(51) Int. Cl.

| | | |
|---|---|---|
| *A61K 47/02* | (2006.01) | |
| *A61K 47/18* | (2017.01) | |
| *A61K 47/20* | (2006.01) | |
| *A61K 47/22* | (2006.01) | |
| *A61K 47/26* | (2006.01) | |
| *A61K 39/395* | (2006.01) | |
| *C07K 16/00* | (2006.01) | |
| *A61K 39/00* | (2006.01) | |

(52) U.S. Cl.
CPC ............ *A61K 47/02* (2013.01); *A61K 47/183* (2013.01); *A61K 47/20* (2013.01); *A61K 47/22* (2013.01); *A61K 47/26* (2013.01); *C07K 16/00* (2013.01); *A61K 2039/505* (2013.01); *A61K 2039/54* (2013.01); *C07K 2317/52* (2013.01); *C07K 2317/76* (2013.01)

(56) References Cited

U.S. PATENT DOCUMENTS

| | | |
|---|---|---|
| 5,648,260 A | 7/1997 | Winter et al. |
| 5,677,425 A | 10/1997 | Bodmer et al. |
| 5,869,046 A | 2/1999 | Presta et al. |
| 5,885,573 A | 3/1999 | Bluestone et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,528,624 B1 | 3/2003 | Idusogie et al. |
| 6,737,056 B1 | 5/2004 | Presta et al. |
| 6,795,661 B2 | 9/2004 | Kanesawa et al. |
| 6,821,505 B2 | 11/2004 | Ward |
| 6,992,234 B2 | 1/2006 | Roopenian et al. |
| 7,083,784 B2 | 8/2006 | Dall'Acqua et al. |
| 7,670,600 B2 | 3/2010 | Dall'Acqua et al. |
| 7,683,784 B2 | 3/2010 | Nagai et al. |
| 7,704,497 B2 | 4/2010 | Dall'Acqua et al. |
| 8,012,476 B2 | 9/2011 | Dall'Acqua et al. |
| 8,021,856 B2 | 9/2011 | Umaña et al. |
| 8,067,232 B2 | 11/2011 | Kanda |
| 8,101,186 B2 | 1/2012 | Mezo et al. |
| 8,163,881 B2 | 4/2012 | Ober et al. |
| 8,195,661 B2 | 6/2012 | Asawaree |
| 8,216,805 B2 | 7/2012 | Carter et al. |
| 8,273,351 B2 | 9/2012 | Tenhoor et al. |
| 8,323,962 B2 | 12/2012 | Dall'Acqua et al. |
| 8,475,792 B2 | 7/2013 | Dall'Acqua et al. |
| 8,680,237 B2 | 3/2014 | Strome et al. |
| 8,795,661 B2 | 8/2014 | Dall'Acqua et al. |
| 8,815,246 B2 | 8/2014 | Tenhoor et al. |
| 8,834,871 B2 | 9/2014 | Ober |
| 9,260,520 B2 | 1/2016 | Tenhoor et al. |
| 10,316,073 B2 | 6/2019 | Ulrichts |
| 2004/0002587 A1 | 1/2004 | Watkins et al. |
| 2004/0010124 A1 | 1/2004 | Johnson et al. |
| 2004/0047862 A1 | 3/2004 | Lazarus et al. |
| 2004/0265321 A1 | 12/2004 | Johnson et al. |
| 2007/0041907 A1 | 2/2007 | Ober |
| 2007/0092507 A1 | 4/2007 | Balthasar et al. |
| 2009/0252729 A1 | 10/2009 | Farrington et al. |
| 2011/0081345 A1 | 4/2011 | Moore |
| 2011/0243966 A1 | 10/2011 | Farrington et al. |
| 2012/0219551 A1 | 8/2012 | Johnson |
| 2013/0142802 A1 | 6/2013 | Chang et al. |
| 2014/0302028 A1 | 10/2014 | Zha et al. |
| 2015/0218239 A1 | 8/2015 | Ulrichts et al. |
| 2016/0264669 A1 | 9/2016 | Ulrichts et al. |

FOREIGN PATENT DOCUMENTS

| | | | |
|---|---|---|---|
| EP | 1355919 | B1 | 11/2010 |
| EP | 1896503 | B1 | 10/2014 |
| JP | 2013-507128 | A | 3/2013 |
| WO | WO 1994/029351 | A2 | 12/1994 |
| WO | WO 1996/022024 | A1 | 7/1996 |
| WO | WO 1997/034631 | A1 | 9/1997 |
| WO | WO 1999/004813 | A1 | 2/1999 |
| WO | WO 1999/058572 | A1 | 11/1999 |
| WO | WO 2000/042072 | A2 | 7/2000 |
| WO | WO 2001/058957 | A2 | 8/2001 |
| WO | WO 2002/043658 | A2 | 6/2002 |
| WO | WO 2002/060919 | A2 | 8/2002 |
| WO | WO 2004/016750 | A2 | 2/2004 |
| WO | WO 2004/029207 | A2 | 4/2004 |
| WO | WO 2004/035752 | A2 | 4/2004 |
| WO | WO 2004/063343 | A2 | 7/2004 |
| WO | WO 2004/063351 | A2 | 7/2004 |
| WO | WO 2004/099249 | A2 | 11/2004 |
| WO | WO 2005/040217 | A2 | 5/2005 |
| WO | WO 2006/118772 | A2 | 11/2006 |
| WO | WO 2006/130834 | A2 | 12/2006 |
| WO | WO 2007/098420 | A2 | 8/2007 |
| WO | WO 2009/100105 | A2 | 8/2009 |
| WO | WO 2009/131702 | A2 | 10/2009 |
| WO | WO 2010/014909 | A1 | 2/2010 |
| WO | WO 2010/106180 | A2 | 9/2010 |
| WO | WO 2011/044368 | A1 | 4/2011 |
| WO | WO 2013/000702 | A1 | 1/2013 |
| WO | WO 2013/063186 | A2 | 5/2013 |
| WO | WO 2013/074598 | A1 | 5/2013 |
| WO | WO 2013/100702 | A1 | 7/2013 |
| WO | WO 2014/008391 | A1 | 1/2014 |
| WO | WO 2014/019727 | A1 | 2/2014 |
| WO | WO 2014/204280 | A1 | 12/2014 |
| WO | WO 2015/081073 | A2 | 6/2015 |
| WO | WO 2015/100299 | A1 | 7/2015 |
| WO | WO 2016/042083 | A1 | 3/2016 |
| WO | WO 2016/123521 | A2 | 8/2016 |
| WO | WO 2016/142782 | A1 | 9/2016 |
| WO | WO 2016/180765 | A1 | 11/2016 |
| WO | WO 2016/183352 | A1 | 11/2016 |
| WO | WO 2017/012959 | A1 | 1/2017 |
| WO | WO 2018/083122 | A1 | 5/2018 |
| WO | WO 2019/110823 | A1 | 6/2019 |
| WO | WO 2019/234713 | A2 | 12/2019 |
| WO | WO 2020/236695 | A1 | 11/2020 |

OTHER PUBLICATIONS

"Auxiliary Request 1—Clean Version" for European Patent No. 3087095 (Application No. 14827372.5), dated Oct. 28, 2020, 5 pages.
"Auxiliary Request 2—Annotated Version" for European Patent No. 3087095 (Application No. 14827372.5), dated Oct. 28, 2020, 5 pages.
"Auxiliary Request 2—Clean Version" for European Patent No. 3087095 (Application No. 14827372.5), dated Oct. 28, 2020, 4 pages.
"Cover Letter to the European Patent Office" for European Patent No. 3087095 (Application No. 14827372.5), dated Oct. 28, 2020, 1 page.
"Declaration of Pieter Spuijbroek" submitted with Reply to Notice of Opposition for European Patent No. 3087095 (Application No. 14827372.5), dated Oct. 28, 2020, 5 pages.
"Main Request—Annotated Version" for European Patent No. 3087095 (Application No. 14827372.5), dated Oct. 28, 2020, 5 pages.
"Main Request—Clean Version" for European Patent No. 3087095 (Application No. 14827372.5), dated Oct. 28, 2020, 5 pages.
"Online Filing Acknowledgement for Reply to Notice of Opposition" for European Patent No. 3087095 (Application No. 14827372.5), dated Oct. 28, 2020, 2 pages.
"Proof of Employment for Inventor/Applicant Sally Ward" submitted with Reply to Notice of Opposition for European Patent No. 3087095 (Application No. 14827372.5), dated Oct. 28, 2020, 1 page.
"Reply to Notice of Opposition" for European Patent No. 3087095 (Application No. 14827372.5), dated Oct. 28, 2020, 35 pages.
"Rule 90101 of the Rules and Regulations of the Board of Regents of the University of Texas System governing intellectual property"

(56) References Cited

OTHER PUBLICATIONS dated Feb. 27, 2012, submitted with Reply to Notice of Opposition for European Patent No. 3087095 (Application No. 14827372.5), dated Oct. 28, 2020, 21 pages.

"UniProtKB—P01857 (IGHG1_Human)" submitted with Reply to Notice of Opposition for European Patent No. 3087095 (Application No. 14827372.5), dated Oct. 28, 2020, 6 pages.

Abdiche et al. (2015) "The neonatal Fc receptor (FcRn) binds independently to both sites of the IgG homodimer with identical affinity," mAbs, 7(2):331-343.

Akilesh et al. (2004) "The MHC class I-like Fc receptor promotes humorally mediated autoimmune disease," J. Clin. Invest. 113(9):1328-1333.

Alegre et al. (1994) "A Non-Activating "Humanized" Anti-CD3 Monoclonal Antibody Retains Immunosuppressive Properties In Vivo," Transplantation, 57(11):1537-1543.

Alipour-Faz et al. (2017) "A comparison between IVIG and plasma exchange as preparations before thymectomy in myasthenia gravis patients," Acta Neurol Belg, 117:245-249.

Andersen et al. (2012) "Structure-based mutagenesis reveals the albumin-binding site of the neonatal Fc receptor," Nat. Commun. 3:610. pp. 1-9.

Anonymous (2016) "argenx announces initial results from Phase 1 multiple ascending dose (MAD) study of ARGX-113 in healthy volunteers—Argenx," 1 pg.

ArGEN-X "ARGX-113," http://www.argen-x.com. Accessible on the Internet at URL: http://www.argen-x.com/en-GB/content/argx-113/22. [Last Accessed Jul. 5, 2017].

ArGEN-X (Oct. 2013) "An Emerging Antibody Force: Company Presentation," Presentation Slides.

ArGEN-X (Oct. 2013) "ARGX-113: Development Opportunity in Autoimmunity," Presentation Slides.

ArGEN-X N.V. (Apr. 24, 2014) "arGEN-X advances ARGX-113 into preclinical development for autoimmune disorders," Press Release. arGEN-X. Accessible on the Internet at URL: http://www.argen-x.com/en-GB/news-internal/argen-x-advances-argx-113-into-preclinical-devlopment-for-autoimmune-disorders/60. [Last Accessed Aug. 1, 2016].

ArGEN-X N.V. (Aug. 19, 2014) "arGEN-X announces positive preclinical results for ARGX-113," Press Release. EURONEXT. Accessible on the Internet at URL: https://www.euronext.com/nl/node/506652. [Last Accessed Aug. 1, 2016].

ArGEN-X N.V. (Jun. 20, 2014) Prospectus for Public Offering of arGEN-X N.V.

Armour et al. (1999) "Recombinant human IgG molecules lacking Fcgamma receptor I binding and monocyte triggering activities," Eur. J. Immunol. 29:2613-2624.

Balighi et al., "Comparing early and late treatments with rituximab in pemphigus vulgaris: which one is better?", Archives of Dermatological Research, Dec. 1, 2018, 311(1): 63-69.

Ballow (1991) "Mechanism of action of IVIG therapy and potential uses in autoimmune connective tissue diseases," Cancer 68:1430-1436.

Barth et al. (2011) "Comparison of IVIg and PLEX in patients with myasthenia gravis," Neurology. 76(23):2017-2023.

Blanchette et al. (1984) "Intensive plasma exchange therapy in ten patients with idiopathic thrombocytopenic purpura," Transfusion. 24(5):388-394.

Burns (2012) "Of Mice and Children: Lessons From a Kawasaki Mouse Model," Circulation. 125:1480-1481.

Burns et al. (2010) "History of outcome measures for myasthenia gravis," Muscle Nerve. 42(1):5-13.

Bussel et al., "Long-term use of the thrombopoietin-mimetic romiplostim in children with severe chronic immune thrombocytopenia (ITP) : Romiplostim in Pediatric ITP" Pediatric Blood and Cancer, Feb. 1, 2015, vol. 62, No. 2, pp. 208-213.

Bussel et al., "A Randomized, Double-Blind Study of Romiplostim to Determine its Safety and Efficacy in Children with Immune Thrombocytopenia", Blood, vol. 118, No. 1, Jul. 7, 2011, pp. 28-36.

Challa (2013) "Autoantibody depletion ameliorates disease in murine experimental autoimmune encephalomyelitis," mAbs, 5(5):655-659.

Chaudhury et al. (2003) "The major histocompatibility complex-related Fc receptor for IgG (FcRn) binds albumin and prolongs its lifespan," J. Exp. Med. 197(3):315-322.

Cipriani et al. (2009) "MET as a target for treatment of chest tumor," Lung Cancer. 63(2):169-179.

Clarkson et al. (1986) "Treatment of Refractory Immune Thrombocytopenic Purpura with an Anti-Fcgamma-Receptor Antibody," New England Journal of Medicine. 314(9):1236-1239.

ClinicalTrials.gov, "A Study to Evaluate the Safety, Efficacy, and Pharmacokinetics of ARGX-113 in Patients with ITP", ClinicalTrials.gov Identifier NCT03102593, Apr. 6, 2017, 7 pages.

ClinicalTrials.gov, "A Study to Evaluate the Safety, PD, PK and Efficacy of ARGX-113 in Patients with Pemphigus", ClinicalTrials.gov Identifier NCT03334058, Nov. 7 , 2017, 8 pages.

ClinicalTrials.gov, "A Study to Evaluate the Safety, PD, PK and Efficacy of ARGX-113 in Patients with Pemphigus", ClinicalTrials.gov Identifier NCT04598477, Oct. 22, 2020, 10 pages.

Coetzee et al. (2000) "The Effect of Monoclonal Anti-human-platelet Antibodies on Platelet Kinetics in a Baboon Model: IgG Subclass Dependency," Thromb. Haemost. 83:148-156.

Combined Search and Examination Report for Great Britain Application No. GB1617270.2, dated Aug. 3, 2017, 6 pages.

Crow et al. (2008) "The Mechanisms of Action of Intravenous Immunoglobulin and Polyclonal Anti-D Immunoglobulin in the Amelioration of Immune Thrombocytopenic Purpura: What Do We Really Know?" Transfusion Medicine Reviews. 22:103-116.

Crow et al. (2011) "The neonatal Fc receptor (FcRn) is not required for IVIg or anti-CD44 monoclonal antibody-mediated amelioration of murine immune thrombocytopenia," Blood. 118:6403-6406.

Darabi et al. (2006) "Current usage of intravenous immune globulin and the rationale behind it: the Massachusetts General Hospital data and a review of the literature," Transfusion. 46(5):741-753.

Daugherty et al., "Formulation and delivery issues for monoclonal antibody therapeutics", Adv Drug Deliv Rev., Aug. 7, 2006, 58(5-6): 686-706.

De Haard et al., "Advancing ARGX-113 and ARGX-110 to Clinical Proof of Concept", Dec. 4, 2016, pp. 1-575.

Debre et al. (1993) "Infusion of Fc gamma fragments for treatment of children with acute immune thrombocytopenic purpura," Lancet. 342(8877):945-949.

Deng et al. (2007) "Pharmacokinetic/pharmacodynamic modeling of IVIG effects in a murine model of immune thrombocytopenia," J. Pharm. Sci. 96(6):1625-1637.

Dick Jr. et al., "C-Terminal Lysine Variants in Fully Human Monoclonal Antibodies: Investigation of Test Methods and Possible Causes", Biotechnology and Bioengineering, 2008, vol. 100, No. 6, pp. 1132-1143.

Duncan et al. (1988) "Localization of the binding site for the human high-affinity Fc receptor on IgG," Nature, 332:563-564.

Eddleston et al., "Blockade of the Neonatal Fc Receptor (FcRn) Represents an Effective Mechanism for the Removal of Pathogenic Autoantibodies in Primary Immune Thrombocytopenia", Database Biosis [Online] Biosciences Information Service, Philadelphia, PA, Dec. 7, 2017, XP002794883, Database accession No. PREV201900186122 abstract & Blood, vol. 130, No. Suppl. 1, p. 230.

Edelman et al. (1969) "The covalent structure of an entire gammaG immunoglobulin molecule," The Journal of Immunology, 63:5335-5342.

El-Salem et al. (2014) "Treatment of MuSK-Associated Myasthenia Gravis," Curr. Treat. Options Neurol., 16:283, 17 pages.

Eymard et al. (2009) "[Antibodies in myasthenia gravis]," Rev. Neurol. (Paris). 165(2):137-143.

Federico et al. (2000) "Multifocal motor neuropathy improved by IVIg: randomized, double-blind, placebo-controlled study," Neurology. 55:1256-1262.

Flaherty et al. (Oct. 24, 2011) "Nonclinical evaluation of GMA161—an antihuman CD16 (FORM) monoclonal antibody for treatment of autoimmune disorders in CD16 transgenic mice," Toxicological Sciences. 125(1):299-309.

(56) References Cited

OTHER PUBLICATIONS

Frusho et al. (1984) "High-dose intravenous gammaglobulin for Kawasaki disease," Lancet. 2:1055-1058.

Gan et al. (2009) "Analyses of the recycling receptor, FcRn, in live cells reveal novel pathways for lysosomal delivery," Traffic. 10:600-614.

Garcia et al. (2001) "Kinetics and thermodynamics of T cell receptor-autoantigen interactions in murine experimental autoimmune encephalomyelitis," Proc. Natl. Acad. Sci. USA. 98:6818-6823.

Genbank Database [online] (Jul. 2, 2016) "*Homo sapiens* Fc fragment of IgG receptor IIIa (FCGR3A), transcript variant 1, mRNA," Accession No. NM_000569. Accessible on the Internet at URL: http://www.ncbi.nlm.nih.gov/nuccore/NM_000569. [Last Accessed Aug. 19, 2016].

Ghetie et al. (1996) "Abnormally short serum half lives of IgGs in beta2-microglobulin deficient mice," Eur. J. Immunol. 26:690-696.

Ghetie et al. (1997) "Increasing the serum persistence of an IgG fragment by random mutagenesis," Nature Biotech. 15:637-640.

Ghetie et al. (2002) "Transcytosis and catabolism of antibody," Immunol. Res. 25(2):97-113.

Gilhus et al. (2011) "Myasthenia Gravis: A Review of Available Treatment Approaches," Autoimmune Diseases, Article ID 847393, 6 pages.

Grau (Sep. 21, 2011) "IgG core a-fucosylation and its impacton FcγRIIIa binding," Roche Glycart AG. In; MipTec 2011, Basel, Switzerland.

Grevys et al. (Apr. 22, 2015) "Fc Engineering of Human lgG1 for Altered Binding to the Neonatal Fc Receptor Affects Fc Effector Functions," J Immunol. 194(11):5497-5508.

Guptill et al. (Aug. 11, 2016) "Effect of therapeutic plasma exchange on immunoglobulins in myasthenia gravis," Autoimmunity. 49(7):472-479.

Hansen et al. (2002) "Intravenous Immunoglobulin Mediates an Increase in Anti-Platelet Antibody Clearance via the FcRn Receptor," Thromb. Haemost. 88:898-899.

Hanson (2014) "The role of the immunoglobulin G1 Fc N-glycan in FcγRIIIa affinity," Thesis for partial fulfillment of the degree of Master of Science. Iowa State University. Paper 14135.

Howard et al. (Apr. 30, 2013) "A randomized, double-blind, placebo-controlled phase II study of eculizumab in patients with refractory generalized myasthenia gravis," Muscle Nerve. 48(1):76-84.

Howard et al., "Randomized phase 2 study of FcRn antagonist efgartigimod in generalized myasthenia gravis", Neurology, 2019, vol. 92, No. 23, pp. 1-8.

Huang et al. (2005) "The central residues of a T cell receptor sequence motif are key determinants of autoantigen recognition in murine experimental autoimmune encephalomyelitis," Eur. J. Immunol. 35:299-304.

Hutchins et al. (1995) "Improved biodistribution, tumor targeting, and reduced immunogenicity in mice with a gamma4 variant of Campath-1H," Proc. Natl. Acad. Sci., USA, 92:11980-11984.

Idusogie et al. (2000) "Mapping of the C1q Binding Site on Rituxan, a Chimeric Antibody with a Human IgG1 Fc," J. Immunol., 164:4178-4184.

Idusogie et al. (2001) "Engineered Antibodies with Increased Activity to Recruit Complement," J. Immunol., 166:2571-2575.

Imbach et al. (1981) "High-dose intravenous gammaglobulin for idiopathic thrombocytopenic purpura in childhood," The Lancet, 1228-1231.

Imbach et al. (1985) "Intravenous immunoglobulin versus oral corticosteroids in acute immune thrombocytopenic purpura in childhood," The Lancet, 464-468.

Imbach et al. (2009) "Intravenous immunoglobulins induce potentially synergistic immunomodulations in autoimmune disorders," Vox Sanguinis, 10 pages.

Imbach, Paul (2012) "Treatment of immune thrombocytopenia with intravenous immunoglobulin and insights for other diseases," Swiss Medical Weekly, 10 pages.

International Preliminary Report on Patentability for PCT International Patent Application No. PCT/EP2013/068399, dated Mar. 10, 2015.

International Preliminary Report on Patentability for PCT International Patent Application No. PCT/US2014/072087, dated Jun. 28, 2016.

International Preliminary Report on Patentability for PCT International Patent Application No. PCT/IB2019/054786, dated Dec. 8, 2020.

International Preliminary Report on Patentability for PCT International Patent Application No. PCT/IB2016/000398, dated Sep. 12, 2017.

International Search Report and Written Opinion for PCT International Patent Application PCT/EP2017/077966, dated Jan. 29, 2018.

International Search Report and Written Opinion for PCT International Application No. PCT/IB2019/054786, dated Dec. 18, 2109 (27 pages).

International Search Report and Written Opinion for PCT International Patent Application No. PCT/EP2013/068399, dated Apr. 9, 2014.

International Search Report with Written Opinion for PCT International Patent Application No. PCT/US2014/072087, dated May 12, 2015.

International Search Report with Written Opinion for PCT International Patent Application No. PCT/EP2018/084034, dated Feb. 18, 2019.

International Search Report with Written Opinion for PCT International Patent Application No. PCT/IB2016/000398, dated Aug. 22, 2016.

International Search Report with Written Opinion for PCT International Patent Application No. PCT/EP2020/065716, dated Sep. 14, 2020.

International Search Report with Written Opinion for PCT International Patent Application No. PCT/EP2021/050275, dated Apr. 8, 2021.

Jacob et al. (2012) "Presence and Pathogenic Relevance of Antibodies to Clustered Acetylcholine Receptor in Ocular and Generalized Myasthenia Gravis," Arch Neurol., 69(8):994-1001.

Jain et al. (Aug. 20, 2012) "Fully recombinant IgG2a Fc multimers (stradomers) effectively treat collagen-induced arthritis and prevent idiopathic thrombocytopenic purpura in mice," Arthritis Research & Therapy 14:R192. pp. 1-12.

Jefferis et al. (1995) "Recognition sites on human IgG for Fcgamma receptors: the role of glycosylation," Immunology Letters, 44:111-117.

Jefferis et al. (1996) "Modulation of Fc(gamma)R and human complement activation by IgG3-core oligosaccharide interactions," Immunol. Lett. 54:101-104.

Jefferis et al. (2002) "Interaction sites on human IgG-Fc for FcgammaR: current models," Immunology Letters, 82:57-65.

Junghans (1997) "Finally! The Brambell receptor (FcRB). Mediator of transmission of immunity and protection from catabolism for IgG," Immunologic Research. 16(1):29-57.

Junghans et al. (1996) "The protection receptor for IgG catabolism is the beta2-microglobulin-containing neonatal intestinal transport receptor," Proc. Natl. Acad. Sci. USA. 93:5512-5516.

Kabat et al., "Unusual Distributions of amino Acids in Complementarity-determining (Hypervariable) Segments of Heavy and Light Chains of Immunoglobulins and Their Possible Roles in Specificity of Antibody-combining Sites", The Journal of Biological Chemistry, Oct. 1, 1977, 252(19): 6609-6616.

Kanda et al. (2006) "Comparison of biological activity among nonfucosylated therapeutic IgG1 antibodies with three different N-linked Fc oligosaccharides: the high-mannose, hybrid, and complex types," Glycobiol. 17(1):104-118.

Kang et al., "Rapid Formulation Development for Monoclonal Antibodies", BioProcess International, Apr. 12, 2016, retrieved from url: https://bioprocessintl.com/manufacturing/formulation/rapid-formulation-development-for-monoclonal-antibodies/.

Kim et al. (1999) "Mapping of the site on human IgG1 for binding of the MHC class I related receptor, FcRn," Eur. J. Immunol. 29:2819-2825.

(56) References Cited

OTHER PUBLICATIONS

Law et al. (1997) "High-dose intravenous immune globulin and the response to splenectomy in patients with idiopathic thrombocytopenic purpura," N. Engl. J. Med. 336:1494-1498.
Li et al. (2005) "Complete FcRn dependence for intravenous Ig therapy in autoimmune skin blistering diseases," J. Clin. Invest. 115(12):3440-3450.
Liu et al. (2007) "Amelioration of experimental autoimmune myasthenia gravis in rats by neonatal FcR blockade," J. Immunol. 178(8):5390-5398.
Liu et al. (2009) "Comparing the Autoantibody Levels and Clinical Efficacy of Double Filtration Plasmapheresis, Immunoadsorption, and Intravenous Immunoglobulin for the Treatment of Late-Onset Myasthenia Gravis," Therapeutic Apheresis and Dialysis, 14(2):153-160.
Low et al. (2009) "Inhibitors of the FcRn:IgG Protein-Protein Interaction," AAPS Journal. 11(3):432-434.
Lund et al. (1991) "Human Fc gamma RI and Fc gamma RII interact with distinct but overlapping sites on human IgG," J. Immunol. 147:2657-2662.
Lund et al. (1992) "Multiple binding sites on the CH2 Domain of IgG for Mouse FcgammaRII," Molecular Immunology, 29(1):53-59.
Lund et al. (1995) "Oligosaccharide-protein interactions in IgG can modulate recognition by Fcgamma receptors," The FASEB Journal 9:115-119.
Lund et al. (1996) "Multiple interactions of IgG with its core oligosaccharide can modulate recognition by complement and human Fc gamma receptor I and influence the synthesis of its oligosaccharide chains," J. Immunol. 157:4963-4969.
Lutterbach et al. (2007) "Lung cancer cell lines harboring MET gene amplification are dependent on Met for growth and survival," Cancer Research. 67(5):2081-2088.
MacCallum et al. (1996) "Antibody-antigen Interactions: Contact Analysis and Binding Site Topography," J. Mol. Biol., 262:732-745.
Martin et al. (2001) "Crystal Structure at 2.8 A of an FcRn/Heterodimeric Fc Complex Mechanism of pH-Dependent Binding," Molecular Cell, 7:867-877.
Massachusetts General Hospital (Dec. 10, 2012) "Suppremol's Sm101 shows a sustained clinical activity and a favorable safety profile in primary immune thrombocytopenia (ITP) patients," Press Release. Evaluate Ltd.
Medesan et al. (1997) "Delineation of the amino acid residues involved in transcytosis and catabolism of mouse IgG," J. Immunol. 158:2211-2217.
Mendell et al. (2001) "Randomized controlled trial of IVIg in untreated chronic inflammatory demyelinating polyradiculoneuropathy," Neurology. 56:445-449.
Meriggioli et al. (2009) "Autoimmune myasthenia gravis: emerging clinical and biological heterogeneity," Lancet Neurol. 8:475-490.
Mezo et al. (2008) "Reduction of IgG in nonhuman primates by a peptide antagonist of the neonatal Fc receptor FcRn," Proc. Natl. Acad. Sci. USA. 105(7):2337-2342.
Mi et al. (2008) "Targeting the neonatal Fc receptor for antigen delivery using engineered Fc fragments," J. Immunol. 181:7550-7561.
Mohamed et al. (Jan. 7, 2013) "Massive intravascular haemolysis after high dose intravenous immunoglobulin therapy," British Journal of Haematology. 160:570.
Montoyo et al. (2009) "Conditional deletion of the MHC class I-related receptor FcRn reveals the sites of IgG homeostasis in mice," Proc. Natl. Acad. Sci. USA. 106:2788-2793.
Morea et al. (2000) "Antibody Modeling: Implications for Engineering and Design," Methods, 20:267-279.
Newburger et al. (2004) "Diagnosis, Treatment, and Long-Term Management of Kawasaki Disease: A Statement for Health Professionals from the Committee on Rheumatic Fever, Endocarditis, and Kawasaki Disease, Council on Cardiovascular Disease in the Young, American Heart Association," Pediatrics. 114:1708-1733.
Newland et al. (1983) "High-dose intravenous IgG in adults with autoimmune thrombocytopenia," The Lancet, 84-87.
Nieswandt et al. (1999) "Acute systemic reaction and lung alterations induced by an antiplatelet integrin gpIIb/IIIa antibody in mice," Blood. 94:684-693.
Niknami et al. (Jun. 2013) "Beneficial effect of a multimerized immunoglobulin Fc in an animal model of inflammatory neuropathy (experimental autoimmune neuritis)," J. Peripher. Nerv. Syst. 18(2):141-52.
Ober et al. (2004) "Exocytosis of IgG as mediated by the receptor, FcRn: an analysis at the single-molecule level," Proc. Natl. Acad. Sci. USA. 101:11076-11081.
Ober et al. (2004) "Visualizing the site and dynamics of IgG salvage by the MHC Class I-related receptor, FcRn," J. Immunol. 172:2021-2029.
Oshima et al. (1998) "Characterization of murine CD70 by molecular cloning and mAb," Int. Immunol. 10(4):517-526.
Patel et al. (2011) "Neonatal Fc receptor blockade by Fc engineering ameliorates arthritis in a murine model," J. Immunol. 187(2):1015-1022.
Pevzner et al. (2011) "Anti-LRP4 autoantibodies in AChR-and MuSK-antibody-negative myasthenia gravis," J. Neurol., 9 pages.
Prabhat et al. (2007) "Elucidation of intracellular recycling pathways leading to exocytosis of the Fc receptor, FcRn, by using multifocal plane microscopy," Proc. Natl. Acad. Sci. USA. 104:5889-5894.
Presta et al. (2002) "Engineering therapeutic antibodies for improved function," Biochemical Society Transactions, 30(4):487-490.
Reddy et al. (2000) "Elimination of Fc Receptor-Dependent Effector Functions of a Modified IgG4 Monoclonal Antibody to Human CD4," J. Immunol., 164:1925-1933.
Robak et al., "Phase II, Multiple-Dose Study of Anti-FcRn Antibody, Rozanolixizumab (UCB7665), in Patients with Primary Immune Thrombocytopenia: Interim Analysis", Blood, Dec. 7, 2017, 130(Suppl. 1): 15, 59th Annual Meeting of the American-Society-of-Hematology, Dec. 9-12, 2017.
Roopenian et al. (2003) "The MHC class I-like IgG receptor controls perinatal IgG transport, IgG homeostasis, and fate of IgG-Fc-coupled drugs," J. Immunology. 170:3528-3533.
Roopenian et al. (2007) "FcRn: the neonatal Fc receptor comes of age," Nat. Rev. Immunol. 7(9):715-725.
Roux et al. (1998) "Comparisons of the Ability of Human IgG3 Hinge Mutants, IgM, IgE, and IgA2, to Form Small Immune Complexes: A Role for Flexibility and Geometry," The Journal of Immunology, 4083-4090.
Schwab et al. (Mar. 2013) "Intravenous immunoglobulin therapy: how does IgG modulate the immune system?" Nat. Rev. Immunol. 176(13).
Seidling et al. (2013) "Analysis of high-dose intravenous immunoglobulin therapy in 16 patients with refractory autoimmune blistering skin disease: high efficacy and no serious adverse events," Acta Derm Venereol. 93:346-349.
Semple (2010) "Animal models of immune thrombocytopenia (ITP)," Annals of Hematology. 89:37-44.
Sesarman et al. (2010) "The neonatal Fc receptor as therapeutic target in IgG-mediated autoimmune diseases," Cell. Mol. Life Sci. 67(15):2533-2550.
Sewell: Ed. (Jan. 22, 2010) First National Immunoglobulin Database Report. Department of Health.
Shang et al., "Modular protein expression by RNA trans-splicing enables flexible expression of antibody formats in mammalian cells from a dual-host phage display vector", Protein Engineering, Design & Selection, 2015, vol. 28, No. 10, pp. 437-444.
Shelton (1999) "Acquired myasthenia gravis: what we have learned from experimental and spontaneous animal models," Veterinary Immunology and Immunopathology. 69:239-249.
Shields et al. (2001) "High Resolution Mapping of the Binding Site on Human IgG1 for FcgammaRI, FcgammaRII, FcgammaRIII, and FcRn and Design of IgG1 Variants with Improved Binding to the FcgammaR," The Journal of Biological Chemistry, 276(9):6591-6604.

(56) References Cited

OTHER PUBLICATIONS

Sockolosky et al. (2015) "The neonatal Fc receptor, FcRn, as a target for drug delivery and therapy," Advanced Drug Delivery Reviews, 91:109-124.
Soliven (2012) "Autoimmune neuropathies: insights from animal models," Journal of the Peripheral Nervous System. 17:28-33.
Sorde et al. (2017) "Massive immune response against IVIg interferes with response against other antigens in mice: A new mode of action?" PLoS ONE, 12(10):e0186046, 15 pages.
Stamos et al. (2004) "Crystal structure of the HGF beta-chain in complex with the Sema domain of the Met receptor," EMBO J. 23(12):2325-2335.
Swiercz et al. (May 27, 2014) "Use of Fc-engineered antibodies as clearing agents to increase contrast during PET," J. Nucl. Med. 55:1204-1207.
Swiss Webster Mice, by TACONIC, Aug. 23, 2018, pp. 1-7.
Task Force of the Medical Scientific Advisory Board of the Myasthenia Gravis Foundation of America, et al. (2000) "Myasthenia gravis," Neurology, 55:16-23.
Tramontano et al. (1990) "Framework Residue 71 is a Major Determinant of the Position and Conformation of the Second Hypervariable Region in the VH Domains of Immunoglobulins," J. Mol. Biol., 215:175-182.
Ulrichts et al. (2018) "Neonatal Fc receptor antagonist efgartigimod safely and sustainably reduces IgGs in humans," J. Clin. Invest., 16 pages.
Ulrichts et al. (May 2017) "ARGX-113: Towards a Safe and Selective Elimination of Pathogenic Autoantibodies," 13th International Conference on Myasthenia Gravis and Related Disorders, May 15-17, 2017. New York, New York. Poster Presentation.
Ulrichts et al., "ARGX-113, a Novel Fc-Based Approach for Antibody-Induced Pathologies Such as Primary Immune Thrombocytopenia", Blood, vol. 128, No. 22, Dec. 2016, p. 4919, 58th annual Meeting and Exposition of the American-Society-of-Hematology; San Diego, CA, Dec. 3-6, 2016.
Vaccaro et al. (2005) "Engineering the Fc region of immunoglobulin G to modulate in vivo antibody levels," Nat. Biotechnol. 23(10):1283-1288.
Vaccaro et al. (2006) "Divergent activities of an engineered antibody in murine and human systems have implications for therapeutic antibodies" Proc. Natl. Acad. Sci. USA. 103(49):18709-18714.
Van Der Meche et al. (1992) "A randomized trial comparing intravenous immune globulin and plasma exchange in Guillain-Barre syndrome. Dutch Guillain-Barre Study Group," N. Engl. J. Med. 326:1123-1129.
Wang et al., "Protein aggregation and its inhibition on biopharmaceutics", International Journal of Pharmaceutics, Jan. 31, 2005, 289(1-2):1-30.
Wani et al. (2006) "Familial hypercatabolic hypoproteinemia caused by deficiency of the neonatal Fc receptor, FcRn, due to a mutant beta2-microglobulin gene," Proc. Natl. Acad. Sci. USA. 103(13):5084-5989.
Woods et al. (1984) "Autoantibodies against platelet glycoprotein lb in patients with chronic immune thrombocytopenic purpura," Blood. 64:156-160.
Xu et al. (2000) "In Vitro Characterization of Five Humanized OKT3 Effector Function Variant Antibodies," Cellular Immunology, 200:16-26.
Yang et al., (2011) "Non-radioactive serological diagnosis of myasthenia gravis and clinical features of patients from Tianjin, China," Journal of Neurological Sciences, 301:71-76, 2011.
Ying et al. (2012) "Soluble Monomeric IgG1 Fc," The Journal of Biological Chemistry, 287(23):19399-19408.
Ying et al. (2013) "Engineered Soluble Monomeric IgG1 CH3 Domain," The Journal of Biological Chemistry, 288 (35):25154-25164.
Zhang et al. (2012) "Autoantibodies to Lipoprotein-Related Protein in Patients with Double-Seronegative Myasthenia Gravis," Arch Neurol, 69(4):445-451.
Zhou et al. (2003) "Generation of mutated variants of the human form of the MHC class I-related receptor, FcRn, with increased affinity for mouse immunoglobulin G," J. Mol. Biol. 332:901-913.
Zhou et al. (2005) "Conferring the binding properties of the mouse MHC Class I related receptor, FcRn, onto the human ortholog by sequential rounds of site-directed mutagenesis," J. Mol. Biol. 345:1071-1081.
Zinman et al. (2007) "IV immunoglobulin in patients with myasthenia gravis: a randomized controlled trial," Neurology 68:837-841.
Bussel et al., "Eltrombopag for the Treatment of Chronic Idiopathic Thrombocytopenia Purpura", NEJM, 2007, 357(22): 2237-2247.
International Preliminary Report on Patentability for PCT International Patent Application No. PCT/EP2020/065716, dated Dec. 7, 2021.
Janeway et al., (2005) Immunobiology, Part II. The Recognition of Antigen, Chapter 5.
Khan et al., "Clinical Practice Updates in the Management of Immune Thrombocytopenia", P&T, Dec. 2017, 42(12): 756-763.
Newland et al., "Phase 2 study of efgartigimod, a novel FcRn antagonisr, in adult patients with primary immune thrombocytopenia", Am Journ Hematol., 2020, 95: 178-187.
Robak et al., "Single-Agent Ibrutinib Vs Chemoimmunotherapy Regimens for Treatment-Naïve Patients with Chronic Lymphocytic Leukemia (CLL): A Cross-Trial Comparison", Blood, 2017, 130 (Suppl. 1): 1750.
Robak et al., "Efficacy and Safety of a new intravenous immunoglobulin 10% formulation (octagam® 10%) in patients with immune throbmbocytopenia", Hematology, 2010, 15(5): 351-359.
U.S. Appl. No. 14/580,771 2015/0218239 U.S. Pat. No. 10,316,073, filed Dec. 23, 2014 Aug. 6, 2015 Jun. 11, 2019, Peter Ulrichts.
U.S. Appl. No. 15/821,104 2018/0179258, filed Nov. 22, 2017, Peter Ulrichts.
U.S. Appl. No. 15/064,195 2016/0264669, filed Mar. 8, 2016 Sep. 15, 2016, Peter Ulrichts.
U.S. Appl. No. 16/213,422 2019/0194277, filed Dec. 7, 2018 Jun. 27, 2019, Johannes de Haard.
U.S. Appl. No. 16/435,166 2020/0024344, filed Jun. 7, 2019 Jan. 23, 2020, Hans de Haard.
PCT/IB2019/054786 WO 2019/234713, Jun. 7, 2019 Dec. 12, 2019, Hans de Haard.
U.S. Appl. No. 17/144,481 2021/0236596, filed Jan. 8, 2021 Aug. 5, 2021, Peter Verheesen.
"Anthony et al., Apr. 18, 2008, Science, 320(5874): 373-376", Document D14 submitted with Notice of Opposition for European Patent No. 3087095 (Application No. 14827372.5), dated May 7, 2020.
"ArGEN-X advances ARGX-113 into preclinical development for autoimmune disorders, Apr. 24, 2014", Document D38 submitted with Notice of Opposition for European Patent No. 3087095 (Application No. 14827372.5), dated May 7, 2020.
"ArGEN-X Announces Positive Preclinical Results for ARGX-113, Aug. 19, 2014", Document D39 submitted with Notice of Opposition for European Patent No. 3087095 (Application No. 14827372.5), dated May 7, 2020.
"Assignment submission for U.S. Appl. No. 61/920,547 confirming change of legal form of arGEN-X B.V. to arGEN-X N.V. on May 28, 2014", Document D30 submitted with Notice of Opposition for European Patent No. 3087095 (Application No. 14827372.5), dated May 7, 2020.
"Blumberg & Lencer, Oct. 2005, Nat Biotechnol., 23(10): 1232-1234", Document D03 submitted with Notice of Opposition for European Patent No. 3087095 (Application No. 14827372.5), dated May 7, 2020.
"Bruhns et al., Apr. 2003, Immunity, 18(4): 573-571", Document D16 submitted with Notice of Opposition for European Patent No. 3087095 (Application No. 14827372.5), dated May 7, 2020.
"Brych et al., Feb. 2010, J Pharm Sci., 99(2): 764-781", Document D37 submitted with Notice of Opposition for European Patent No. 3087095 (Application No. 14827372.5), dated May 7, 2020.
"Carter, May 2006, Nat Rev immunol., 6(5): 343-357", Document D22 submitted with Notice of Opposition for European Patent No. 3087095 (Application No. 14827372.5), dated May 7, 2020.

(56) References Cited

OTHER PUBLICATIONS

"Challa et al., Sep.-Oct. 2013, MAbs, 5(5): 655-659", Document D10 submitted with Notice of Opposition for European Patent No. 3087095 (Application No. 14827372.5), dated May 7, 2020.
"Corrected Filing Receipt for U.S. Appl. No. 61/920,547 dated Apr. 16, 2015", Document D27 submitted with Notice of Opposition for European Patent No. 3087095 (Application No. 14827372.5), dated May 7, 2020.
"Dall'Acqua et al., Nov. 1, 2002, J Immunol., 169(9): 5171-5180", Document D21 submitted with Notice of Opposition for European Patent No. 3087095 (Application No. 14827372.5), dated May 7, 2020.
"Debre et al., Oct. 16, 1993, Lancet, 342: 945-949", Document D12 submitted with Notice of Opposition for European Patent No. 3087095 (Application No. 14827372.5), dated May 7, 2020.
"Dimitrov, Jan.-Feb. 2009, MAbs, 1(1): 26-28", Document D20 submitted with Notice of Opposition for European Patent No. 3087095 (Application No. 14827372.5), dated May 7, 2020.
"EP 1896503 Amended Claims and Response submitted Feb. 23, 2014 during prosecution of the application which led to grant of D1", Document D02a submitted with Notice of Opposition for European Patent No. 3087095 (Application No. 14827372.5), dated May 7, 2020.
"EP 1896503 B1 dated Oct. 29, 2014", Document D01 submitted with Reply to Notice of Opposition for European Patent No. 3087095 (Application No. 14827372.5), dated May 7, 2020.
"EP 3087095 B1 dated Aug. 7, 2019" submitted with Notice of Opposition for European Patent No. 3087095 (Application No. 14827372.5), dated May 7, 2020.
"Filing Receipt for U.S. Appl. No. 61/920,547 dated Jan. 21, 2014", Document D25 submitted with Notice of Opposition for European Patent No. 3087095 (Application No. 14827372.5), dated May 7, 2020.
"Gan et al., May 2009, Traffic, 10(5): 600-614", Document D08 submitted with Notice of Opposition for European Patent No. 3087095 (Application No. 14827372.5), dated May 7, 2020.
"Goh and Ng, Sep. 2018, Crit Rev Biotechnol., 38(6): 851-867", Document D19 submitted with Notice of Opposition for European Patent No. 3087095 (Application No. 14827372.5), dated May 7, 2020.
"Gómez-Guerrero et al., Feb. 15, 2000, J Immunol., 164(4): 2092-2101", Document D15 submitted with Notice of Opposition for European Patent No. 3087095 (Application No. 14827372.5), dated May 7, 2020.
"Inventor Assignment of U.S. Appl. No. 61/920,547 to arGEN-X B.V. executed Oct. 31, 2014 and Nov. 4, 2014", Document D29 submitted with Notice of Opposition for European Patent No. 3087095 (Application No. 14827372.5), dated May 7, 2020.
"Inventor Assignment of U.S. Appl. No. 61/920,547 to the Board of Regents of the University of Texas System executed Dec. 23, 2014", Document D28 submitted with Notice of Opposition for European Patent No. 3087095 (Application No. 14827372.5), dated May 7, 2020.
"Jefferis and Lefranc, Jul.-Aug. 2009, MAbs, 1(4): 332-338", Document D35 submitted with Notice of Opposition for European Patent No. 3087095 (Application No. 14827372.5), dated May 7, 2020.
"Kaneko et al., Aug. 4, 2006, Science, 313(5787): 670-673", Document D17 submitted with Notice of Opposition for European Patent No. 3087095 (Application No. 14827372.5), dated May 7, 2020.
"Notice of Opposition" to European Patent No. 3087095 (Application No. 14827372.5), dated May 7, 2020, 47 pages.
"Online Filing Acknowledgement for Notice of Opposition" for European Patent No. 3087095 (Application No. 14827372.5), dated May 7, 2020, 3 pages.
"Patel et al., Jul. 15, 2011, J Immunol., 187(2): 1015-1022", Document D09 submitted with Notice of Opposition for European Patent No. 3087095 (Application No. 14827372.5), dated May 7, 2020.
"PCT Request for as filed for PCT/US2014/072087 on Dec. 23, 2014", Document D34 submitted with Notice of Opposition for European Patent No. 3087095 (Application No. 14827372.5), dated May 7, 2020.
"Putnam and Miyake, Apr. 1958, J Biol Chem, 231(2):671-684", Document D33 submitted with Notice of Opposition for European Patent No. 3087095 (Application No. 14827372.5), dated May 7, 2020.
"Pyzik et al., Jul. 10, 2019, Front Immunol., 10: 1540", Document D31 submitted with Notice of Opposition for European Patent No. 3087095 (Application No. 14827372.5), dated May 7, 2020.
"Samuelsson et al., Jan. 19, 2001, Science, 291(5503): 484-486", Document D13 submitted with Notice of Opposition for European Patent No. 3087095 (Application No. 14827372.5), dated May 7, 2020.
"Schwab and Nimmerjahn, Mar. 2013, Nat Rev Immunol., 13(3): 176-189", Document D11 submitted with Notice of Opposition for European Patent No. 3087095 (Application No. 14827372.5), dated May 7, 2020.
"Sequence alignment of SEQ ID No. 22 from D6 and SEQ ID Nos. 1, 2, and 3 from the Patent", Document D32 submitted with Notice of Opposition for European Patent No. 3087095 (Application No. 14827372.5), dated May 7, 2020.
"Sequence Alignment of SEQ ID Nos. 1-3 from Patent and corresponding portion of Uniprot ID: P01857", Document D24 submitted with Notice of Opposition for European Patent No. 3087095 (Application No. 14827372.5), dated May 7, 2020.
"Shields et al., Mar. 2, 2001, J Biol Chem., 276(9): 6591-6604", Document D23 submitted with Notice of Opposition for European Patent No. 3087095 (Application No. 14827372.5), dated May 7, 2020.
"Ulrichts et al., Oct. 1, 2018, J Clin Invest., 128(10): 4372-4386", Document D18 submitted with Notice of Opposition for European Patent No. 3087095 (Application No. 14827372.5), dated May 7, 2020.
"Vacarro et al., Dec. 2006, Proc Natl Acad Sci USA, 103(49): 18709-18714", Document D07 submitted with Notice of Opposition for European Patent No. 3087095 (Application No. 14827372.5), dated May 7, 2020.
"Vaccarro et al., Oct. 2005, Nat Biotechnol., 23(10): 1283-1288", Document D04 submitted with Notice of Opposition for European Patent No. 3087095 (Application No. 14827372.5), dated May 7, 2020.
"Ward & Ober, 2009, Chapter 4, Adv. Immunol., 103: 77-115", Document D05 submitted with Notice of Opposition for European Patent No. 3087095 (Application No. 14827372.5), dated May 7, 2020.
"Weiner and Carter, May 2005, 23(5): 556-557", Document D36 submitted with Notice of Opposition for European Patent No. 3087095 (Application No. 14827372.5), dated May 7, 2020.
"WO 2006/130834 A2 dated Dec. 7, 2006", Document D02 submitted with Notice of Opposition for European Patent No. 3087095 (Application No. 14827372.5), dated May 7, 2020.
"WO 2013/074598 A1 dated May 23, 2013", Document D06 submitted with Notice of Opposition for European Patent No. 3087095 (Application No. 14827372.5), dated May 7, 2020.
"WO 2015/100299 A1 dated Jul. 2, 2015" submitted with Notice of Opposition for European Patent No. 3087095 (Application No. 14827372.5), dated May 7, 2020.
Evoli et al., "Diagnosis and therapy of myasthenia gravis with antibodies to muscle-specific kinase", Autoimmunity Reviews, 2013, 12(9): 931-935.
Jaretzkl et al., "Myasthenia gravis: recommendations for clinical research standards. Task Force of the Medical Scientific Advisory Board of the Myasthenia Gravis Foundation of America", Ann Thorac Surg., Jul. 2000, 70(1): 327-334.
Joshi et al., "An Update on Disease Modifying Antirheumatic Drugs", Inflammation and Allergy—Drug Targets, 2014, 13: 249-261.
Li et al., "Myasthenia gravis: newer therapies offer sustained improvement", Cleveland Clinic Journal of Medicine, 2013, 80(11): 711-721.

(56) References Cited

OTHER PUBLICATIONS

Rosenwasser et al., "Anti-CD23", Clinical Reviews in Allergy and Immunology, Aug. 2005, 29(1): 61-72.
Silvestri et al., "Treatment-Refractory Myasthenia Gravis", Journal of Clinical Neuromuscular Disease, Jun. 2014, 15(4): 167-178.
U.S. Appl. No. 15/821,104 2018/0179258, filed Nov. 22, 2017 Jun. 28, 2018, Peter Ulrichts.
U.S. Appl. No. 17/144,481, filed Jan. 8, 2021, Peter Verheesen.

X-axis: Shear rate $\gamma$ [1/s]
Left Y-axis: Viscosity $\eta$ [Pa·s]
Right Y-axis: Shear stress $\tau$ [Pa]

F1 = F12; F2 = F13; F3= F14; F4 = F15

F1 = F12; F2 = F13; F3= F14; F4 = F15

F1 = F12; F2 = F13; F3= F14; F4 = F15

F1 = F12; F2 = F13; F3= F14; F4 = F15

F1 = F12; F2 = F13; F3= F14; F4 = F15

F1 = F12; F2 = F13; F3 = F14; F4 = F15

F1 = F12; F2 = F13; F3 = F14; F4 = F15

F1 = F12; F2 = F13; F3= F14; F4 = F15

F1 = F12; F2 = F13; F3= F14; F4 = F15

F1 = F12; F2 = F13; F3= F14; F4 = F15

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1 = F13; F2 = F16; F3 = F17; F4 = F18; F5 = F19; F6 = F20; F7 = F21

F1V = F22; F2V = F23; F1S = F24; F2S = F25; F3S = F26; F4S = F27

F1V = F22; F2V = F23; F1S = F24; F2S = F25; F3S = F26; F4S = F27

F1V = F22; F2V = F23; F1S = F24; F2S = F25; F3S = F26; F4S = F27

F1V = F22; F2V = F23; F1S = F24; F2S = F25; F3S = F26; F4S = F27

F1V = F22; F2V = F23; F1S = F24; F2S = F25; F3S = F26; F4S = F27

F1V = F22; F2V = F23; F1S = F24; F2S = F25; F3S = F26; F4S = F27

# PHARMACEUTICAL FORMULATIONS OF FCRN INHIBITORS SUITABLE FOR SUBCUTANEOUS ADMINISTRATION

RELATED APPLICATIONS

The instant application claims the benefit of priority to U.S. Provisional Patent Application Ser. No. 62/858,806, entitled "PHARMACEUTICAL FORMULATIONS OF FCRN INHIBITORS SUITABLE FOR SUBCUTANEOUS ADMINISTRATION", filed Jun. 7, 2019. The contents of afore-mentioned application are incorporated by reference herein.

SEQUENCE LISTING

The instant application contains a Sequence Listing which has been submitted electronically in ASCII format and is hereby incorporated by reference in its entirety. Said ASCII copy, created on Jun. 5, 2020, is named 706874 AGX0943 ST25.txt and is 6489 bytes in size.

BACKGROUND

Immunoglobulin gamma (IgG) antibodies play a key role in the pathology of many disorders, such as autoimmune diseases, inflammatory diseases, and disorders in which the pathology is characterized by over-expression of IgG antibodies (e.g., hypergammaglobulinemia) (see e.g. Junghans, *Immunol Res.* 16 (1):29 (1997)).

The half-life of IgG in the serum is prolonged relative to the serum half-life of other plasma proteins (Roopenian et al., *J Immunol.* 170:3528 (2003); Junghans and Anderson, *Proc. Natl. Acad. Sci. USA* 93:5512 (1996)). This long half-life is due, in part, to the binding of the Fc region of IgG to the neonatal Fc receptor (FcRn). Although FcRn was originally characterized as a neonatal transport receptor for maternal IgG, it also functions in adults to protect IgG from degradation. FcRn binds to pinocytosed IgG and protects the IgG from transport to degradative lysosomes by recycling it back to the extracellular compartment. This recycling is facilitated by the pH-dependent binding of IgG to FcRn, where the IgG/FcRn interaction is stronger at acidic endosomal pH than at extracellular physiological pH.

When the serum concentration of IgG reaches a level that exceeds available FcRn molecules, unbound IgG is not protected from degradative mechanisms and will consequently have a reduced serum half-life. Thus, inhibition of IgG binding to FcRn reduces the serum half-life of IgG by preventing IgG endosomal recycling of IgG. Accordingly, agents that antagonize the binding of IgG to FcRn may be useful for regulating, treating or preventing antibody-mediated disorders, such as autoimmune diseases, inflammatory diseases, etc. Certain of these diseases are currently treated, at least in part, by intravenous infusion of pooled IgG (IVIg) from human donors. As many of these autoimmune diseases are chronic, afflicted individuals may require repeated administrations of IVIg and/or other suitable therapies in order to manage their disease.

In another approach, blocking antibodies to FcRn have been developed to inhibit IgG Fc binding to FcRn (see e.g. WO 2002/043658). Peptides have also been identified that bind to and antagonize FcRn function (see e.g. U.S. Pat. Nos. 6,212,022 and 8,101,186). In addition, full-length IgG antibodies comprising variant Fc receptors with enhanced FcRn binding and decreased pH dependence have also been identified that antagonize FcRn binding to IgG (see e.g. U.S. Pat. No. 8,163,881 and Vaccaro et al., *Nat Biotechnol.* 23(10): 1283-1288 (2005)).

Recently, another FcRn inhibitor, a modified version of human IgG1 Fc fragment, named efgartigimod (also known as ARGX-113), has been developed. See WO 2015/100299, the entire contents of which are incorporated herein by reference. ARGX-113 is currently undergoing clinical trials in a number of autoimmune diseases, including myasthenia gravis (MG) and immune thrombocytopenia (ITP).

A need still exists for improved formulations and methods of administration of FcRn inhibitors for use in the treatment of autoimmune diseases.

SUMMARY

Disclosed herein are various formulations of ARGX-113, including formulations useful as pharmaceutical compositions, methods for their preparation, devices comprising the various formulations, and uses thereof. In certain embodiments the formulations are suitable and useful for administration of ARGX-113 to a human subject. In certain embodiments the formulations are suitable and useful for subcutaneous administration of ARGX-113 to a human subject. The formulations can be used in the treatment of any condition that would benefit from inhibition of FcRn-mediated antibody recycling. Such conditions can include any one or more of various antibody-mediated autoimmune diseases, including, for example and without limitation, myasthenia gravis (MG) and immune thrombocytopenia (ITP).

An aspect of the invention is an aqueous formulation comprising about 100-300 mg/mL of an isolated neonatal Fc receptor (FcRn) antagonist in 20-60 mM histidine/histidine HCl, 0-70 mM sucrose, 0-150 mM NaCl, 0-250 mM arginine HCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 100-300 mg/mL of the isolated neonatal Fc receptor (FcRn) antagonist in 20-60 mM histidine/histidine HCl, 0-70 mM sucrose, about 100 mM NaCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 100-300 mg/mL of the isolated neonatal Fc receptor (FcRn) antagonist in 20-60 mM histidine/histidine HCl, 0-70 mM sucrose, 100-250 mM arginine HCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 100-300 mg/mL of the isolated neonatal Fc receptor (FcRn) antagonist in 20-60 mM histidine/histidine HCl, 100-250 mM arginine HCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In each of the foregoing aspects and embodiments, in certain embodiments, the aqueous formulation comprises 20 or 50 mM histidine.

In each of the foregoing aspects and embodiments, in certain embodiments, the aqueous formulation comprises 0.02%-0.04% (w/v) polysorbate 20 or polysorbate 80.

In each of the foregoing aspects and embodiments, in certain embodiments, the aqueous formulation comprises 0 or 10 mM L-methionine.

In each of the foregoing aspects and embodiments, in certain embodiments, the pH is 6.0 or 6.5.

In each of the foregoing aspects and embodiments, in certain embodiments, the amino acid sequence of each of the Fc domains consists of SEQ ID NO: 1.

An aspect of the invention is an aqueous formulation comprising about 100-200 mg/mL of an isolated neonatal Fc receptor (FcRn) antagonist in 20 mM histidine/histidine HCl, 60 mM sucrose, 100 mM NaCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 100-200 mg/mL ARGX-113 in 20 mM histidine/histidine HCl, 60 mM sucrose, 100 mM NaCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 150 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 165 mg/mL ARGX-113 in 20 mM histidine/histidine HCl, 60 mM sucrose, 100 mM NaCl, and about 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 175 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 180 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising water, 200 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 100-200 mg/mL of an isolated neonatal Fc receptor (FcRn) antagonist in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 100-200 mg/mL ARGX-113 in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 165 mg/mL of an isolated neonatal Fc receptor (FcRn) antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises 165 mg/mL ARGX-113 in 20 mM histidine/histidine HCl, 60 mM sucrose, 100 mM NaCl, 10 mM L-methionine, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 175 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 180 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 200 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 100-200 mg/mL of an isolated neonatal Fc receptor (FcRn) antagonist in 50 mM histidine/histidine HCl, 60 mM sucrose, 150 mM arginine HCl, and 0.02%-0.04% (w/v) polysorbate 20 or polysorbate 80, pH 6.0, wherein the isolated FcRn antagonist consisting of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprising about 100-200 mg/mL ARGX-113 in 50 mM histidine/histidine HCl, 60 mM sucrose, 100 mM arginine HCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of an Fc domain homodimer, wherein the amino acid sequence of each of the Fc domains consists of SEQ ID NO: 1.

An aspect of the invention is an aqueous formulation comprising about 100-200 mg/mL of an isolated neonatal Fc receptor (FcRn) antagonist in 20 mM histidine/histidine HCl, 60 mM sucrose, 100 mM arginine HCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprising about 100-200 mg/mL ARGX-113 in 20 mM histidine/histidine HCl, 60 mM sucrose, 100 mM arginine HCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 175 mg/mL ARGX-113 in 20 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 180 mg/mL ARGX-113 in 20 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 200 mg/mL ARGX-113 in 20 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising 250 mg/mL, 300 mg/mL or more than 300 mg/mL ARGX-113 in 20 mM histidine/histidine HCl, 60 mM sucrose, 100 mM arginine HCl, 10 mM L-methionine, and 0.03% (w/v) polysorbate 20, having a pH of about 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 100-300 mg/mL of an isolated neonatal Fc receptor (FcRn) antagonist in about 50 mM histidine/histidine HCl, about 200 mM arginine HCl, having a pH of 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 200-300 mg/mL of an isolated neonatal Fc receptor (FcRn) antagonist in 50 mM histidine/histidine HCl, 200 mM arginine HCl, having a pH of 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1.

In an embodiment, the aqueous formulation comprises about 250-300 mg/mL of an isolated neonatal Fc receptor (FcRn) antagonist in 50 mM histidine/histidine HCl, 200 mM arginine HCl, having a pH of 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1.

In certain embodiments of each of the foregoing aspects of the invention, the aqueous formulation is substantially free of dissolved oxygen.

In certain embodiments of each of the foregoing aspects of the invention, the aqueous formulation is suitable for in vivo use.

In certain embodiments of each of the foregoing aspects of the invention, the aqueous formulation is suitable for in vivo subcutaneous use.

An aspect of the invention is a packaged pharmaceutical product comprising a sterile container comprising a therapeutically effective amount of the aqueous formulation of any one of the foregoing aspects and embodiments.

An aspect of the invention is a device comprising a therapeutically effective amount of the aqueous formulation of any one of the foregoing aspects and embodiments.

In certain embodiments, the device comprises or consists of a syringe comprising the aqueous formulation.

In certain embodiments, the syringe is a pre-filled syringe.

DETAILED DESCRIPTION

ARGX-113

Figure 1:
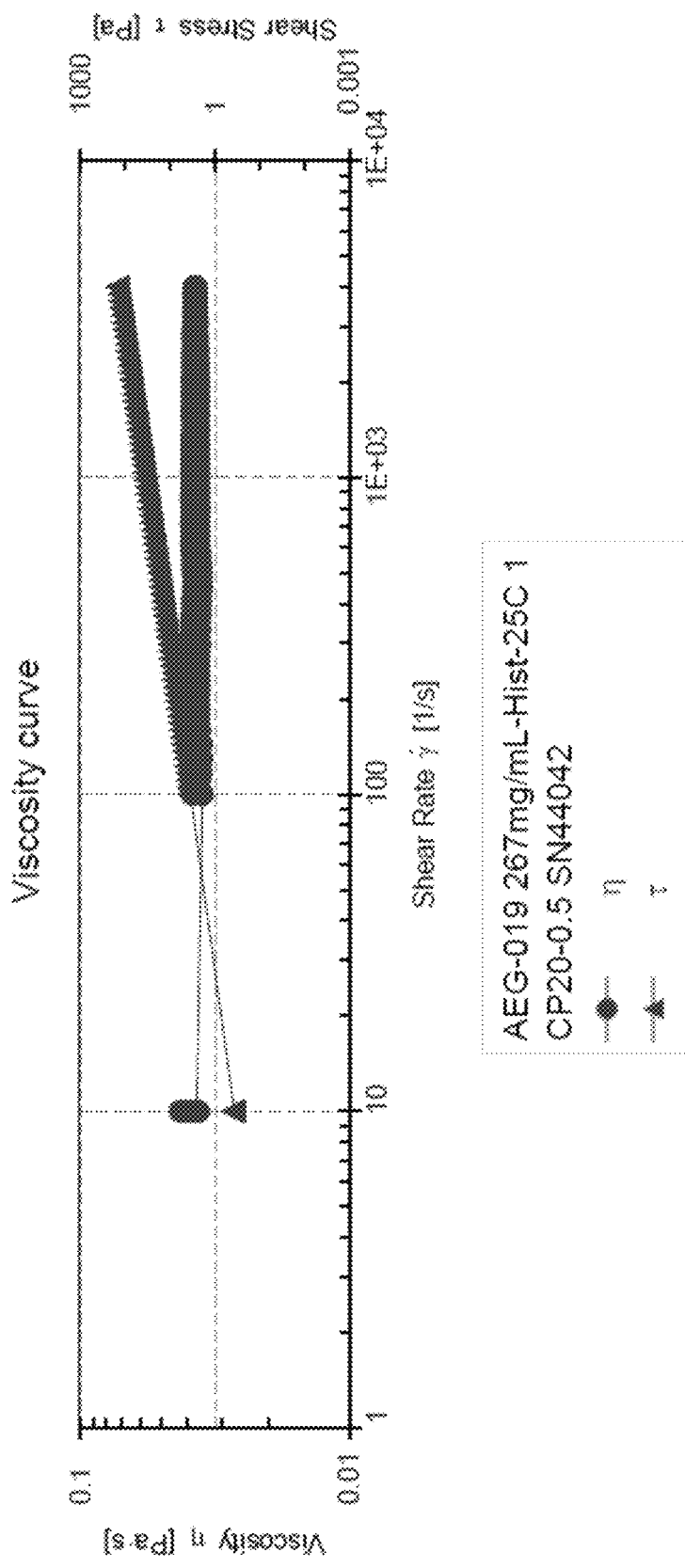
FIG. 1 depicts shear thinning/thickening behavior of ARGX-113 at highest concentration studied by shear rate ramping from 0-4000 s$^{-1}$.

In certain embodiments, the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3. ARGX-113 is a variant Fc region of human IgG1, wherein the Fc region comprises the amino acids Y, T, E, K, F, and Y at EU positions 252, 254, 256, 433, 434, and 436, respectively.

In particular, ARGX-113 is an isolated FcRn antagonist consisting of a variant Fc region, wherein said variant Fc region consists of an Fc domain homodimer, wherein the amino acid sequence of each of the Fc domains consists of SEQ ID NO: 1.

```
                                              (SEQ ID NO: 1)
DKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALKFHYTQKSLSLSPG (SEQ ID NO: 2)
DKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK
```

```
GFYPSDIAVEWESNGQPENNYKTTPPVLDSDGSFFLYSKLTVDKSRWQQG

NVFSCSVMHEALKFHYTQKSLSLSPGK (SEQ ID NO: 3)
DKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALKFHYTQKSLSLSPDSNLWN
```

The N-terminal aspartic acid residue (D) in SEQ ID NO: 1 corresponds to EU position 221, and the C-terminal lysine (K) of SEQ ID NO: 2 corresponds to EU position 447.

In certain embodiments, the aqueous formulations and pharmaceutical compositions of the invention are substantially homogeneous for the polypeptide of SEQ ID NO: 1. In certain embodiments, the aqueous formulations and pharmaceutical compositions of the invention comprise a population of polypeptides wherein at least 90% of the polypeptides (e.g., at least 90%, 91%, 92%, 93%, 94%, 95%, 96%, 97%, 98%, 99% or more) consist of an Fc domain homodimer, wherein the amino acid sequence of each of the Fc domains of the homodimer consists of SEQ ID NO: 1.

In certain embodiments, the aqueous formulations and pharmaceutical compositions of the invention are substantially homogeneous for the polypeptide of SEQ ID NO: 2. In particular preferred embodiments, the aqueous formulations and pharmaceutical compositions of the invention comprise a population of polypeptides wherein at least 90% of the polypeptides (e.g., at least 90%, 91%, 92%, 93%, 94%, 95%, 96%, 97%, 98%, 99% or more) consist of an Fc domain homodimer, wherein the amino acid sequence of each of the Fc domains of the homodimer consists of SEQ ID NO: 2. In certain embodiments, more than 90% of the polypeptides lack a C-terminal lysine residue (K) at EU position 448.

In certain embodiments, each Fc domain of ARGX-113 further comprises an N-linked glycan at EU position 297, wherein the N-linked glycan has a bisecting N-acetylglucosamine (GlcNAc) structure.

In certain embodiments, the aqueous formulations and pharmaceutical compositions of the invention are substantially homogeneous for the polypeptide of SEQ ID NO: 3. In certain embodiments, the aqueous formulations and pharmaceutical compositions of the invention comprise a population of polypeptides wherein at least 90% of the polypeptides (e.g., at least 90%, 91%, 92%, 93%, 94%, 95%, 96%, 97%, 98%, 99% or more) consist of an Fc domain homodimer, wherein the amino acid sequence of each of the Fc domains of the homodimer consists of SEQ ID NO: 3.

Antibody-Mediated Autoimmune Diseases

The formulations and compositions of the present invention will find use in the treatment of antibody-mediated and/or antibody-related autoimmune diseases.

Antibody-mediated and/or antibody-related autoimmune diseases are well known. Non-limiting examples of antibody-mediated and/or antibody-related autoimmune diseases include allogenic islet graft rejection, alopecia areata, ankylosing spondylitis, antiphospholipid syndrome, autoimmune Addison's disease, Alzheimer's disease, antineutrophil cytoplasmic antibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac sprue-dermatitis, chronic fatigue immune dysfunction syndrome, chronic inflammatory demyelinating polyneuropathy (CIDP), Churg-Strauss syndrome, cicatricial pemphigoid, CREST (calcinosis, Raynaud phenomenon, esophageal dysmotility, sclerodactyly, and telangiectasia) syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barré syndrome, Goodpasture's syndrome, graft-versus-host disease (GVHD), Hashimoto's thyroiditis, hemophilia A, idiopathic pulmonary fibrosis, idiopathic thrombocytopenic purpura (immune thrombocytopenia; ITP), IgA neuropathy, IgM polyneuropathies, immune mediated thrombocytopenia, juvenile arthritis, Kawasaki's disease, lichen planus, lupus erythematosus, Meniere's disease, mixed connective tissue disease, multiple sclerosis, type 1 diabetes mellitus, multifocal motor neuropathy (MMN), myasthenia gravis (MG), paraneoplastic bullous pemphigoid, pemphigus vulgaris, pemphigus *foliaceus*, pernicious anemia, polyarteritis *nodosa*, polychrondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, sarcoidosis, scleroderma, Sjögren's syndrome, solid organ transplant rejection, stiff-man syndrome, systemic lupus erythematosus (SLE), Takayasu arteritis, toxic epidermal necrolysis (TEN), Stevens Johnson syndrome (SJS), temporal arteritis/giant cell arteritis, thrombotic thrombocytopenia purpura, ulcerative colitis, uveitis, dermatitis herpetiformis vasculitis, anti-neutrophil cytoplasmic antibody (ANCA)-associated vasculitides, vitiligo, and Wegener's granulomatosis.

In certain embodiments, the antibody-mediated autoimmune disease is selected from the group consisting of immune thrombocytopenia (ITP) and myasthenia gravis (MG).

Formulations

The formulations and compositions of the invention will find use in any disease or condition in which it is desirable to reduce serum levels of an Fc-containing agent in a subject. Fc-containing agents include, without limitation, autoantibodies, therapeutic antibodies, diagnostic antibodies, and immune complexes. Additional non-limiting examples of Fc-containing agents include imaging agents (e.g., labeled antibodies), antibody-drug conjugates (ADCs), Fc fusion proteins (e.g., immunoadhesins), and immunogenic agents (e.g., non-human antibodies).

Furthermore, in diseases or conditions requiring administration of a therapeutic agent, the subject will often develop antibodies (e.g., anti-drug antibodies) against the therapeutic agent, which, in turn, prevent the therapeutic agent from being available for its intended therapeutic purpose or cause an adverse reaction in the subject. Accordingly, the formulations and compositions disclosed herein can also be used to remove antibodies (e.g., anti-drug antibodies) against the therapeutic agent that develop in a subject.

An aspect of the invention is an aqueous formulation comprising about 100-300 mg/mL of an isolated neonatal Fc receptor (FcRn) antagonist in 20-60 mM histidine/histidine HCl, 0-70 mM sucrose, 0-150 mM NaCl, 0-250 mM arginine HCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation comprises about 100-300 mg/mL of the isolated neonatal Fc receptor (FcRn) antagonist in 20-60 mM histidine/histidine HCl, 0-70 mM sucrose, 100 mM NaCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation comprises about 100-300 mg/mL of the isolated neonatal Fc receptor (FcRn) antagonist in 20-60 mM histidine/histidine HCl, 0-70 mM sucrose, 100-250 mM arginine HCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation comprises about 100-300 mg/mL of the isolated neonatal Fc receptor (FcRn) antagonist in 20-60 mM histidine/histidine HCl, 100-250 mM arginine HCl, 0.02%-0.05% (w/v) polysorbate 20 or polysorbate 80, 0-15 mM L-methionine, pH 6.0-6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In each of the foregoing aspects and embodiments, in certain embodiments, the aqueous formulation comprises 20 or 50 mM histidine.

In each of the foregoing aspects and embodiments, in certain embodiments, the aqueous formulation comprises 0.02%-0.04% polysorbate 20 or polysorbate 80.

In each of the foregoing aspects and embodiments, in certain embodiments, the aqueous formulation comprises 0 or 10 mM L-methionine.

In each of the foregoing aspects and embodiments, in certain embodiments, the pH is 6.0 or 6.5.

In each of the foregoing aspects and embodiments, in certain embodiments, the amino acid sequence of each of the Fc domains consists of SEQ ID NO: 1.

An aspect of the invention is an aqueous formulation comprising about 100 to about 300 mg/mL of an isolated FcRn antagonist in 20 mM histidine/histidine HCl, 60 mM sucrose, 100 mM NaCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

An aspect of the invention is an aqueous formulation comprising about 100 to about 200 mg/mL of an isolated FcRn antagonist in 20 mM histidine/histidine HCl, 60 mM sucrose, 100 mM NaCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

An aspect of the invention is an aqueous formulation comprising about 100-300 mg/mL of an isolated neonatal Fc receptor (FcRn) antagonist in 20 mM histidine/histidine HCl, 60 mM sucrose, 100 mM NaCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100 to about 300 mg/mL ARGX-113 in 20 mM histidine/histidine HCl, 60 mM sucrose, 100 mM NaCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 100-200 mg/mL of an isolated neonatal Fc receptor (FcRn) antagonist in 20 mM histidine/histidine HCl, 60 mM sucrose, 100 mM NaCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100 to about 200 mg/mL ARGX-113 in 20 mM histidine/histidine HCl, 60 mM sucrose, 100 mM NaCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

As used herein, the term "about" refers to an amount within ±10% of any given specified amount. For example, about 200 mg/mL encompasses 90% to 110% of 200 mg/mL, i.e., 180 to 220 mg/mL.

In certain embodiments, the aqueous formulation comprises 100-300 mg/mL ARGX-113.

In certain embodiments, the aqueous formulation comprises 100-200 mg/mL ARGX-113.

In certain embodiments, the aqueous formulation comprises about 150 to about 200 mg/mL ARGX-113. In certain embodiments, the aqueous formulation comprises 150-200 mg/mL ARGX-113.

In certain embodiments, the aqueous formulation comprises about 150 to about 180 mg/mL ARGX-113. In certain embodiments, the aqueous formulation comprises 150-180 mg/mL ARGX-113.

In certain embodiments, the aqueous formulation comprises about 165 mg/mL ARGX-113.

In certain embodiments, the aqueous formulation comprises about 175 mg/mL ARGX-113.

In certain embodiments, the aqueous formulation comprises about 180 mg/mL ARGX-113.

In certain embodiments, the aqueous formulation comprises about 250 mg/mL ARGX-113.

In certain embodiments, the aqueous formulation comprises about 300 mg/mL ARGX-113.

In accordance with each of the aforementioned embodiments, in certain embodiments, the aqueous formulation comprises 0.02%-0.04% (w/v) polysorbate 20. In certain embodiments, the aqueous formulation comprises 0.02% (w/v) polysorbate 20. In certain embodiments, the aqueous formulation comprises 0.03% (w/v) polysorbate 20. In certain embodiments, the aqueous formulation comprises 0.04% (w/v) polysorbate 20.

Alternatively, in accordance with each of the aforementioned embodiments, in certain embodiments, the aqueous formulation comprises 0.02%-0.04% (w/v) polysorbate 80. In certain embodiments, the aqueous formulation comprises 0.02% (w/v) polysorbate 80. In certain embodiments, the aqueous formulation comprises 0.03% (w/v) polysorbate 80. In certain embodiments, the aqueous formulation comprises 0.04% (w/v) polysorbate 80.

In an embodiment, the aqueous formulation comprises 165 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 150 mg/mL of an isolated FcRn antagonist in 20 mM histidine/histidine HCl, 60 mM sucrose, 100 mM NaCl, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, invention is an aqueous formulation comprising 150 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 175 mg/mL of an isolated FcRn antagonist in 20 mM histidine/histidine HCl, 60 mM sucrose, 100 mM NaCl, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising 175 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 200 mg/mL of an isolated FcRn antagonist in 20 mM histidine/histidine HCl, 60 mM sucrose, 100 mM NaCl, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising 200 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 100-300 mg/mL of an isolated FcRn antagonist in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100-300 mg/mL ARGX-113 in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 100-200 mg/mL of an isolated FcRn antagonist in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100-200 mg/mL ARGX-113 in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 165 mg/mL of an isolated neonatal Fc receptor (FcRn) antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising 165 mg/mL ARGX-113 in 20 mM histidine/histidine HCl, 60 mM sucrose, 100 mM NaCl, 10 mM L-methionine, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 175 mg/mL of an isolated FcRn antagonist in 20 mM histidine/histidine HCl, 60 mM sucrose, 100 mM NaCl, 10 mM L-methionine, and 0.03% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising 175 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 200 mg/mL of an isolated FcRn antagonist in 20 mM histidine/histidine HCl, 60 mM sucrose, 100 mM NaCl, 10 mM L-methionine, and 0.03% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising 200 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of an Fc domain homodimer, wherein the amino acid sequence of each of the Fc domains consists of SEQ ID NO: 1.

An aspect of the invention is an aqueous formulation comprising about 100 to about 300 mg/mL of an isolated FcRn antagonist in 50 mM histidine/histidine HCl, 60 mM sucrose, 150 mM arginine HCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100 to about 300 mg/mL ARGX-113 in 50 mM histidine/histidine HCl, 60 mM sucrose, 150 mM arginine HCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments in accordance with this aspect of the invention, the aqueous formulation comprises 100-300 mg/mL ARGX-113.

In certain embodiments in accordance with this aspect of the invention, the aqueous formulation comprises about 150 to about 200 mg/mL ARGX-113. In certain embodiments in accordance with this aspect of the invention, the aqueous formulation comprises 150-200 mg/mL ARGX-113.

In certain embodiments in accordance with this aspect of the invention, the aqueous formulation comprises about 150 to about 180 mg/mL ARGX-113. In certain embodiments in accordance with this aspect of the invention, the aqueous formulation comprises 150-180 mg/mL ARGX-113.

In accordance with each of the aforementioned embodiments, in certain embodiments, the aqueous formulation comprises 0.02%-0.04% (w/v) polysorbate 20. In certain embodiments, the aqueous formulation comprises 0.02% (w/v) polysorbate 20. In certain embodiments, the aqueous formulation comprises 0.03% (w/v) polysorbate 20. In certain embodiments, the aqueous formulation comprises 0.04% (w/v) polysorbate 20.

An aspect of the invention is an aqueous formulation comprising about 100 to about 200 mg/mL of an isolated FcRn antagonist in 50 mM histidine/histidine HCl, 60 mM sucrose, 150 mM arginine HCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100 to about 200 mg/mL ARGX-113 in 50 mM histidine/histidine HCl, 60 mM sucrose, 150 mM arginine HCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments in accordance with this aspect of the invention, the aqueous formulation comprises 100-300 mg/mL ARGX-113.

In certain embodiments in accordance with this aspect of the invention, the aqueous formulation comprises about 150 to about 200 mg/mL ARGX-113. In certain embodiments in accordance with this aspect of the invention, the aqueous formulation comprises 150-200 mg/mL ARGX-113.

In certain embodiments in accordance with this aspect of the invention, the aqueous formulation comprises about 150 to about 180 mg/mL ARGX-113. In certain embodiments in accordance with this aspect of the invention, the aqueous formulation comprises 150-180 mg/mL ARGX-113.

In accordance with each of the aforementioned embodiments, in certain embodiments, the aqueous formulation comprises 0.02%-0.04% (w/v) polysorbate 20. In certain embodiments, the aqueous formulation comprises 0.02% (w/v) polysorbate 20. In certain embodiments, the aqueous formulation comprises 0.03% (w/v) polysorbate 20. In certain embodiments, the aqueous formulation comprises 0.04% (w/v) polysorbate 20.

Alternatively, in accordance with each of the aforementioned embodiments, in certain embodiments, the aqueous formulation comprises 0.02%-0.04% (w/v) polysorbate 80. In certain embodiments, the aqueous formulation comprises 0.02% (w/v) polysorbate 80. In certain embodiments, the aqueous formulation comprises 0.03% (w/v) polysorbate 80. In certain embodiments, the aqueous formulation comprises 0.04% (w/v) polysorbate 80.

In an embodiment, the aqueous formulation comprises about 150 mg/mL ARGX-113 in 50 mM histidine/histidine HCl, 60 mM sucrose, 150 mM arginine HCl, and 0.04% (w/v) polysorbate 80, pH 6.0.

In an embodiment, the aqueous formulation comprises 150 mg/mL ARGX-113 in 50 mM histidine/histidine HCl, 60 mM sucrose, 150 mM arginine HCl, 10 mM L-methionine, and 0.04% (w/v) polysorbate 80, pH 6.0.

An aspect of the invention is an aqueous formulation comprising about 100-200 mg/mL of an isolated FcRn antagonist in 20 mM histidine/histidine HCl, 60 mM sucrose, 100 mM arginine HCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising about 100-200 mg/mL ARGX-113 in 20 mM histidine/histidine HCl, 60 mM sucrose, 100 mM arginine HCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

An aspect of the invention is an aqueous formulation comprising about 175 mg/mL of an isolated FcRn antagonist in 20 mM histidine/histidine HCl, 60 mM sucrose, 100 mM arginine HCl, 10 mM L-methionine, and 0.03% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the invention is an aqueous formulation comprising 175 mg/mL ARGX-113 in 20 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of an Fc domain homodimer, wherein the amino acid sequence of each of the Fc domains consists of SEQ ID NO: 1.

An aspect of the invention is an aqueous formulation comprising about 200 mg/mL of an isolated FcRn antagonist in 20 mM histidine/histidine HCl, 60 mM sucrose, 100 mM arginine HCl, 10 mM L-methionine, and 0.03% (w/v) polysorbate 20, pH 6.0, wherein the isolated FcRn antagonist consists of a variant Fc region, wherein said variant Fc region consists of an Fc domain homodimer, wherein the amino acid sequence of each of the Fc domains consists of SEQ ID NO: 1, SEQ ID NO: 2, or SEQ ID NO: 3.

In an embodiment, the invention is an aqueous formulation comprising 200 mg/mL ARGX-113 in 20 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of an Fc domain homodimer, wherein the amino acid sequence of each of the Fc domains consists of SEQ ID NO: 1.

An aspect of the invention is an aqueous formulation comprising about 100-300 mg/mL of an isolated neonatal Fc receptor (FcRn) antagonist in 50 mM histidine/histidine HCl, 200 mM arginine HCl, pH 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 200-300 mg/mL of an isolated neonatal Fc receptor (FcRn) antagonist in 50 mM histidine/histidine HCl, 200 mM arginine HCl, pH 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1.

In an embodiment, the aqueous formulation comprises about 250-300 mg/mL of an isolated neonatal Fc receptor (FcRn) antagonist in 50 mM histidine/histidine HCl, 200 mM arginine HCl, pH 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1.

In accordance with each of the foregoing aspects and embodiments, in certain embodiments, the aqueous formulation is substantially free of dissolved oxygen. As used herein, the term "substantially free" refers to at least 95% free. For example, in certain embodiments, the aqueous formulation is at least 95% free of dissolved oxygen. In various certain embodiments, the aqueous formulation is at least 96%, at least 97%, at least 98%, at least 99%, or 100% free of dissolved oxygen. Assuming that water is normally equilibrated with air, which is 20% oxygen, in certain embodiments, the aqueous formulation substantially free of dissolved oxygen comprises less than or equal to 1% dissolved oxygen. In certain embodiments, the aqueous formulation is 100% free of dissolved oxygen.

In accordance with each of the foregoing aspects and embodiments, in certain embodiments, the aqueous formulation is suitable for in vivo use. For example, in such embodiments the aqueous formulation is sterile and free of pharmaceutically unacceptable amounts of toxic materials such as endotoxin. Such aqueous formulations can conform, for example, to Good Manufacturing Process (GMP) quality standards according to regulations promulgated by the U.S. Food and Drug Administration (FDA).

Methods of Making Formulations

Formulations in accordance with the invention can be prepared using any suitable method. Generally, ARGX-113 is prepared from eukaryotic cells comprising an expression vector or nucleic acid sequence encoding the Fc domain. For example, the eukaryotic cells can be Chinese hamster ovary (CHO) cells, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), BFA-1c1BPT (bovine endothelial cells), RAJI (human lymphocyte), 293 (human kidney), or NSO cells. In an embodiment, the eukaryotic cells used to express ARGX-113 are CHO cells. See, for example, WO 2015/100299, the entire contents of which are incorporated herein by reference. ARGX-113 typically is expressed as a secreted protein that can be isolated from the cells using techniques known in the art. Generally, the isolated and unconcentrated protein product is then placed in a sterile aqueous solution such as Tris/Glycine, pH 7.2, or 20 mM L-histidine/L-histidine HCl·H$_2$O, pH 6.0.

This initial product is then up-concentrated and subjected to buffer exchange as appropriate to arrive at a concentrated protein solution comprising ARGX-113 at a concentration equal to or exceeding the target final concentration. For example, the up-concentration and buffer exchange may yield an intermediate product comprising ARGX-113 at about 200 mg/mL in 20 mM L-histidine/L-histidine HCl·H$_2$O, 100 mM NaCl, pH 6.0.

Up-concentration can be performed using any suitable method in the art. Such methods can include, without limitation, tangential flow filtration (TFF), dialysis, ultrafiltration, and lyophilization. For commercial production purposes, TFF may typically be used.

Additional components can then be added to arrive at the desired final formulation. For example, additional components such as NaCl, arginine HCl, sucrose, and/or polysorbate can be added from concentrated stock solutions of each of said additional components, and, if desired, water can be added to arrive at the desired final formulation. In a particular embodiment, polysorbate (PS20) is added as the very last excipient of the formulation so that an accurate pH value is achieved (adding the polysorbate at the end avoids concentrating up because of the molecular weight of the polysorbate together with ARGX-113).

In certain embodiments, the intermediate solution and additional components are degassed or otherwise treated to reduce or eliminate dissolved oxygen. For example, said intermediate solution and components can be equilibrated with argon or nitrogen.

In certain embodiments, the final aqueous formulation is degassed or otherwise treated to reduce or eliminate dissolved oxygen. For example, said final aqueous formulation can be equilibrated with argon or nitrogen by bubbling said gas in the final aqueous formulation for a period of time sufficient to reduce or eliminate dissolved oxygen from the formulation. In certain embodiments, the final aqueous formulation is then stored under a nitrogen atmosphere.

The aqueous formulation so prepared typically will be sterile filtered and then aliquoted and stored in sterile containers or devices as described herein.

Routes of Administration

The aqueous formulations of the invention are suitable for parenteral administration. In certain embodiments, the aqueous formulations of the invention are suitable for subcutaneous administration. In certain embodiments, the aqueous formulations of the invention are suitable for intravenous administration. In certain embodiments, the aqueous formulations of the invention are suitable for intraperitoneal administration.

Effective Amount

The formulations and compositions are generally to be administered in an effective amount. An "effective amount" refers to an amount sufficient to achieve a desired effect. In certain embodiments, an effective amount is a therapeutically effective amount, i.e., an amount sufficient to achieve a desired therapeutic effect in a subject. Examples of desired therapeutic effects include, without limitation, decrease in serum total IgG, and treatment of various antibody-mediated autoimmune diseases such as myasthenia gravis (MG) and immune thrombocytopenia (ITP).

Subject

As used herein, a "subject" refers generally to a mammal. In certain embodiments, a subject is a mammal other than a human or a non-human primate. In certain embodiments, a subject is a human or a non-human primate. In certain embodiments, a subject is a human. In certain embodiments, a subject is an adult human, i.e., a human at least 18 years of age. In certain embodiments, a subject is a human less than 18 years of age.

Pharmaceutical Product

An aspect of the invention is a packaged pharmaceutical product comprising a sterile container comprising a therapeutically effective amount of an aqueous formulation of the invention. In various embodiments, the packaged pharmaceutical product can be presented as a single-use vial, a multi-use vial, or a pre-filled syringe.

Devices

An aspect of the invention is a device comprising a therapeutically effective amount of an aqueous formulation of the invention.

In certain embodiments, the aqueous formulation is an aqueous formulation comprising about 100-200 mg/mL of an isolated FcRn antagonist in 20 mM histidine/histidine HCl, 60 mM sucrose, 100 mM NaCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 150 mg/mL of an isolated FcRn antagonist in 20 mM histidine/histidine HCl, 60 mM sucrose, 100 mM NaCl, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 175 mg/mL isolate FcRn antagonist in 20 mM histidine/histidine HCl, 60 mM sucrose, 100 mM NaCl, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 200 mg/mL of an isolated FcRn antagonist in 20 mM histidine/histidine HCl, 60 mM sucrose, 100 mM NaCl, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 100-300 mg/mL ARGX-113 in 20 mM histidine/histidine HCl, 60 mM sucrose, 100 mM NaCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 100-200 mg/mL ARGX-113 in 20 mM histidine/histidine HCl, 60 mM sucrose, 100 mM NaCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising 150 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising 175 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising 200 mg/mL ARGX-113 in 20 mM histidine/histidine HCl, 60 mM sucrose, 100 mM NaCl, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 100-300 mg/mL of an isolated FcRn antagonist in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 150 mg/mL of an isolated FcRn antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 165 mg/mL isolate FcRn antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 175 mg/mL isolate FcRn antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 180 mg/mL isolate FcRn antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 200 mg/mL of an isolated FcRn antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 300 mg/mL of an isolated FcRn antagonist in 20 mM histidine/histidine HCl, 60 mM sucrose, 100 mM NaCl, 10 mM L-methionine, and 0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 100-300 mg/mL ARGX-113 in 20 mM histidine/histidine HCl, 60 mM sucrose, 100 mM NaCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising 150 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 165 mg/mL ARGX-113 in 20 mM histidine/histidine HCl, 60 mM sucrose, 100 mM NaCl, 10 mM L-methionine, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 165 mg/mL of an isolated FcRn antagonist in 20 mM histidine/histidine HCl, 60 mM sucrose, 100 mM NaCl, 10 mM L-methionine, and 0.04% (w/v) polysorbate 20, pH 6.0, wherein isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising 165 mg/mL ARGX-113 in 20 mM histidine/histidine HCl, 60 mM sucrose, 100 mM NaCl, 10 mM L-methionine, and 0.04% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising 175 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising 200 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 100 to about 200 mg/mL of an isolated FcRn antagonist in 50 mM histidine/histidine HCl, 60 mM sucrose, 150 mM arginine HCl, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 100 to about 200 mg/mL ARGX-113 in 50 mM histidine/histidine HCl, 60 mM sucrose, 150 mM arginine HCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 100 to about 200 mg/mL of an isolated FcRn antagonist in 50 mM histidine/histidine HCl, 60 mM sucrose, 100 mM arginine HCl, 10 mM L-methionine, and 0.02%-0.04% (w/v) polysorbate 20 or polysorbate 80, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 150 mg/mL of an isolated FcRn antagonist in 50 mM histidine/histidine HCl, 60 mM sucrose, 100 mM arginine HCl, 10 mM L-methionine, and 0.02%-0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 175 mg/mL of an isolated FcRn antagonist in 50 mM histidine/histidine HCl, 60 mM sucrose, 100 mM arginine HCl, 10 mM L-methionine, and 0.02%-0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 200 mg/mL of an isolated FcRn antagonist in 50 mM histidine/histidine HCl, 60 mM sucrose, 100 mM arginine HCl, 10 mM L-methionine, and 0.02%-0.04% (w/v) polysorbate 20, pH 6.0, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In certain embodiments, the aqueous formulation is an aqueous formulation comprising about 100 to about 200 mg/mL ARGX-113 in 50 mM histidine/histidine HCl, 60 mM sucrose, 100 mM arginine HCl, 10 mM L-methionine, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 150 mg/mL ARGX-113 in 50 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 175 mg/mL ARGX-113 in 50 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 200 mg/mL ARGX-113 in 50 mM histidine/histidine HCl, 60 mM sucrose, 100 mM arginine HCl, 10 mM L-methionine, and 0.03% (w/v) polysorbate 20, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

In certain embodiments, the aqueous formulation is an aqueous formulation comprising about 100-300 mg/mL of an isolated neonatal Fc receptor (FcRn) antagonist in 50 mM histidine/histidine HCl, 200 mM arginine HCl, pH 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1, SEQ ID NO: 2, or SEQ ID NO: 3.

In an embodiment, the aqueous formulation comprises about 200-300 mg/mL of an isolated neonatal Fc receptor (FcRn) antagonist in 50 mM histidine/histidine HCl, 200 mM arginine HCl, pH 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1.

In an embodiment, the aqueous formulation comprises about 250-300 mg/mL of an isolated neonatal Fc receptor (FcRn) antagonist in 50 mM histidine/histidine HCl, 200 mM arginine HCl, pH 6.5, wherein the isolated FcRn antagonist consists of a variant Fc region, wherein said variant Fc region consists of two Fc domains which form a homodimer, wherein the amino acid sequence of each of the Fc domains consists of SEQ ID NO: 1.

In accordance with each of the foregoing embodiments of this aspect, in certain embodiments, the device comprises about 1 to about 2.5 mL of the aqueous formulation. In accordance with each of the foregoing embodiments of this aspect, in certain embodiments, the device comprises 1 to 2.5 mL of the aqueous formulation.

In certain embodiments, the device comprises a syringe comprising the aqueous formulation. Such syringe optionally can be fitted with a needle suitable for administering at least a portion of the aqueous solution contained within the syringe to a subject. Fine gauge needles (small diameter) offer less pain for the patient but require low viscosity medications. The needle gauge is preferably 27 gauge or higher (i.e, smaller diameter). The outer diameter of the needle may be 0.413 mm, 0.41 mm, or smaller.

In certain embodiments, the syringe is presented as a pre-filled syringe. Such pre-filled syringe can be suitable for single use or, alternatively, for multiple (two or more) uses. Such pre-filled syringe optionally can be fitted with a needle suitable for administering at least a portion of the aqueous solution contained within the pre-filled syringe to a subject. In certain embodiments, the pre-filled syringe is presented in a single-unit package.

In certain embodiments, the pre-filled syringe is substantially free of atmospheric air. That is, in such embodiments the aqueous formulation contained within the pre-filled syringe is substantially free of dissolved oxygen. For example, the aqueous formulation contained within the pre-filled syringe can be prepared with nitrogen as described herein and then placed within a syringe and sealed under a nitrogen atmosphere so as to exclude atmospheric air. In certain such embodiments, the pre-filled syringe can be presented in a gas-impermeable package.

In a particular embodiment, the invention is a pre-filled syringe filled with 2 mL or 2.1 mL of the aqueous formulation as described herein, e.g. comprising 360 mg/2 mL (=180 mg/mL) or 330 mg/2 mL (=165 mg/mL) of an isolated neonatal Fc receptor (FcRn) antagonist such as ARGX-113. Alternatively, the invention is a vial filled with 2.2 mL of the aqueous formulation as described herein, e.g. comprising 360 mg/2.2 mL (=165 mg/mL) of an isolated neonatal Fc receptor (FcRn) antagonist such as ARGX-113. Such a vial can be together in a kit with a needle suitable for administering at least a portion of the aqueous solution contained within the vial to a subject.

The instant invention further contemplates additional devices comprising 2 mL, 2.1 mL, 2.2 mL or more than about 2.5 mL of an aqueous formulation in accordance with the invention. Such devices can comprise, for example and without limitation, about 1.8 mL, 2 mL, 2.1 mL, 2.2 mL, 2.4 mL, 2.6 mL, 2.8 mL, 3 mL, 5 mL, about 10 mL, about 20 mL, about 50 mL, and about 100 mL of an aqueous formulation in accordance with the invention. This has the advantage that the formulation can be administered in one go (one shot) by the patient him/herself as a subcutaneous injection e.g. by using a pre-filled syringe with 2 mL, 2.1 mL, 2.2 mL or 5 mL aqueous formulation according to the invention. Such a "push" subcutaneous administration takes about 12 to 20 seconds or up to 1 minute. As a comparison: an infusion by a nurse or caregiver to a subject may take from a few minutes to a few hours; an IV (intravenous) infusion of an ARGX-113 formulation takes about 60 minutes. Pre-filled syringes provide advantages for patients as it can be used as a subcutaneous injection maintenance dose via self-administration.

The present invention is further illustrated by the following examples, which should not be construed as further limiting. The contents of Sequence Listing, figures, and all references, patents, and published patent applications cited throughout this application are expressly incorporated herein by reference.

EXAMPLES

Example 1. Rheological Characterization

This example describes experiments that were undertaken to develop and characterize high-concentration formulations of ARGX-113. In particular, a goal of this set of experiments was to identify a concentration-viscosity relationship. Studies were performed at two temperatures, 5° C. and 25° C. Five concentrations of ARGX-113 at optimal shear rate were screened to identify rheological profile of ARGX-113 in platform buffer.

Starting with ARGX-113 4-5 mg/mL in Tris/glycine buffer pH 7.2, ARGX-113 buffer was exchanged and up-concentrated to maximum possible concentration (targeted 250 mg/mL) in in sodium phosphate at pH 6.7+Salt and, separately, in histidine HCl (HisHCl)+Salt at pH 6.0. Concentration and pH were monitored during the processing. Viscoelastic behavior was studied at highest concentration in HisHCl at pH 6.0+Salt by shear rate ramping from 0-4000 $s^{-1}$. Serial dilutions were performed (6 concentrations) and verified with UV-absorbance measurement ($A_{280}$). Viscosity vs concentration measurements were performed at a shear rate of 2000 $s^{-1}$.

ARGX-113 in sodium phosphate pH 6.7+Salt precipitated out of solution at ~130 mg/mL.

ARGX-113 up-concentration processing in sodium phosphate at pH 6.7+Salt was very slow. ARGX-113 at high concentration (~130 mg/mL) in sodium phosphate at pH 6.7+Salt showed reversible solid/liquid phase transition depending on the storage condition (5° C. versus 25° C.). ARGX-113 at high concentration (~130 mg/mL) in sodium phosphate at pH 6.7+Salt showed very high number and size of visible particles at 5° C.

In contrast, ARGX-113 in HisHCl+Salt at pH 6.0 remained in solution up to at least ~260 mg/mL.

ARGX-113 up-concentration processing in HisHCl+Salt at pH 6.0 was rapid.

No precipitation or phase separation was prominently visible during the up-concentration as in contrast with sodium phosphate buffer+Salt.

Concentration-dependent sol-gel transition was observed after storage at 5° C. HisHCl formulations appeared very jelly at ~260 mg/mL concentration (260>200>>120 mg/mL) which quickly converted into liquid upon warming to room temperature or pipetting.

ARGX-113 seems to have some thixotropic behavior in HisHCl+Salt at pH 6.0 at very high concentration and low temperature (>180 mg/mL, 5° C.).

Shear thinning/thickening behavior of ARGX-113 at highest concentration (267 mg/mL in HisHCl+Salt at pH 6.0 at 25° C.) was studied by shear rate ramping from 0-4000 $s^{-1}$. Representative results are shown in FIG. 1. As shown in the figure, ARGX-113 did not show any significant shear thickening or thinning in the range of 1000-4000 $s^{-1}$. 2000 $s^{-1}$ was chosen as the shear rate for additional studies.

Figure 2:
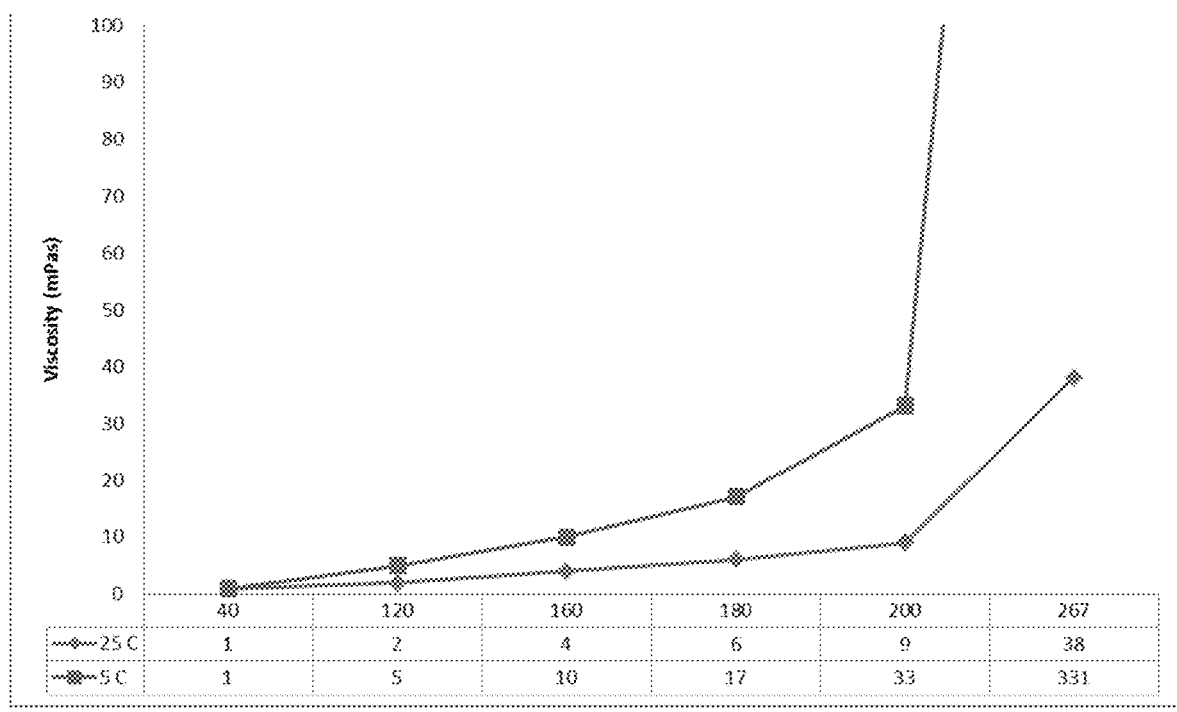
FIG. 2 depicts concentration (mg/mL) versus viscosity (mPa·s) of ARGX-113 in HisHCl+Salt at the indicated concentrations and temperatures (° C.).

Representative results from study of concentration of ARGX-113 in HisHCl+Salt at pH 6.0 versus viscosity are shown in FIG. 2. As shown in the figure, viscosity at about 180 mg/mL at 5° C. and 25° C. were 6 and 17 mPa·s, respectively, and viscosity at about 200 mg/mL at 5° C. and 25° C. were 9 and 33 mPa·s, respectively.

Additional studies were undertaken to evaluate a variety of excipients and pH values for up-concentrated solutions of ARGX-113. Starting with ARGX-113 4-5 mg/mL in Tris/glycine buffer pH 7.2, ARGX-113 buffer was exchanged and up-concentrated in sodium phosphate+Salt at pH 6.7 and, separately, in HisHCl+Salt at pH 6.0 to a target concentration of 175 mg/mL. Concentration and pH were monitored during the processing. Stock solutions of different excipients were prepared to achieve various target formulation compositions. Eleven (11) formulation conditions with different excipients and pH were studied for viscosity lowering assessment at high concentration of 175 mg/mL. The various formulations studied are shown in Table 1.

TABLE 1

| ID | Buffer | pH | Excipient 1 | Excipient 2 | Excipient 3 |
|---|---|---|---|---|---|
| F1 | 20 mM HisHCl | 6.0 | 150 mM NaCl | — | — |
| F2 | 50 mM HisHCl | 6.0 | 150 mM ArgHCl | — | — |
| F3 | 20 mM HisHCl | 6.0 | 100 mM NaCl | 50 mM ArgHCl | — |
| F4 | 20 mM HisHCl | 6.0 | 50 mM NaCl | 50 mM ArgHCl | 75 mM Sucrose |
| F5 | 20 mM HisHCl | 6.0 | 50 mM NaCl | 100 mM ArgHCl | — |
| F6 | 20 mM HisHCl | 6.0 | 100 mM NaCl | 75 mM Sucrose | — |
| F7 | 20 mM HisHCl | 6.0 | 50 mM NaCl | 50 mM ArgHCl | — |
| F8 | 20 mM HisHCl | 6.0 | 50 mM NaCl | 150 mM Sucrose | — |
| F9 | 20 mM HisHCl | 6.5 | 150 mM NaCl | — | — |
| F10 | 20 mM HisHCl | 5.5 | 150 mM NaCl | — | — |
| F11 | 25 mM SodPhos | 6.7 | 100 mM NaCl | 150 mM ArgHCl | — |

ArgHCl: arginine HCl
SodPhos: sodium phosphate

Phosphate formulation was not able to formulate above 100 mg/mL due to significant precipitation. All formulations were stored at 5° C. for about 48 hours to observe phase transition if any. Viscosity measurements for all 11 formulations were performed at shear rate of 2000 $s^{-1}$ at 5° C. and selective formulation at 25° C.

All formulations except stock remained liquid and clear on storage at 5° C. even after two days. F11 (SodPhos+NaCl) became turbid and showed precipitation on up-concentration to ~129 mg/mL. Phosphate formulation formed a clear solution after compounding and storage at 5° C. F9 (pH 6.5) formulation was slightly opaque which further became slightly clear at 5° C.

Viscosity was low (<25 mPa·s) at 5° C. in all formulations F1-F11. F2 and F5 showed effective lowering in viscosity. Sucrose increased viscosity at 175 mg/mL, in 20 mM His/HisHCl, pH 6.0 (F6 and F8).

Example 2. Further Rheological Characterization

This example describes experiments that were undertaken to develop and characterize further candidate high-concentration formulations of ARGX-113. In particular, a goal of this set of experiments was to identify a candidate high-concentration liquid formulation of ARGX-113 for pre-clinical toxicology and early phase clinical studies based on certain characteristics and short-term stability studies.

The compositions of four aqueous formulations of ARGX-113 studied in this example are shown in Table 2.

TABLE 2

| ID | ARGX-113 | Buffer | pH | Excipient 1 | Excipient 2 | Excipient 3 |
|---|---|---|---|---|---|---|
| F12 | 150 mg/mL | 50 mM HisHCl | 6.0 | — | 150 mM ArgHCl | 0.04% w/v PS80 |
| F13 | 150 mg/mL | 20 mM HisHCl | 6.0 | 100 mM NaCl | 60 mM Sucrose | 0.04% w/v PS20 |
| F14 | 100 mg/mL | 20 mM HisHCl | 6.5 | 75 mM NaCl | 100 mM Sucrose | 0.04% w/v PS20 |
| F15 | 100 mg/mL | 20 mM HisHCl | 6.0 | 75 mM NaCl | 100 mM Sucrose | 0.04% w/v PS20 |

PS20: polysorbate 20
PS80: polysorbate 80

Starting with ARGX-113~136 mg/mL in 20 mM L-histidine/L-histidine HCl·H$_2$O, ARGX-113 buffer was exchanged to achieve target buffer concentration and pH, followed by up-concentration above the target concentrations shown in Table 2. F14 was prepared as 100 mg/mL concentration due to the solidification of material during the up-concentration which restricted the formulation concentration to 100 mg/mL after compounding using stock solutions.

Initial characterization of these formulations included determination of pH, osmolality by freezing point depression, and actual protein concentration. Representative results are shown in Table 3.

TABLE 3

| | Formulation | | | |
|---|---|---|---|---|
| Test | F12 | F13 | F14 | F15 |
| pH | 6.0 | 6.1 | 6.4 | 6.0 |
| Osmolality (mOsmol/kg) | 367 | 322 | 385 | 395 |
| Protein Concentration (mg/mL) | 160.1 | 153.4 | 99.2 | 101.7 |

An aliquot of each formulation was subjected in horizontal position to shake stress during approximately 7 days at room temperature and cool temperature conditions in an orbital shaker at a target speed of 115 rpm.

An aliquot of each formulation was subjected in vertical position to five freeze/thaw cycles from −65° C. or below to room temperature.

Figure 3:
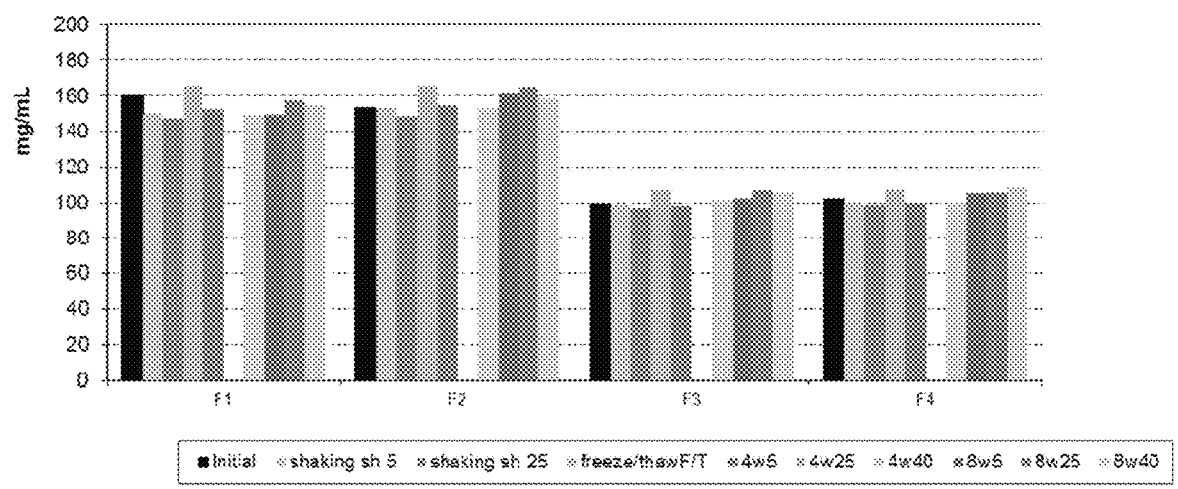
FIG. 3 depicts protein concentration as measured by UV/Vis of ARGX-113 formulations described in Example 2. sh5, shaking at 5° C.; sh25, shaking at 25° C.; 4w5, 4 weeks at 5° C.; 4w25, 4 weeks at 25° C.; 4w40, 4 weeks at 40° C.; 8w5, 8 weeks at 5° C.; 8w25, 8 weeks at 25° C.; 4w40, 8 weeks at 40° C.

As shown in FIG. 3, ARGX-113 concentration was stable under all conditions tested. In FIG. 3: F1=F12; F2=F13; F3=F14; F4=F15. The bars shown in the order from left to right in FIG. 3 are the following: F1 initial; F1 shaking at 5° C. (shaking sh 5); F1 shaking at 25° C. (shaking sh 25); F1 5 cycles of freeze/thaw stress (freeze/thawF/T); F1 4 weeks at 5° C. (4W5); F1 4 weeks at 25° C. (4W25); F1 4 weeks at 40° C. (4W40); F1 8 weeks at 5° C. (8w5); F1 8 weeks at 25° C. (8w25); F1 8 weeks at 40° C. (8w40); F2 initial; F2 shaking at 5° C. (shaking sh 5); F2 shaking at 25° C.

(shaking sh 25); F2 5 cycles of freeze/thaw stress (freeze/thawF/T); F2 4 weeks at 5° C. (4W5); F2 4 weeks at 25° C. (4W25); F2 4 weeks at 40° C. (4W40); F2 8 weeks at 5° C. (8w5); F2 8 weeks at 25° C. (8w25); F2 8 weeks at 40° C. (8w40); F3 initial; F3 shaking at 5° C. (shaking sh 5); F3 shaking at 25° C. (shaking sh 25); F3 5 cycles of freeze/thaw stress (freeze/thawF/T); F3 4 weeks at 5° C. (4W5); F3 4 weeks at 25° C. (4W25); F3 4 weeks at 40° C. (4W40); F3 8 weeks at 5° C. (8w5); F3 8 weeks at 25° C. (8w25); F3 8 weeks at 40° C. (8w40); F4 initial; F4 shaking at 5° C. (shaking sh 5); F4 shaking at 25° C. (shaking sh 25); F4 5 cycles of freeze/thaw stress (freeze/thawF/T); F4 4 weeks at 5° C. (4W5); F4 4 weeks at 25° C. (4W25); F4 4 weeks at 40° C. (4W40); F4 8 weeks at 5° C. (8w5); F4 8 weeks at 25° C. (8w25); F4 8 weeks at 40° C. (8w40).

Figure 4A:
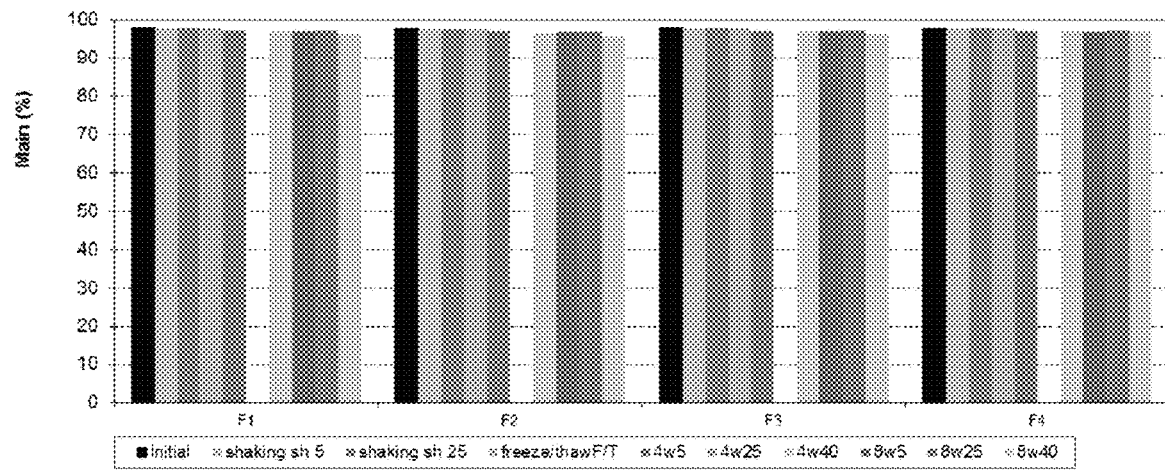
FIGS. 4A and 4B depict size exclusion chromatography (SEC) results for the main peak and high molecular weight (HMW) species, respectively, of ARGX-113 formulations described in Example 2. sh5, shaking at 5° C.; sh25, shaking at 25° C.; 4w5, 4 weeks at 5° C.; 4w25, 4 weeks at 25° C.; 4w40, 4 weeks at 40° C.; 8w5, 8 weeks at 5° C.; 8w25, 8 weeks at 25° C.; 4w40, 8 weeks at 40° C.
Figure 4B:
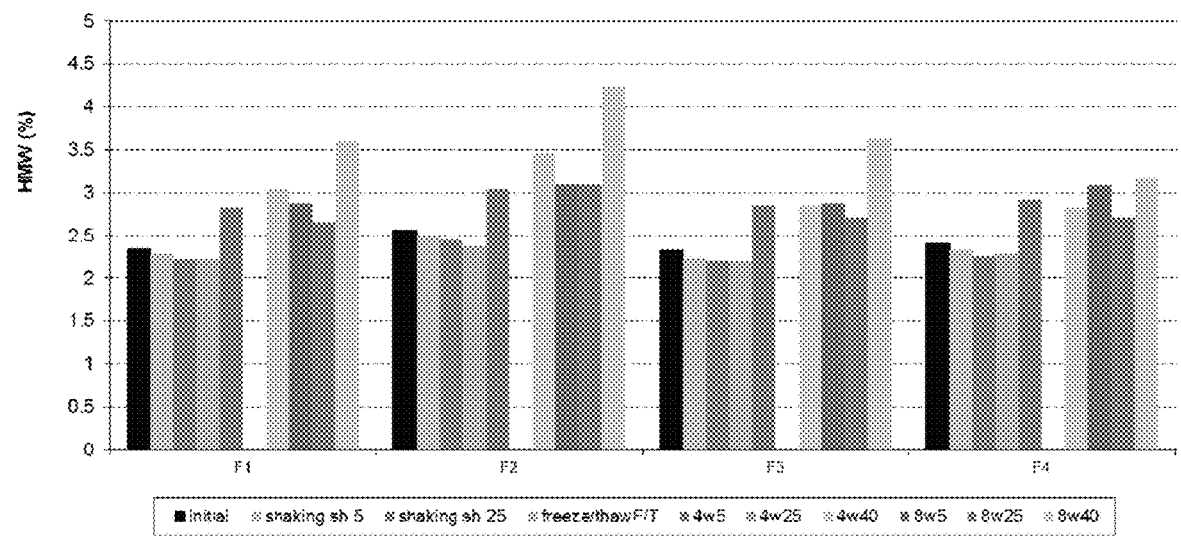
Figure 5A:
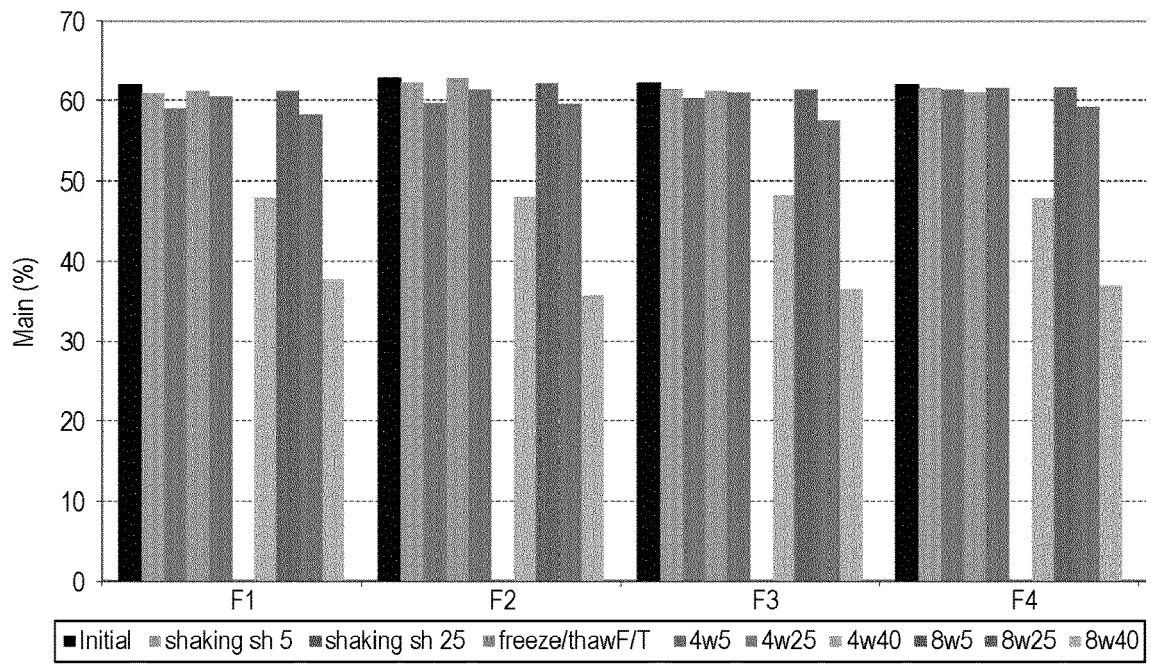
FIGS. 5A-5C depict chemical degradation as determined by iCE for the main peak, acidic variants, and basic variants, respectively, of ARGX-113 formulations described in Example 2. sh5, shaking at 5° C.; sh25, shaking at 25° C.; 4w5, 4 weeks at 5° C.; 4w25, 4 weeks at 25° C.; 4w40, 4 weeks at 40° C.; 8w5, 8 weeks at 5° C.; 8w25, 8 weeks at 25° C.; 4w40, 8 weeks at 40° C.
Figure 5B:
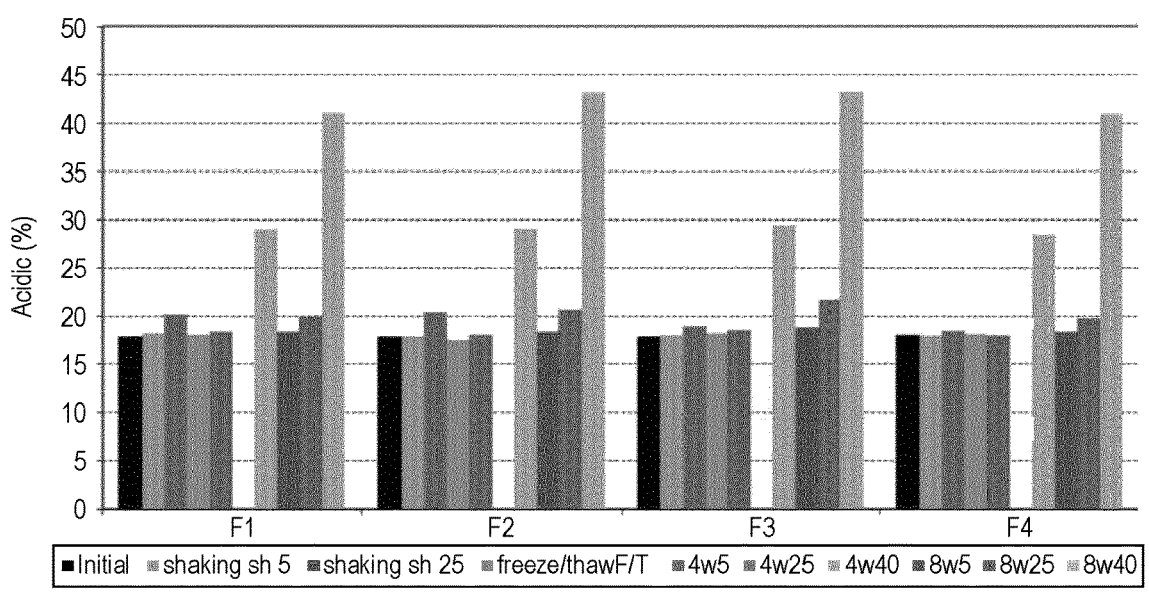
Figure 5C:
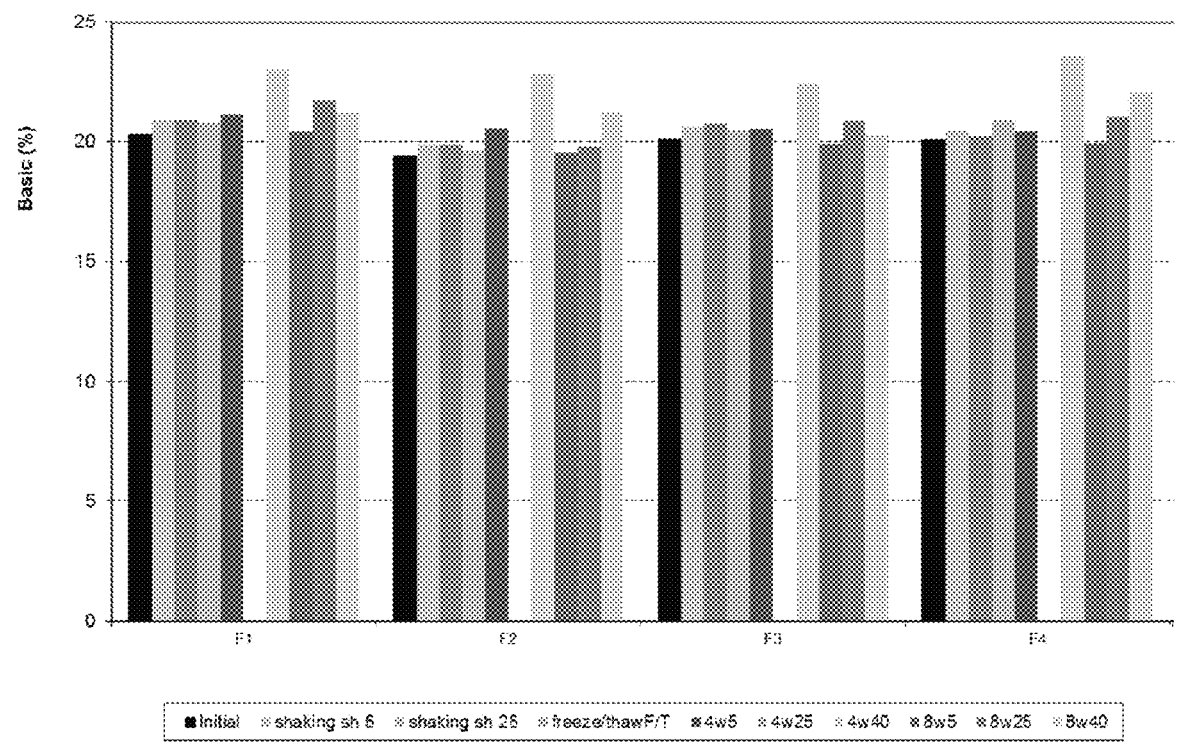
Figure 6A:
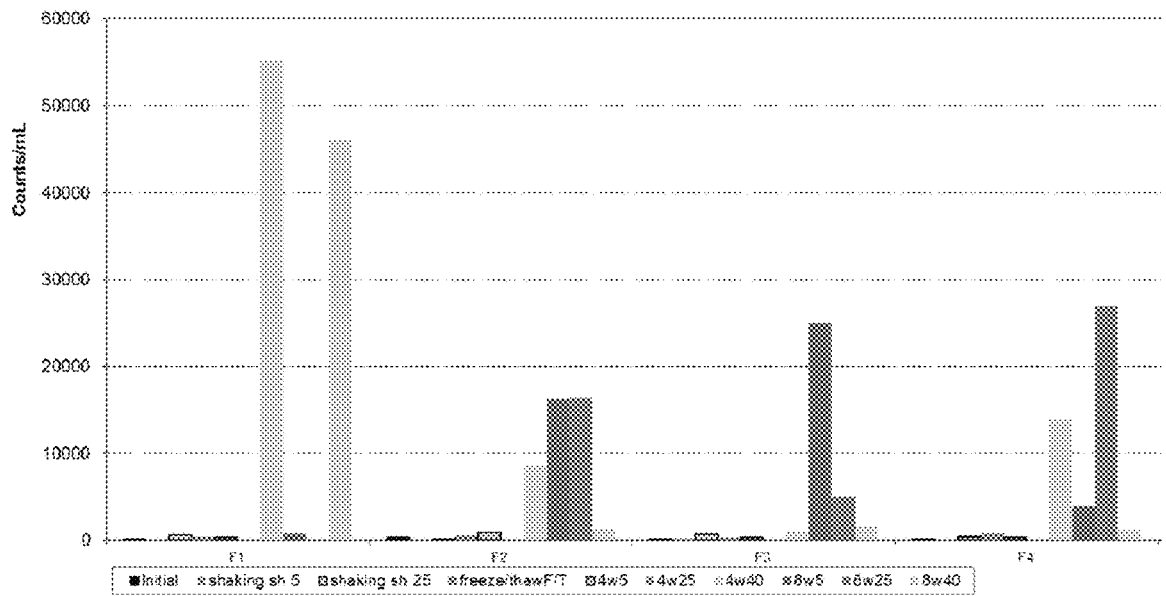
FIGS. 6A-6D depict subvisible particles ≥2 µm, ≥5 µm, ≥10 µm, and ≥25 µm in diameter, respectively, of ARGX-113 formulations described in Example 2. sh5, shaking at 5° C.; sh25, shaking at 25° C.; 4w5, 4 weeks at 5° C.; 4w25, 4 weeks at 25° C.; 4w40, 4 weeks at 40° C.; 8w5, 8 weeks at 5° C.; 8w25, 8 weeks at 25° C.; 4w40, 8 weeks at 40° C.
Figure 6B:
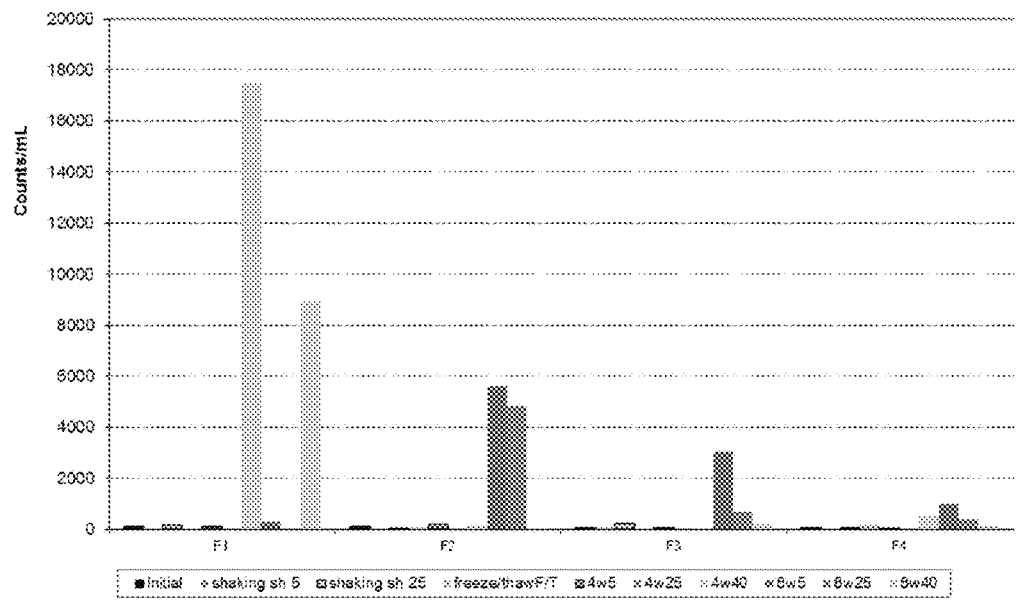
Figure 6C:
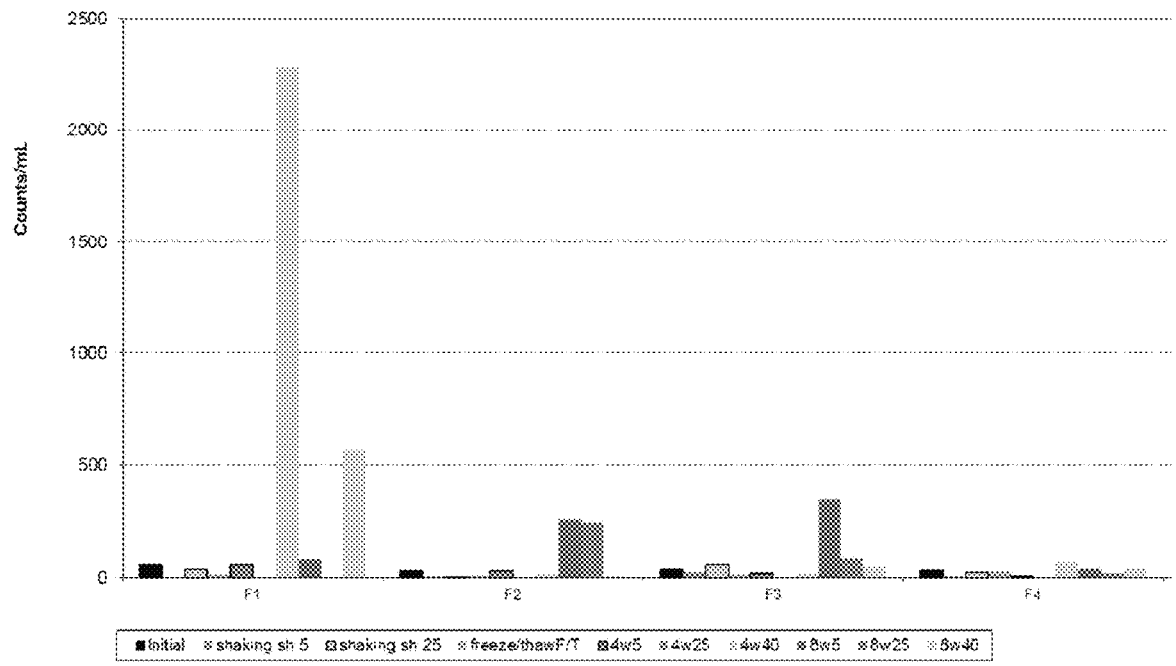
Figure 6D:
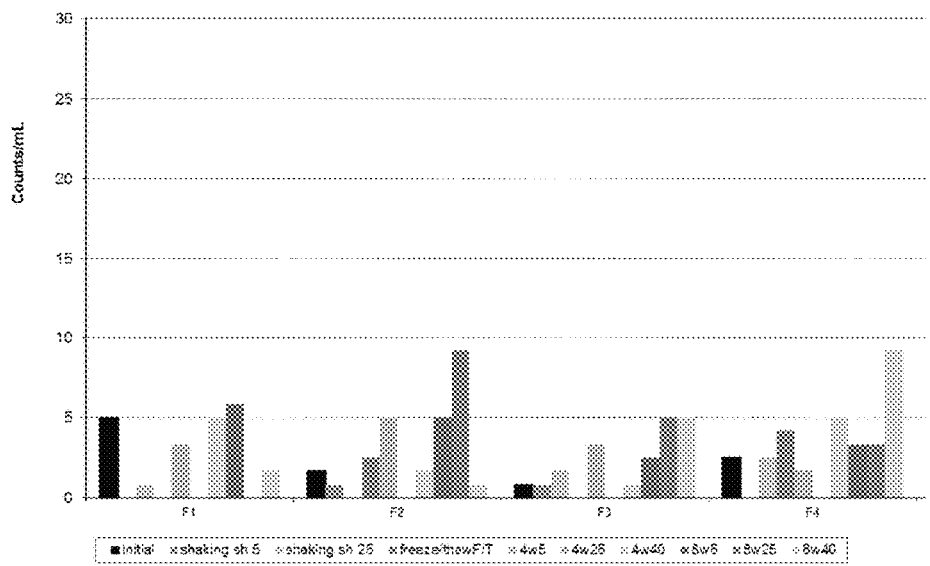

As shown in FIGS. 4A-4B, for all liquid formulations tested, no major differences were observed in aggregation and fragmentation by size exclusion chromatography (SEC). Also, as shown in FIGS. 5A-5C, no major chemical degradation was observed by integrated chip-based capillary electrophoresis (iCE). As shown in FIGS. 6A-6D, overall visible and subvisible particle counts were low on shaking and freeze/thaw stress. This data suggested no significant differences between polysorbate 20 and 80 formulations and both polysorbate 20 and polysorbate 80, at 0.04% w/v, equally protected ARGX-113 against agitation and freeze/thaw stress. In FIGS. 4A-4B, 5A-5C and 6A-6D: F1=F12; F2=F13; F3=F14; F4=F15. The bars shown in the order from left to right in FIGS. 4A-4B, 5A-5C and 6A-6D are the following: F1 initial; F1 shaking at 5° C. (shaking sh 5); F1 shaking at 25° C. (shaking sh 25); F1 5 cycles of freeze/thaw stress (freeze/thawF/T); F1 4 weeks at 5° C. (4W5); F1 4 weeks at 25° C. (4W25); F1 4 weeks at 40° C. (4W40); F1 8 weeks at 5° C. (8w5); F1 8 weeks at 25° C. (8w25); F1 8 weeks at 40° C. (8w40); F2 initial; F2 shaking at 5° C. (shaking sh 5); F2 shaking at 25° C. (shaking sh 25); F2 5 cycles of freeze/thaw stress (freeze/thawF/T); F2 4 weeks at 5° C. (4W5); F2 4 weeks at 25° C. (4W25); F2 4 weeks at 40° C. (4W40); F2 8 weeks at 5° C. (8w5); F2 8 weeks at 25° C. (8w25); F2 8 weeks at 40° C. (8w40); F3 initial; F3 shaking at 5° C. (shaking sh 5); F3 shaking at 25° C. (shaking sh 25); F3 5 cycles of freeze/thaw stress (freeze/thawF/T); F3 4 weeks at 5° C. (4W5); F3 4 weeks at 25° C. (4W25); F3 4 weeks at 40° C. (4W40); F3 8 weeks at 5° C. (8w5); F3 8 weeks at 25° C. (8w25); F3 8 weeks at 40° C. (8w40); F4 initial; F4 shaking at 5° C. (shaking sh 5); F4 shaking at 25° C. (shaking sh 25); F4 5 cycles of freeze/thaw stress (freeze/thawF/T); F4 4 weeks at 5° C. (4W5); F4 4 weeks at 25° C. (4W25); F4 4 weeks at 40° C. (4W40); F4 8 weeks at 5° C. (8w5); F4 8 weeks at 25° C. (8w25); F4 8 weeks at 40° C. (8w40).

Short-term stability data up to 2 months (8 weeks) suggested that ARGX-113 has moderate aggregation tendency with 0.8-1.7% area increase in aggregation after 8 weeks at 40° C. in SEC. Aggregation rate of ARGX-113 was dependent upon the concentration, pH, and composition at specific storage condition. F13 formulation with NaCl showed higher aggregation compared to F12 with Arginine at 40° C. F14 formulation at pH 6.5 showed higher aggregation compared to F15 at pH 6.0 at 100 mg/mL concentration at 40° C. This data suggested that ARGX-113 has better stability at pH 6.0 compared to pH 6.5. Fragmentation was below the limit of quantification (LOQ) in SEC.

In iCE, ARGX-113 showed high basic and acidic species with low main peak at initial which was rapidly decreased on stability depending upon the pH and composition, especially at elevated temperatures. The iCE profile suggested that the main peak of ARGX-113 in liquid formulations was mainly converted into acidic variants (~24%) at 40° C. on 8 weeks stability. ARGX-113 at 100 mg/mL and 150 mg/mL did not show major differences in the rate and extent of chemical degradation in liquid formulations on 2 month stability. No major changes in basic peaks were observed for all studied formulations and stability time points.

Also, CE-SDS (Caliper, PerkinElmer) did not show any major changes over the 8 week stability study (results not shown).

All formulations were free of visible particles initially and after 8 weeks at 5, 25 and 40° C. except F12 formulation which showed many particles (particle cloud) after 8 weeks at 40° C. Color of solutions varied from slightly brownish to brown depending on storage and formulation conditions, and all formulations showed stable target pH (±0.2) at initial and after 8 weeks at 5, 25 and 40° C.

Figure 7:
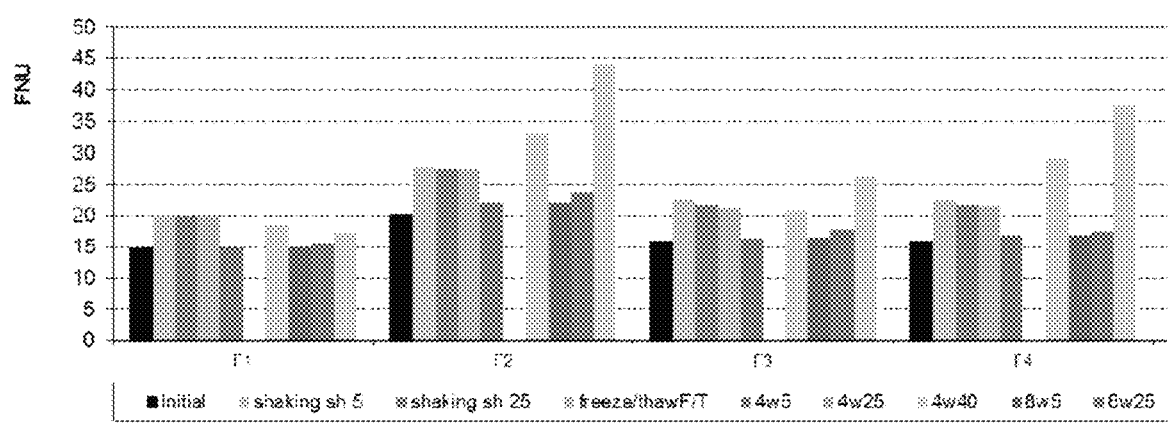
FIG. 7 depicts turbidity of ARGX-113 formulations described in Example 2.

As shown in FIG. 7, overall turbidity of formulations at 150 mg/mL was higher than 15 FNU (formazin nephelometric turbidity units). Furthermore, sodium chloride formulations showed higher turbidity compared to arginine-containing formulations. F13 showed noticeable increase in turbidity after 4 and 8 weeks at 40° C. In FIG. 7: F1=F12; F2=F13; F3=F14; F4=F15. The bars shown in the order from left to right in FIG. 7 are the following: F1 initial; F1 shaking at 5° C. (shaking sh 5); F1 shaking at 25° C. (shaking sh 25); F1 5 cycles of freeze/thaw stress (freeze/thawF/T); F1 4 weeks at 5° C. (4W5); F1 4 weeks at 25° C. (4W25); F1 4 weeks at 40° C. (4W40); F1 8 weeks at 5° C. (8w5); F1 8 weeks at 25° C. (8w25); F2 initial; F2 shaking at 5° C. (shaking sh 5); F2 shaking at 25° C. (shaking sh 25); F2 5 cycles of freeze/thaw stress (freeze/thawF/T); F2 4 weeks at 5° C. (4W5); F2 4 weeks at 25° C. (4W25); F2 4 weeks at 40° C. (4W40); F2 8 weeks at 5° C. (8w5); F2 8 weeks at 25° C. (8w25); F3 initial; F3 shaking at 5° C. (shaking sh 5); F3 shaking at 25° C. (shaking sh 25); F3 5 cycles of freeze/thaw stress (freeze/thawF/T); F3 4 weeks at 5° C. (4W5); F3 4 weeks at 25° C. (4W25); F3 4 weeks at 40° C. (4W40); F3 8 weeks at 5° C. (8w5); F3 8 weeks at 25° C. (8w25); F4 initial; F4 shaking at 5° C. (shaking sh 5); F4 shaking at 25° C. (shaking sh 25); F4 5 cycles of freeze/thaw stress (freeze/thawF/T); F4 4 weeks at 5° C. (4W5); F4 4 weeks at 25° C. (4W25); F4 4 weeks at 40° C. (4W40); F4 8 weeks at 5° C. (8w5); F4 8 weeks at 25° C. (8w25).

From the results obtained in this example, it was concluded that (i) formulation containing NaCl showed higher turbidity than formulation containing arginine, and turbidity increase was higher in NaCl formulation at 150 mg/mL concentration at 40° C.; (ii) overall subvisible particle count was noticeable over the 8-week stability study, except F12 showed increased visible and subvisible particles at 40° C.; (iii) initial levels of aggregates were high, but rate of increase of aggregates was moderate after 8 weeks at 40° C.; (iv) arginine formulation showed lower aggregation on 8 weeks stability compared to NaCl formulation; (v) ARGX-113 showed good physical stability at 150 and 100 mg/mL concentrations, however, physical stability at 100 mg/mL concentration was slightly higher compared to 150 mg/mL formulation at pH 6.0; (vi) initial levels of charged variants were high, and the main peak was mainly getting into the acidic variants in all liquid formulations. Formulation with pH 6.5 showed slightly higher formation of acidic variants compared to formulation with pH 6.0; and (vii) polysorbate 20 and polysorbate 80 at 0.04% w/v concentration were equally effective to protect ARGX-113 against agitation and freeze-thaw stresses.

Example 3. pH and Surfactant Optimization

This example describes additional experiments that were undertaken to develop and characterize further candidate high-concentration formulations of ARGX-113. In particular, a goal of this set of experiments was to identify a candidate high-concentration liquid formulation of ARGX- 113 for pre-clinical toxicology and early phase clinical studies based on certain characteristics and short-term stability studies.

The compositions of seven aqueous formulations of ARGX-113 studied in this example are shown in Table 4.

TABLE 4

| ID | ARGX-113 | Buffer | pH | Excipient 1 | Excipient 2 | Surfactant |
|---|---|---|---|---|---|---|
| F13 | 150 mg/mL | 20 mM HisHCl | 6.0 | 100 mM NaCl | 60 mM Sucrose | 0.04% w/v PS20 |
| F16 | 175 mg/mL | 20 mM HisHCl | 6.0 | 100 mM NaCl | 60 mM Sucrose | 0.04% w/v PS20 |
| F17 | 200 mg/mL | 20 mM HisHCl | 6.0 | 100 mM NaCl | 60 mM Sucrose | 0.04% w/v PS20 |
| F18 | 175 mg/mL | 20 mM HisHCl | 6.0 | 100 mM NaCl | 60 mM Sucrose | 0.02% w/v PS20 |
| F19 | 175 mg/mL | 20 mM HisHCl | 6.0 | 100 mM NaCl | 60 mM Sucrose | 0.02% w/v PS80 |
| F20 | 175 mg/mL | 20 mM HisHCl | 6.0 | 100 mM NaCl | 60 mM Sucrose | 0.05% w/v PS80 |
| F21 | 175 mg/mL | 20 mM HisHCl | 6.0 | 100 mM NaCl | 60 mM Sucrose | 0.04% w/v PX188 |

PS20: polysorbate 20
PS80: polysorbate 80
PX188: poloxamer 188

Experiments were performed on each of the formulations to study 2-week stability at 5° C., 25° C., and 40° C., 1-week shaking stress at 5° C., 1-week shaking stress at 25° C. and 5 cycles of freeze/thaw stress.

Buffer exchange and up-concentration were performed in 20 mM HisHCl, 100 mM NaCl at selected pH, followed immediately by addition of appropriate amounts of sucrose and surfactant stocks to achieve target concentrations. Formulations were stored at 5° C. overnight to observe for any phase transition. Phase separation was observed in F17 (200 mg/mL), but it returned to liquid phase after room temperature equilibration. The various formulations were then filtered and placed in separate vials.

Following 1-week storage at 5° C., and similarly after 5-day agitation at 5° C., reversible solid-liquid phase transition was observed in F17, F18 and F19 samples. Upon warming/equilibration to room temperature, formulations returned to clear liquid solution. The other formulations (F12, F16, F20, and F21) did not show visible solidification/phase transition under these same conditions.

Following 2-week storage at 5° C., reversible solid-liquid phase transition was observed in F17, F18 and F19 samples. Upon warming/equilibration to room temperature, formulations returned to clear liquid solution. The other formulations (F12, F16, F20, and F21) did not show visible solidification/phase transition under these same conditions.

Following 2-week storage at 25° C., all samples remained in liquid phase, but many particles were visible in F21.

Following 2-week storage at 40° C., increased opalescence was observed in F13, F18, F19, and F20. In view of results in Example 2, the increased opalescence observed in F13 was unexpected.

Figure 8:
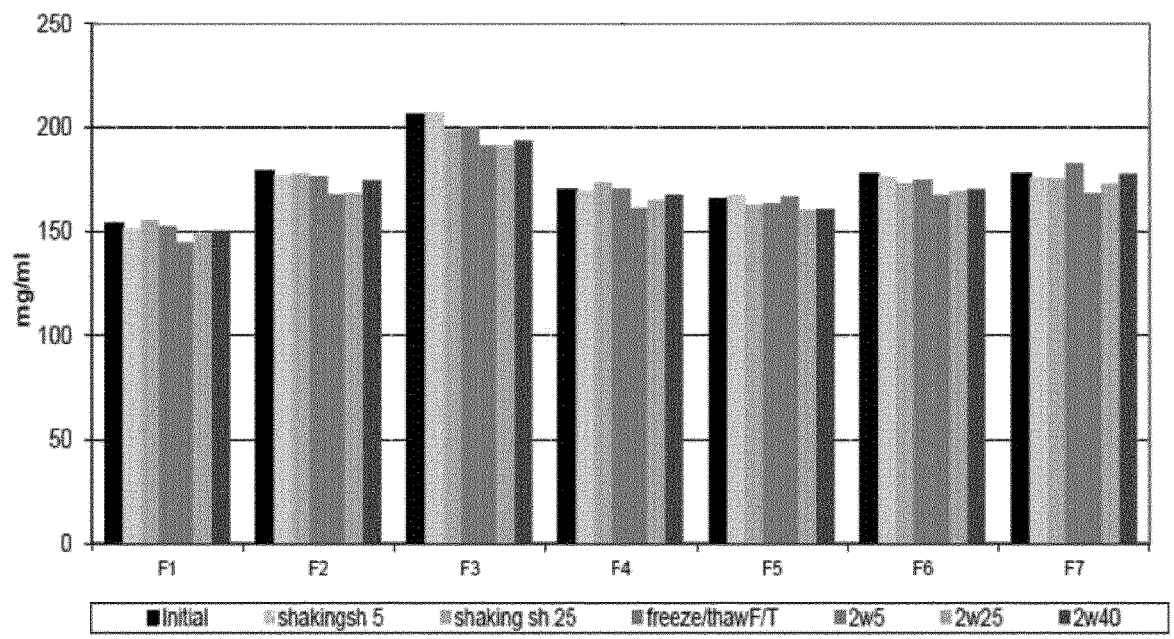
FIG. 8 depicts protein concentration as measured by UV/Vis of ARGX-113 formulations described in Example 3. sh 5, shaking at 5° C.; sh 25, shaking at 25° C.; 2w5, 2 weeks at 5° C.; 2w25, 2 weeks at 25° C.; 2w40, 2 weeks at 40° C.

FIG. 8 shows that there was no major change in ARGX-113 protein concentration during these stability studies.

Figure 9:
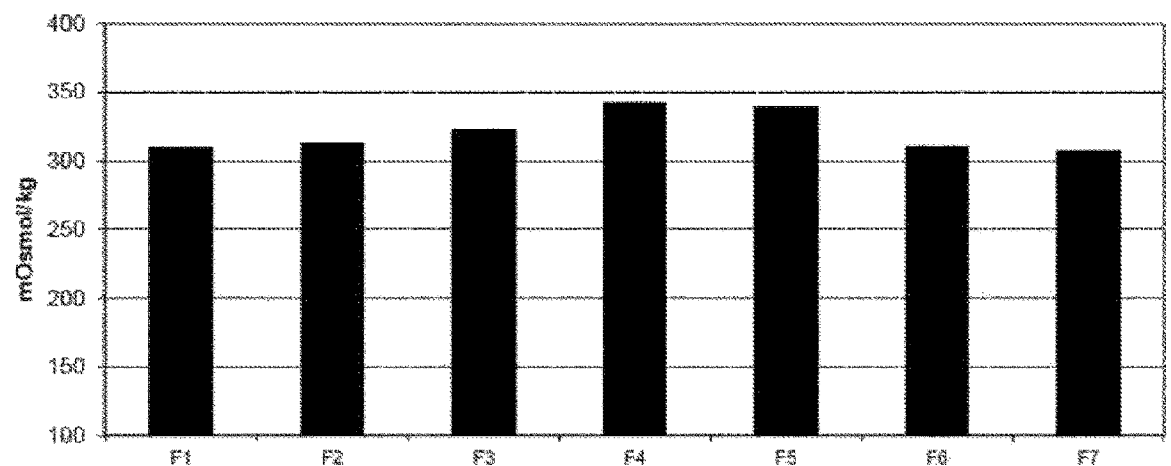
FIG. 9 depicts osmolality as measured by freezing point depression of ARGX-113 formulations described in Example 3.

FIG. 9 shows osmolality of the formulations after 2-week storage at 5° C.

Figure 10:
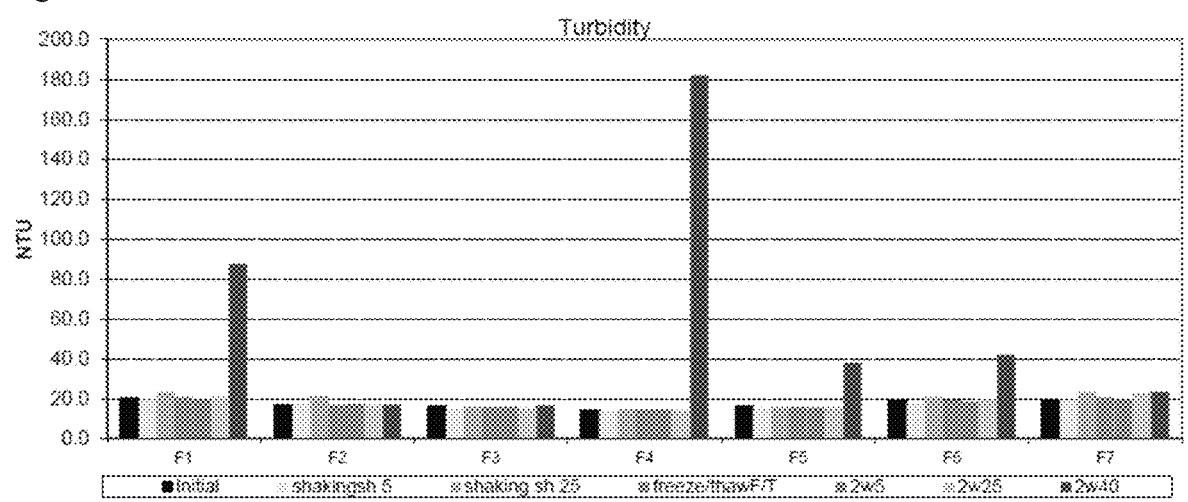
FIG. 10 depicts turbidity of ARGX-113 formulations described in Example 3. sh 5, shaking at 5° C.; sh 25, shaking at 25° C.; 2w5, 2 weeks at 5° C.; 2w25, 2 weeks at 25° C.; 2w40, 2 weeks at 40° C.

FIG. 10 shows that F13 and F18 showed significant increase in turbidity after 2-week storage at 40° C. Turbidity was doubled in F19 and F20 after 2-week storage at 40° C.

Figure 11A:
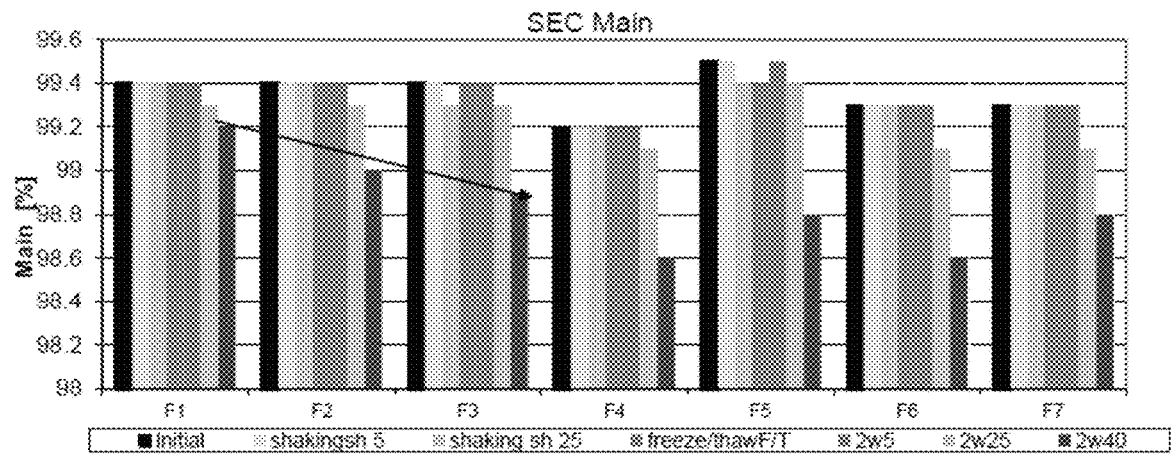
FIGS. 11A and 11B depict size exclusion chromatography (SEC) results for the main peak and high molecular weight (HMW) species, respectively, of ARGX-113 formulations described in Example 3. sh 5, shaking at 5° C.; sh 25, shaking at 25° C.; 2w5, 2 weeks at 5° C.; 2w25, 2 weeks at 25° C.; 2w40, 2 weeks at 40° C.
Figure 11B:
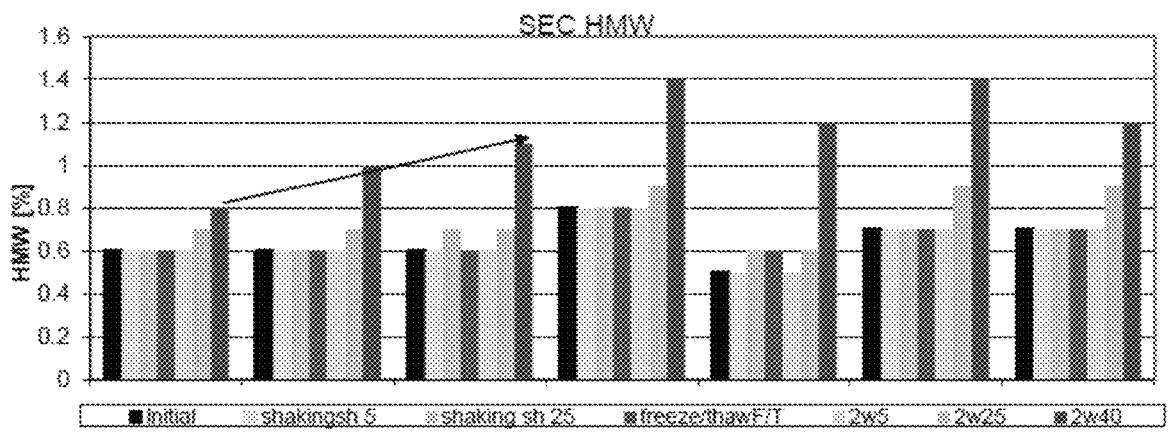
Figure 12A:
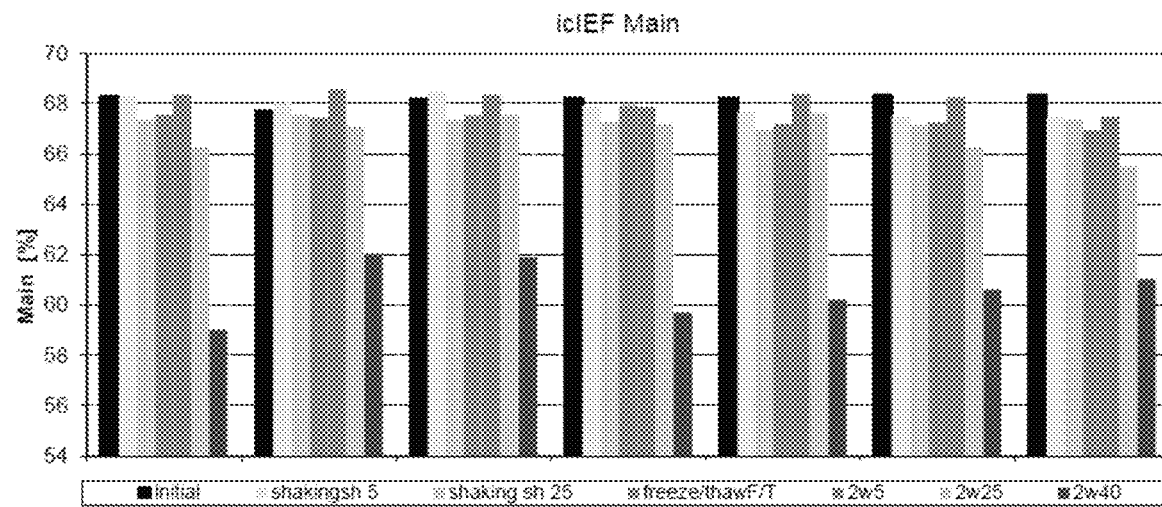
FIGS. 12A-12C depict chemical degradation as determined by iCE for the main peak, acidic variants, and basic variants, respectively, of ARGX-113 formulations described in Example 3. sh 5, shaking at 5° C.; sh 25, shaking at 25° C.; 2w5, 2 weeks at 5° C.; 2w25, 2 weeks at 25° C.; 2w40, 2 weeks at 40° C.
Figure 12B:
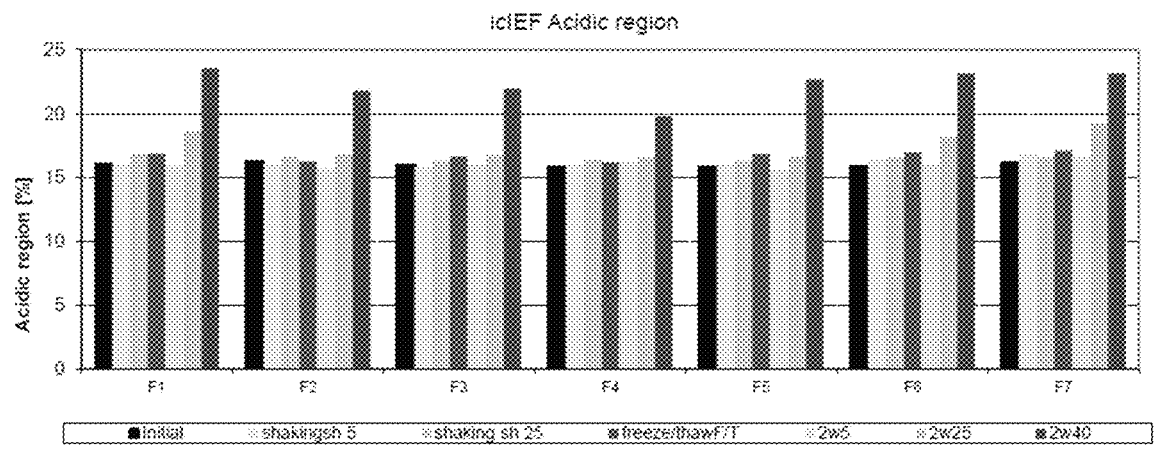
Figure 12C:
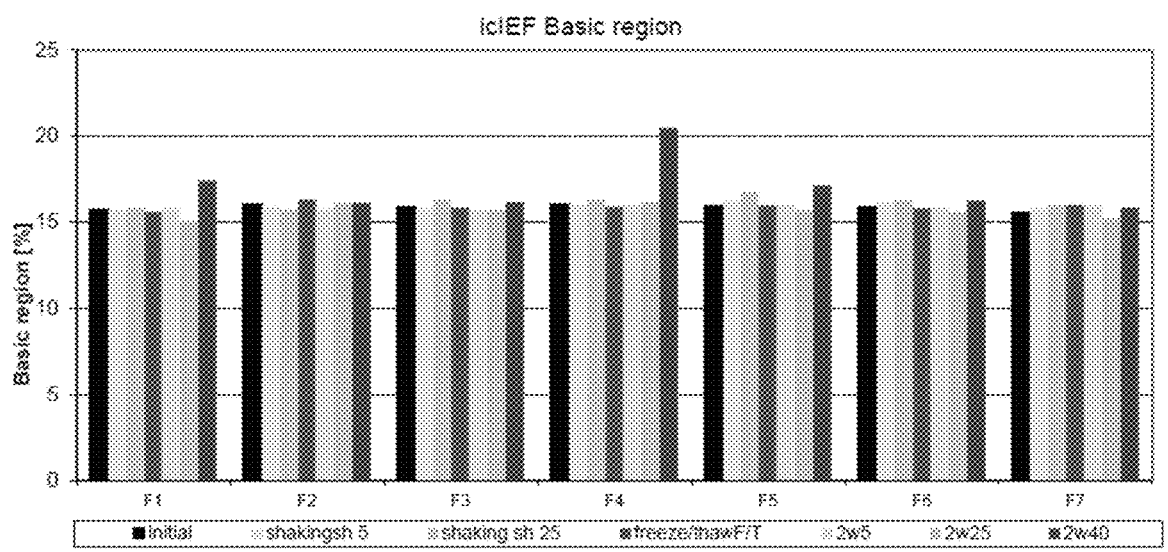
Figure 13A:
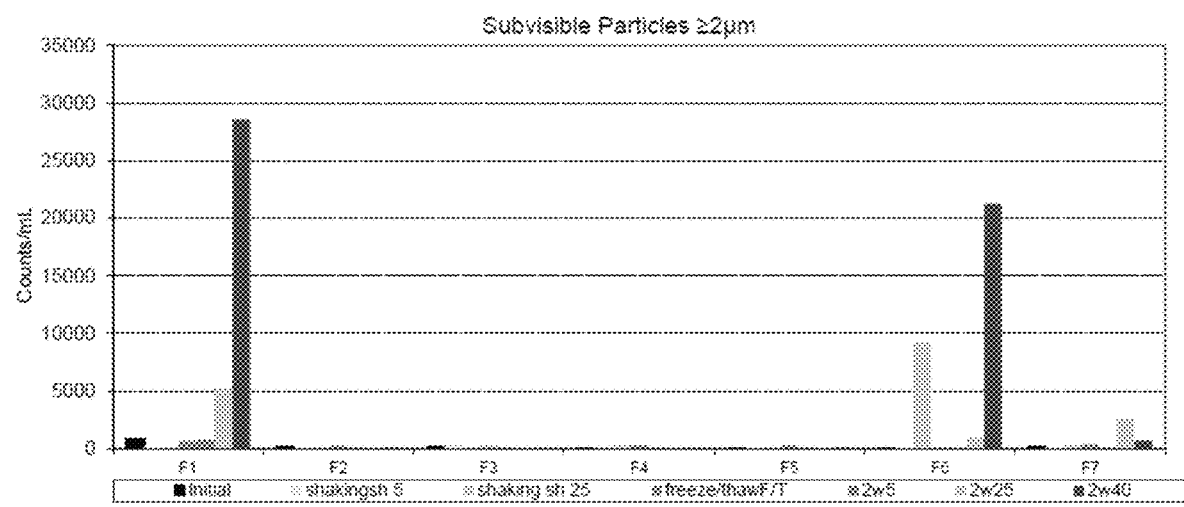
FIGS. 13A-13D depict subvisible particles ≥2 µm, ≥5 µm, ≥10 µm, and ≥25 µm in diameter, respectively, of ARGX-113 formulations described in Example 3. sh 5, shaking at 5° C.; sh 25, shaking at 25° C.; 2w5, 2 weeks at 5° C.; 2w25, 2 weeks at 25° C.; 2w40, 2 weeks at 40° C.
Figure 13B:
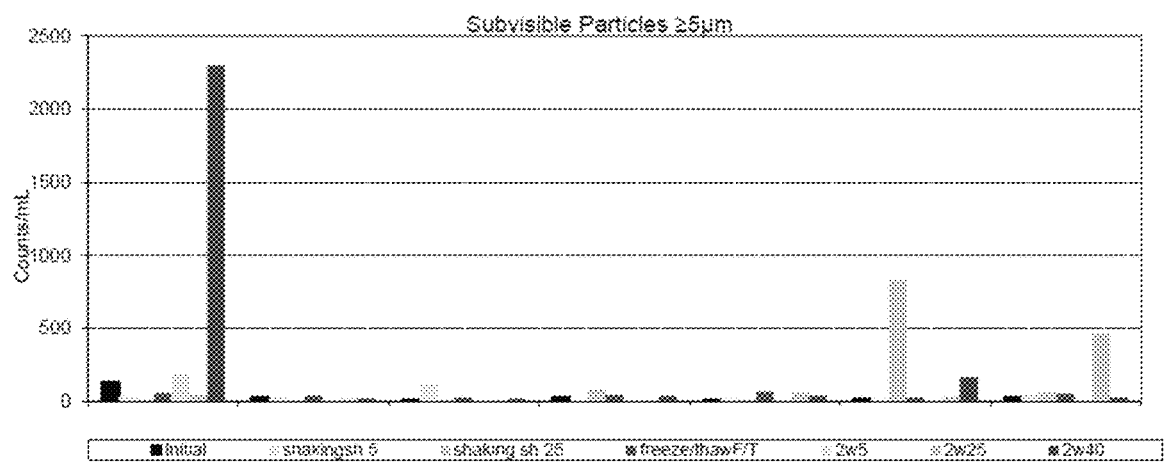
Figure 13C:
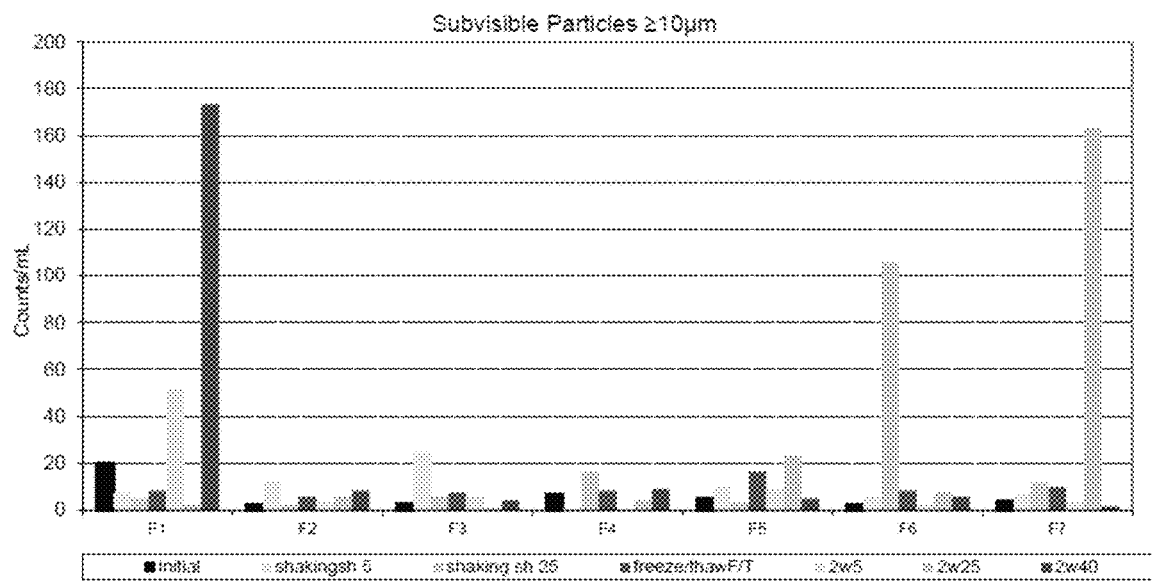
Figure 13D:
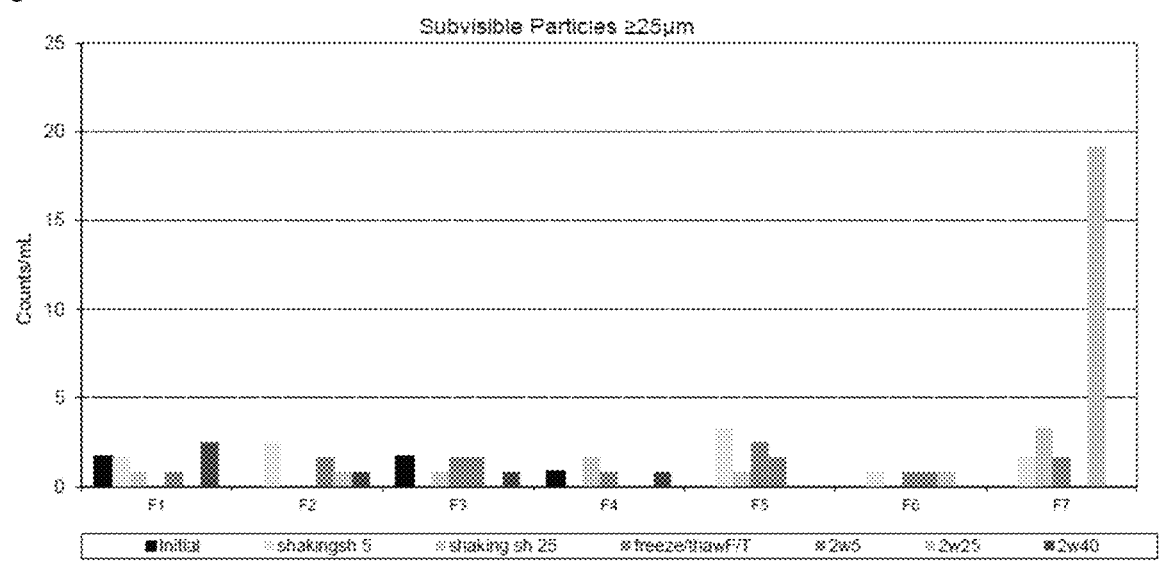

FIGS. 11A-11B show aggregation results.
FIGS. 12A-12C show iCE results.
FIGS. 13A-13D show subvisible particle results.

In FIGS. 8, 9, 10, 11A-11B, 12A-12C, 13A-13D: F1=F13; F2=F16; F3=F17; F4=F18; F5=F19; F6=F20; F7=F21. The bars shown in the order from left to right in FIGS. 8, 10, 11A-11B, 12A-12C, 13A-13D are the following (remark: several bars in FIG. 13A-13D are very low but the order of the bars is the same, even when there is almost no bar visible in the graph): F1 initial; F1 shaking at 5° C. (shakingsh 5); F1 shaking at 25° C. (shaking sh 25); F1 5 cycles of freeze/thaw stress (freeze/thawF/T); F1 2 weeks at 5° C. (2W5); F1 2 weeks at 25° C. (2W25); F1 2 weeks at 40° C. (2W40); F2 initial; F2 shaking at 5° C. (shakingsh 5); F2 shaking at 25° C. (shaking sh 25); F2 5 cycles of freeze/thaw stress (freeze/thawF/T); F2 2 weeks at 5° C. (2W5); F2 2 weeks at 25° C. (2W25); F2 2 weeks at 40° C. (2W40); F3 initial; F3 shaking at 5° C. (shakingsh 5); F3 shaking at 25° C. (shaking sh 25); F3 5 cycles of freeze/thaw stress (freeze/thawF/T); F3 2 weeks at 5° C. (2W5); F3 2 weeks at 25° C. (2W25); F3 2 weeks at 40° C. (2W40); F4 initial; F4 shaking at 5° C. (shakingsh 5); F4 shaking at 25° C. (shaking sh 25); F4 5 cycles of freeze/thaw stress (freeze/thawF/T); F4 2 weeks at 5° C. (2W5); F4 2 weeks at 25° C. (2W25); F4 2 weeks at 40° C. (2W40); F5 initial; F5 shaking at 5° C. (shakingsh 5); F5 shaking at 25° C. (shaking sh 25); F5 5 cycles of freeze/thaw stress (freeze/thawF/T); F5 2 weeks at 5° C. (2W5); F5 2 weeks at 25° C. (2W25); F5 2 weeks at 40° C. (2W40); F6 initial; F6 shaking at 5° C. (shakingsh 5); F6 shaking at 25° C. (shaking sh 25); F6 5 cycles of freeze/thaw stress (freeze/thawF/T); F6 2 weeks at 5° C. (2W5); F6 2 weeks at 25° C. (2W25); F6 2 weeks at 40° C. (2W40); F7 initial; F7 shaking at 5° C. (shakingsh 5); F7 shaking at 25° C. (shaking sh 25); F7 5 cycles of freeze/thaw stress (freeze/thawF/T); F7 2 weeks at 5° C. (2W5); F7 2 weeks at 25° C. (2W25); F7 2 weeks at 40° C. (2W40).

From the results obtained in this example, it was concluded that (i) polysorbate 20 at 0.02% and 0.04% were equally effective with respect to protecting ARGX-113 from shaking and freeze/thaw stress, irrespective of protein concentration (e.g., 150 or 175 mg/mL); (ii) polysorbate 20 and polysorbate 80 were equally effective with respect to protecting ARGX-113 from shaking and freeze/thaw stress; (iii) polysorbate 20 and poloxamer 188 were equally effective with respect to protecting ARGX-113 from shaking and freeze/thaw stress; (iv) aggregation was concentration-dependent and F16 and F17 (175 mg/mL and 200 mg/mL, respectively) had greater aggregation after 2-week storage at 40° C. compared to F13 (150 mg/mL); (v) ARGX-113 concentration ≥175 mg/mL showed reversible temperature-dependent solid-liquid phase transition; and (vi) lower pH (5.0 and 5.3) showed higher risk of reversible temperature-dependent solid-liquid phase transition, and pH 5.0 showed possible risk of chemical degradation forming basic species and possible fragmentation.

Example 4. Further Excipient Characterization

This example describes yet additional experiments that were undertaken to develop and characterize further candidate high-concentration formulations of ARGX-113. In particular, a goal of this set of experiments was to identify a candidate high-concentration liquid formulation of ARGX-113 for pre-clinical toxicology and early phase clinical studies based on certain characteristics and short-term stability studies.

The compositions of seven aqueous formulations of ARGX-113 studied in this example are shown in Table 5.

TABLE 5

| ID | ARGX-113 | Buffer | pH | Excipient 1 | Excipient 2 | Excipient 3 | Surfactant |
|---|---|---|---|---|---|---|---|
| F22 | 175 mg/mL | 20 mM HisHCl | 6.0 | 100 mM ArgCl | 60 mM Sucrose | 10 mM L-Methionine | 0.03% w/v PS20 |
| F23 | 175 mg/mL | 20 mM HisHCl | 6.0 | 100 mM NaCl | 60 mM Sucrose | 10 mM L-Methionine | 0.03% w/v PS20 |
| F24 | 175 mg/mL | 20 mM HisHCl | 6.0 | 100 mM ArgCl | 60 mM Sucrose | 10 mM L-Methionine | 0.03% w/v PS20 |
| F25 | 175 mg/mL | 20 mM HisHCl | 6.0 | 100 mM NaCl | 60 mM Sucrose | 10 mM L-Methionine | 0.03% w/v PS20 |
| F26 | 160 mg/mL | 20 mM HisHCl | 6.0 | 100 mM ArgCl | 60 mM Sucrose | — | 0.03% w/v PS20 |
| F27 | 160 mg/mL | 20 mM HisHCl | 6.0 | 100 mM NaCl | 60 mM Sucrose | — | 0.03% w/v PS20 |

PS20: polysorbate 20

F22 and F23 were prepared as 2.0 mL aliquots in vials.

F24 and F25 were prepared as 2.0 mL aliquots in Nuovo Ompi glass syringes.

F26 and F27 were prepared as 2.0 mL aliquots in BD SCF Neopak glass syringes.

For F22, F24, and F26, buffer exchange and up-concentration were performed in 20 mM HisHCl, 100 mM ArgCl, with or without 10 mM L-methionine, at selected pH, followed by bulk filtration and, for compounded samples, addition of appropriate amounts of sucrose and surfactant stocks to achieve target concentrations. Compounded and uncompounded formulations were stored at 5° C. overnight to observe for any phase transition. No phase separation was observed in any of the compounded or uncompounded formulations. Then compounded formulations underwent filtration, fill, and finish.

For F23, F25, and F27, buffer exchange and up-concentration were performed in 20 mM HisHCl, 100 mM NaCl, with or without 10 mM L-methionine, at selected pH, followed by bulk filtration and, for compounded samples, addition of appropriate amounts of sucrose and surfactant stocks to achieve target concentrations. Compounded and uncompounded formulations were stored at 5° C. overnight to observe for any phase transition. No phase separation was observed in any of the compounded formulations, but phase separation was observed in the uncompounded bulk formulation. Then compounded formulations underwent filtration, fill, and finish.

All formulations were then subjected to certain storage conditions for specified periods of time prior to analysis in terms of visual appearance, color, clarity, pH, sub-visible particles, purity by SE-HPLC, purity by iCE, purity by CE-SDS, viscosity, and break and glide force measurement.

All formulations remained in liquid phase under conditions of 3 weeks storage at 5° C., 3 weeks storage at 25° C., and 3 weeks storage at 40° C.

All formulations remained in liquid phase under conditions of 6 weeks storage at 5° C., 6 weeks storage at 25° C., and 6 weeks storage at 40° C., although some haze formation was observed in F22 and F26 after 6 weeks storage at 40° C.

All formulations remained in liquid phase under conditions of 9 weeks storage at 5° C., 9 weeks storage at 25° C., and 9 weeks storage at 40° C., although some precipitation was observed in all formulations stored for 9 weeks at 40° C.

Protein concentration was found to be essentially stable (within 10 percent of initial concentration) for each of F22-F27 under conditions of shaking at 5° C., shaking at 25° C., freeze/thaw, 3 weeks storage at 5° C., 3 weeks storage at 25° C., 3 weeks storage at 40° C., 6 weeks storage at 5° C., 6 weeks storage at 25° C., 6 weeks storage at 40° C., 9 weeks storage at 5° C., 9 weeks storage at 25° C., and 9 weeks storage at 40° C.

pH was found to be stable for each of F22-F27 under conditions of shaking at 5° C., shaking at 25° C., freeze/thaw, 3 weeks storage at 5° C., 3 weeks storage at 25° C., 3 weeks storage at 40° C., 6 weeks storage at 5° C., 6 weeks storage at 25° C., 6 weeks storage at 40° C., 9 weeks storage at 5° C., 9 weeks storage at 25° C., and 9 weeks storage at 40° C.

All formulations at all times studied were practically free from visible particles except for F22 and F24 after 6 weeks storage at 40° C., and all formulations after 9 weeks storage at 40° C.

Osmolality, viscosity, break force, and glide force of the various syringe formulations stored at 5° C. for 9 weeks are shown in Table 6.

TABLE 6

| ID | Osmolality (mOsmol/kg) | Viscosity (cP) | Syringeability | |
|---|---|---|---|---|
| | | | Break Force | Glide Force |
| F24 | 319 | 6 | 4.4 | 6.4 |
| F25 | 331 | 6 | 4.7 | 6.6 |
| F26 | 308 | 5 | 4.1 | 3.8 |
| F27 | 307 | 5 | 4.3 | 4.2 |

Figure 14:
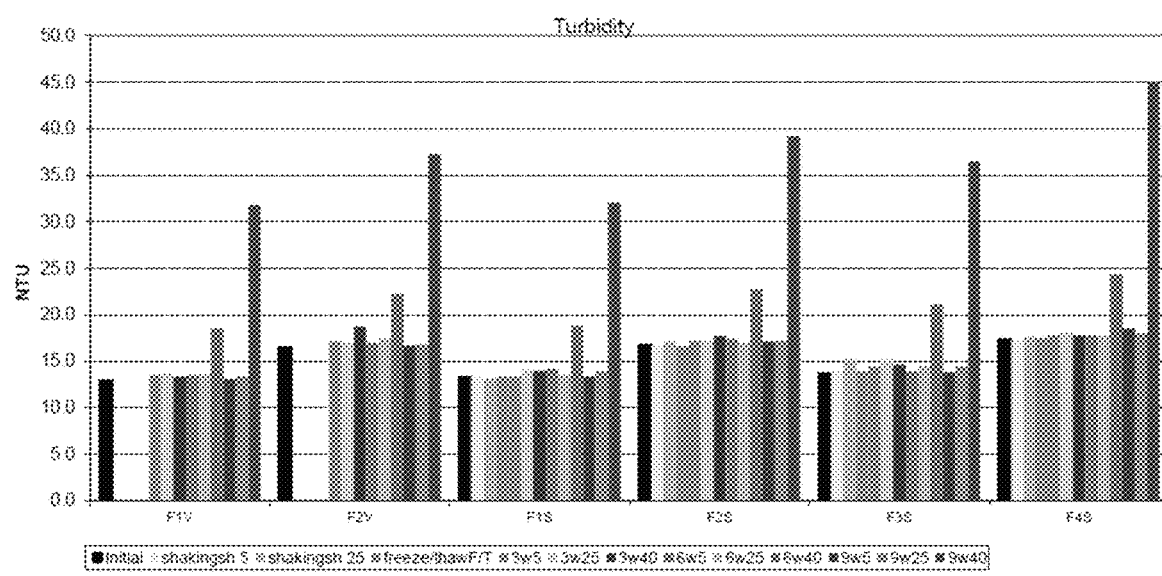
FIG. 14 depicts turbidity of ARGX-113 formulations described in Example 4. sh 5, shaking at 5° C.; sh 25, shaking at 25° C.; 3w5, 3 weeks at 5° C.; 3w25, 3 weeks at 25° C.; 3w40, 3 weeks at 40° C.; 6w5, 6 weeks at 5° C.; 6w25, 6 weeks at 25° C.; 6w40, 6 weeks at 40° C.; 9w5, 9 weeks at 5° C.; 9w25, 9 weeks at 25° C.; 9w40, 9 weeks at 40° C.

As shown in FIG. 14, an increase in turbidity was observed for all formulations stored for 9 weeks at 40° C., and NaCl formulations and formulations without L-methionine showed slightly higher turbidity than ArgCl formulations.

Figure 15A:
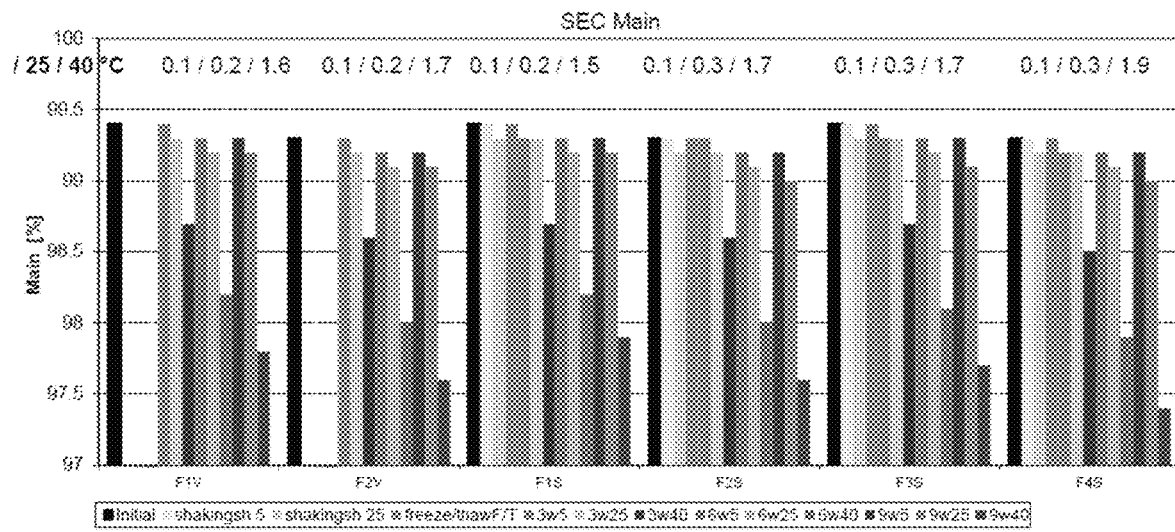
FIGS. 15A and 15B depict size exclusion chromatography (SEC) results for the main peak and high molecular weight (HMW) species, respectively, of ARGX-113 formulations described in Example 4. sh 5, shaking at 5° C.; sh 25, shaking at 25° C.; 3w5, 3 weeks at 5° C.; 3w25, 3 weeks at 25° C.; 3w40, 3 weeks at 40° C.; 6w5, 6 weeks at 5° C.; 6w25, 6 weeks at 25° C.; 6w40, 6 weeks at 40° C.; 9w5, 9 weeks at 5° C.; 9w25, 9 weeks at 25° C.; 9w40, 9 weeks at 40° C.
Figure 15B:
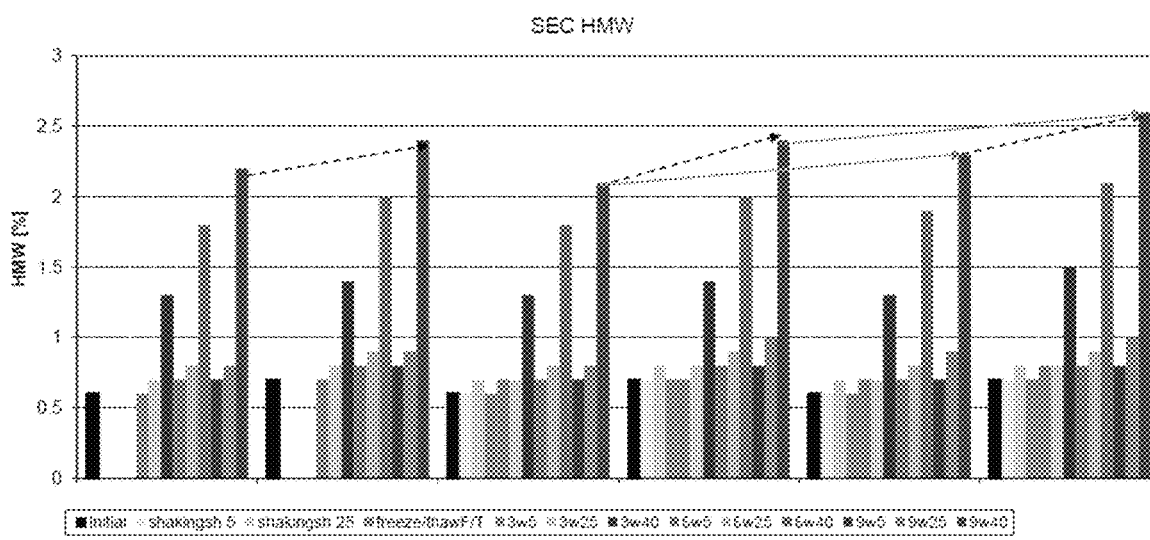

Aggregation was assessed using SE-HPLC. FIGS. 15A-15B show aggregation results. After 9 weeks of storage at 40° C., around 1.5-1.9% loss in the main peak was observed depending on the formulation. F23 and F25 (NaCl formulations) showed slightly higher loss in the main peak at 40° C. compared to F22 and F24 (ArgCl formulations). F26 and F27 (without L-methionine) showed slightly higher loss in the main peak at 40° C. compared to formulations with L-methionine. Loss in monomer was mainly due to high molecular weights (HMWs) and aggregates formation. F23 and F25 (NaCl formulations) showed slightly higher aggregation at 40° C. compared to F22 and F24 (ArgCl formulations). F26 and F27 (without L-methionine) showed slightly higher HMWs at 40° C. compared to formulations with L-methionine.

Figure 16A:
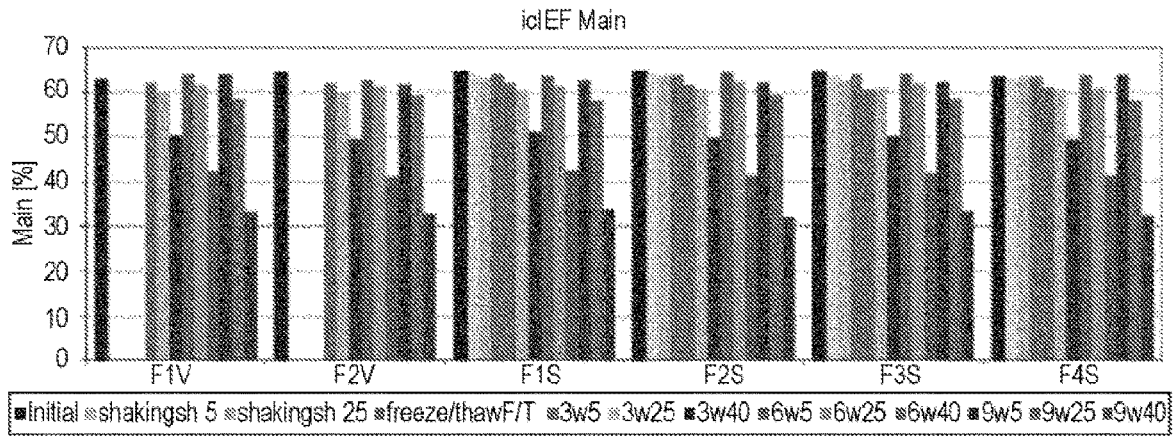
FIGS. 16A-16C depict chemical degradation as determined by iCE for the main peak, acidic variants, and basic variants, respectively, of ARGX-113 formulations described in Example 4. sh 5, shaking at 5° C.; sh 25, shaking at 25° C.; 3w5, 3 weeks at 5° C.; 3w25, 3 weeks at 25° C.; 3w40, 3 weeks at 40° C.; 6w5, 6 weeks at 5° C.; 6w25, 6 weeks at 25° C.; 6w40, 6 weeks at 40° C.; 9w5, 9 weeks at 5° C.; 9w25, 9 weeks at 25° C.; 9w40, 9 weeks at 40° C.
Figure 16B:
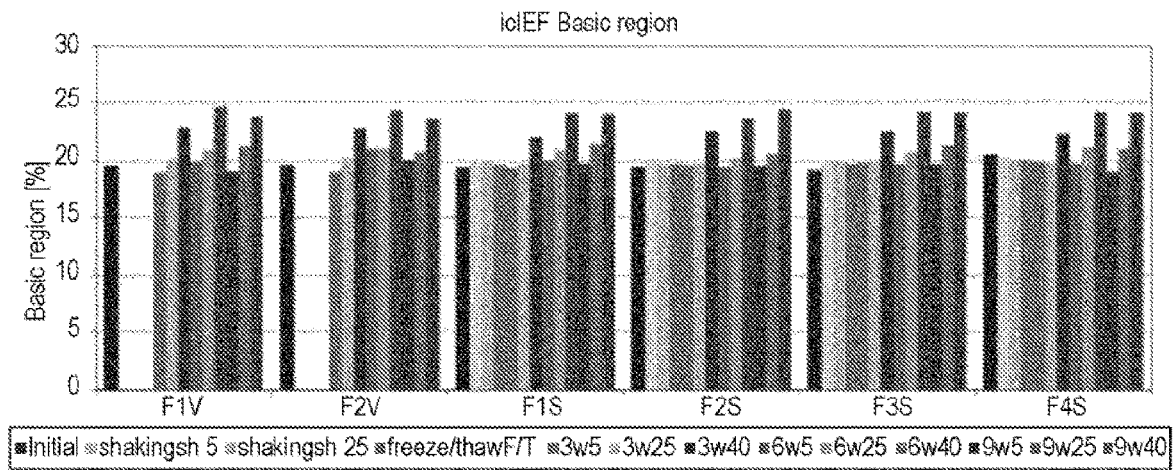
Figure 16C:
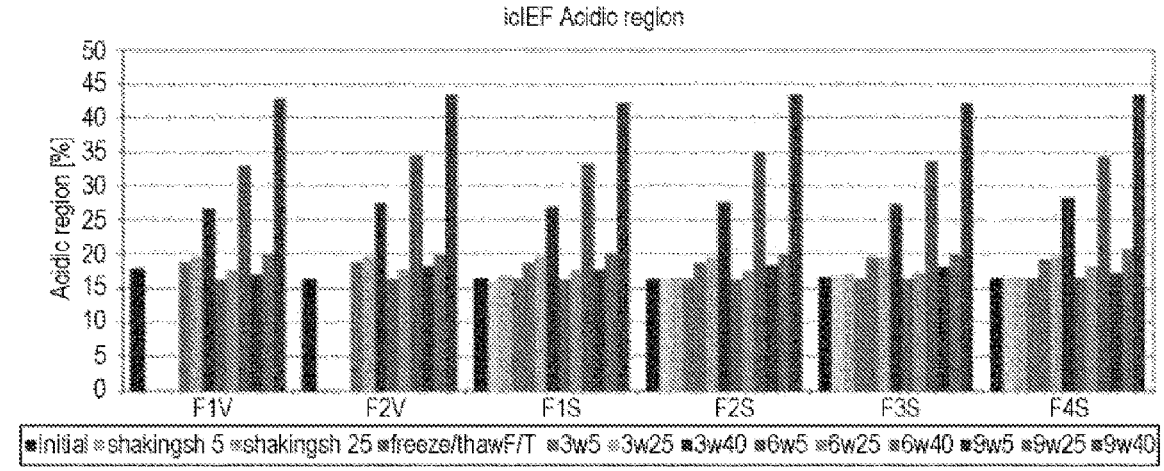
Figure 17A:
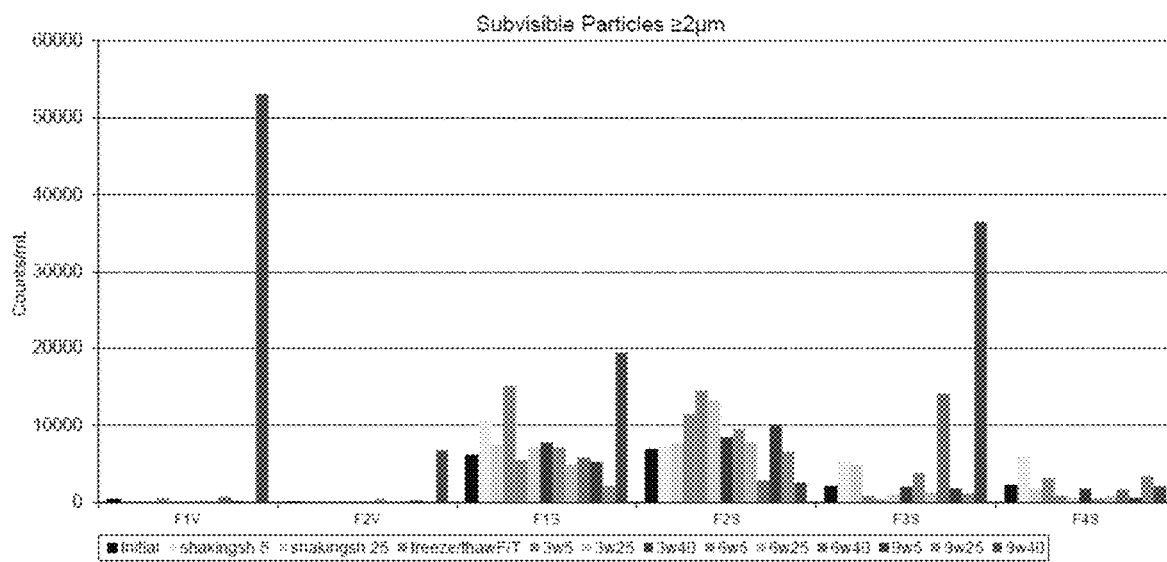
FIGS. 17A-17D depict subvisible particles ≥2 µm, ≥5 µm, ≥10 µm, and ≥25 µm in diameter, respectively, of ARGX-113 formulations described in Example 4. sh 5, shaking at 5° C.; sh 25, shaking at 25° C.; 3w5, 3 weeks at 5° C.; 3w25, 3 weeks at 25° C.; 3w40, 3 weeks at 40° C.; 6w5, 6 weeks at 5° C.; 6w25, 6 weeks at 25° C.; 6w40, 6 weeks at 40° C.; 9w5, 9 weeks at 5° C.; 9w25, 9 weeks at 25° C.; 9w40, 9 weeks at 40° C.
Figure 17B:
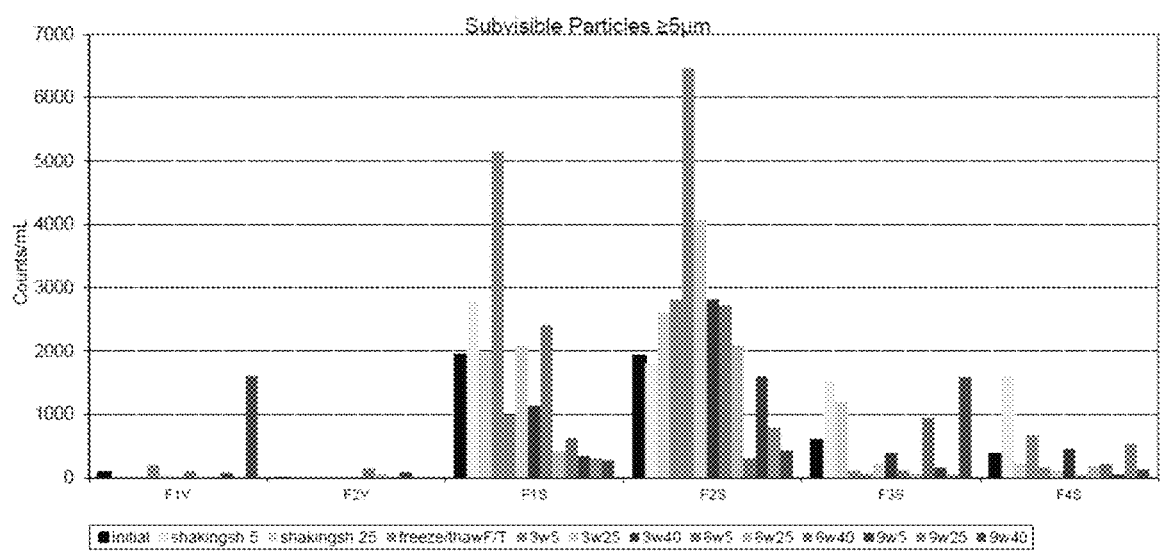
Figure 17C:
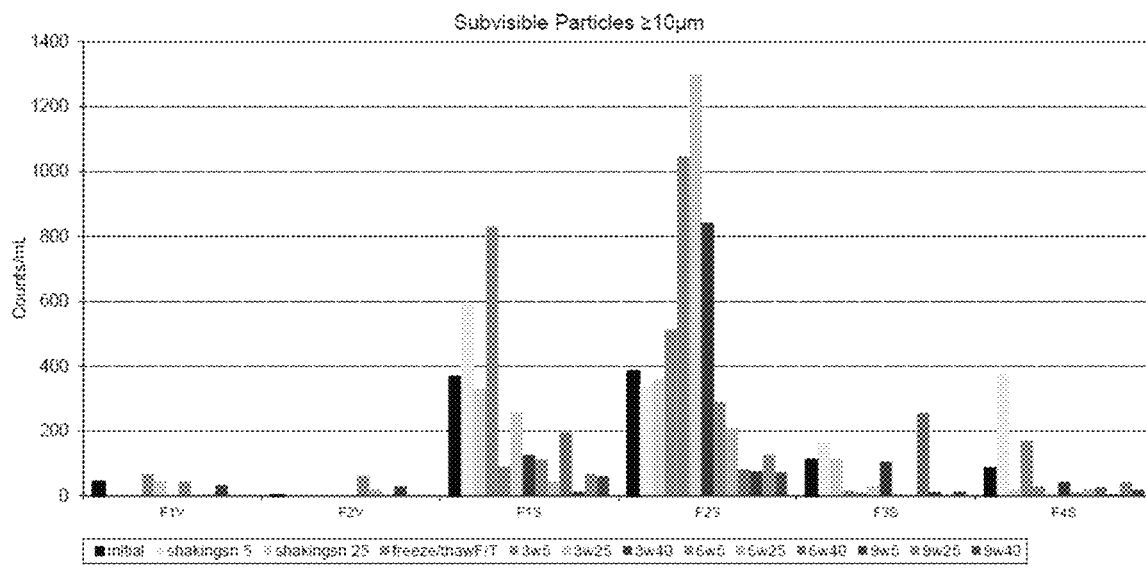
Figure 17D:
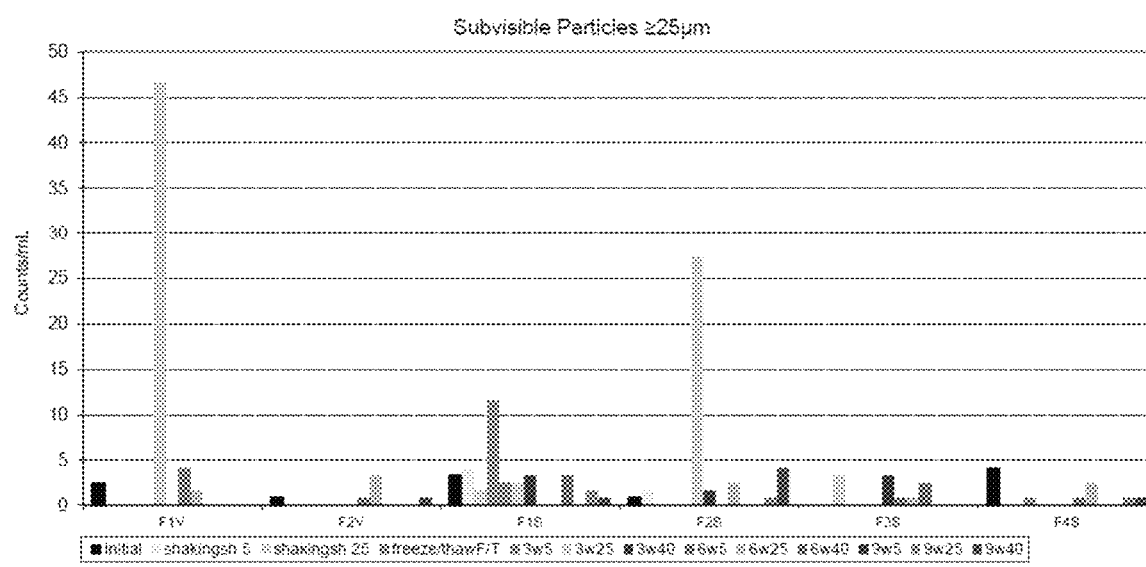

FIGS. 16A-16C show iCE results. All formulations showed similar extent of loss in the main peak (29-32%) after storage for 9 weeks at 40° C. A similar extent of increase in basic and acidic species was observed.

FIGS. 17A-17D show subvisible particle results. Data shown for samples stored for 9 weeks at 40° C. may not be reliable due to precipitation in these samples.

From the results obtained in this example, it was concluded that (i) uncompounded ArgCl-containing formulations remained in liquid state after storage at 5° C. even at concentration around 200 mg/mL; (ii) in contrast, uncompounded NaCl-containing formulations did not remain in liquid state after storage at 5° C. at concentration around 200 mg/mL; (iii) compounded ArgCl-containing formulations exhibited precipitation after storage for 6 weeks at 40° C.; (iv) in contrast, compounded NaCl-containing formulations exhibited no precipitation after storage for 6 weeks at 40° C.; (v) compounded NaCl-containing formulations exhibited higher aggregation rate than ArgCl formulations; and (vi) precipitation of compounded NaCl-containing formulations was observed after storage for 9 weeks at 40° C.

In FIGS. 14, 15A-15B, 16A-16C, 17A-17D: F1V=F22; F2V=F23; F1S=F24; F2S=F25; F3S=F26; F4S=F27. The bars shown in the order from left to right in FIGS. 14, 15A-15B, 16A-16C, 17A-17D are the following (remark: several bars in FIG. 17A-17D are very low but the order of the bars is the same, even when there is almost no bar visible in the graph): F1V initial; F1V shaking at 5° C. (shakingsh 5); F1V shaking at 25° C. (shaking sh 25); F1V 5 cycles of freeze/thaw stress (freeze/thawF/T); F1V 3 weeks at 5° C. (3W5); F1V 3 weeks at 25° C. (3W25); F1V 3 weeks at 40° C. (3W40); F1V 6 weeks at 5° C. (6W5); F1V 6 weeks at 25° C. (6W25); F1V 6 weeks at 40° C. (6W40); F1V 9 weeks at 5° C. (9W5); F1V 9 weeks at 25° C. (9W25); F1V 9 weeks at 40° C. (9W40); F2V initial; F2V shaking at 5° C. (shakingsh 5); F2V shaking at 25° C. (shaking sh 25); F2V 5 cycles of freeze/thaw stress (freeze/thawF/T); F2V 3 weeks at 5° C. (3W5); F2V 3 weeks at 25° C. (3W25); F2V 3 weeks at 40° C. (3W40); F2V 6 weeks at 5° C. (6W5); F2V 6 weeks at 25° C. (6W25); F2V 6 weeks at 40° C. (6W40); F2V 9 weeks at 5° C. (9W5); F2V 9 weeks at 25° C. (9W25); F2V 9 weeks at 40° C. (9W40); F1S initial; F1S shaking at 5° C. (shakingsh 5); F1S shaking at 25° C. (shaking sh 25); F1S 5 cycles of freeze/thaw stress (freeze/thawF/T); F1S 3 weeks at 5° C. (3W5); F1S 3 weeks at 25° C. (3W25); F1S 3 weeks at 40° C. (3W40); F1S 6 weeks at 5° C. (6W5); F1S 6 weeks at 25° C. (6W25); F1S 6 weeks at 40° C. (6W40); F1S 9 weeks at 5° C. (9W5); F1S 9 weeks at 25° C. (9W25); F1S 9 weeks at 40° C. (9W40); F2S initial; F2S shaking at 5° C. (shakingsh 5); F2S shaking at 25° C. (shaking sh 25); F2S 5 cycles of freeze/thaw stress (freeze/thawF/T); F2S 3 weeks at 5° C. (3W5); F2S 3 weeks at 25° C. (3W25); F2S 3 weeks at 40° C. (3W40); F2S 6 weeks at 5° C. (6W5); F2S 6 weeks at 25° C. (6W25); F2S 6 weeks at 40° C. (6W40); F2S 9 weeks at 5° C. (9W5); F2S 9 weeks at 25° C. (9W25); F2S 9 weeks at 40° C. (9W40); F3S initial; F3S shaking at 5° C. (shakingsh 5); F3S shaking at 25° C. (shaking sh 25); F3S 5 cycles of freeze/thaw stress (freeze/thawF/T); F3S 3 weeks at 5° C. (3W5); F3S 3 weeks at 25° C. (3W25); F3S 3 weeks at 40° C. (3W40); F3S 6 weeks at 5° C. (6W5); F3S 6 weeks at 25° C. (6W25); F3S 6 weeks at 40° C. (6W40); F3S 9 weeks at 5° C. (9W5); F3S 9 weeks at 25° C. (9W25); F3S 9 weeks at 40° C. (9W40); F4S initial; F4S shaking at 5° C. (shakingsh 5); F4S shaking at 25° C. (shaking sh 25); F4S 5 cycles of freeze/thaw stress (freeze/thawF/T); F4S 3 weeks at 5° C. (3W5); F4S 3 weeks at 25° C. (3W25); F4S 3 weeks at 40° C. (3W40); F4S 6 weeks at 5° C. (6W5); F4S 6 weeks at 25° C. (6W25); F4S 6 weeks at 40° C. (6W40); F4S 9 weeks at 5° C. (9W5); F4S 9 weeks at 25° C. (9W25); F4S 9 weeks at 40° C. (9W40).

Example 5. Further Testing for pH Optimization

This example describes the comparison between 2 preparation methods: method 1 (pilot) was compared to method 2 (GMP). Method 2 resulted in a more accurate pH compared to Preparation 1.

Several excipients were added to WFI (water for injection), dissolved and then the formulation buffer with the different excipients was brought to volume. The excipients were added in a random order.

The resulting formulation buffer was used during the UF/DF (ultrafiltration/diafiltration) formulation step of the protein (ARGX-113). The polysorbate 20 had not been added at this moment yet.

TABLE 7

|  | Chemicals | Pilot (Method 1) | GMP (Method 2) |
| --- | --- | --- | --- |
| Concentration (g/L) | L-Histidine | 1.436 | 1.552 |
|  | L-Histidine Monohydrochloride | 2.252 | 2.096 |
|  | Sodium Chloride | 5.844 | 5.84 |
|  | L-Methionine | 1.492 | 1.492 |
|  | Sucrose | 20.54 | 20.54 |

Next the polysorbate was added via a 10% solution by dilution 996:4 (example: to 1000 kg of the product formulation buffer, 4008 ml excipient buffer was added), which is called the excipient addition step. So the polysorbate 20 (PS20) was added after the diafiltration/ultrafiltration step.

This resulted in the following final ARGX-113 formulation:

165 mg/mL ARGX-113 in 20 mM L-histidine/L-histidine hydrochloride, 100 mM sodium chloride, 60 mM sucrose, 10 mM L-methionine with 0.04% (w/v) polysorbate 20 at pH 6.0.

It is understood by the skilled person that the methods from this Example can also be used to make formulations with higher protein (ARGX-113) concentrations than 165 mg/mL, e.g. 180 mg/mL or 200 mg/mL or as high as 300 mg/mL.

Example 6. Ultra-High Concentration Formulations

In this example additional experiments were performed to evaluate the possibility of viscosity-reducing formulation conditions for an even higher concentration of ARGX-113, e.g., 250 to 300 mg/mL. Three formulations were prepared at different pH values and ionic strengths for this purpose. The three target formulations are shown in Table 8.

TABLE 8

| | Target formulations | | |
| --- | --- | --- | --- |
|  | F101 | F102 | F103 |
| pH | 5.5 | 6.0 | 6.5 |
| ARGX-113, mg/mL | 250 | 250 | 250 |
| Histidine Buffer, mM | 50 | 50 | 50 |
| Arginine, mM | 200 | 200 | 200 |
| Volume, mL | 1 | 1 | 1 |

Materials and Methods

Stock solution of ARGX-113 was subjected to buffer exchange, followed by upconcentration, measurement of protein (ARGX-113) concentration, dilution to about 250 mg/mL, and spiking with excipients. Each of the resulting formulations was subdivided into a 5° C. storage lot and a 25° C. storage lot, then analyzed periodically over the course of 14 days for viscosity, osmolality, visual inspection, and filtration testing with 0.22 μm filter. Analysis was performed at days 0 (DO; day of preparation), 3 (D3), 7 (D7), and 14 (D14).

Results
Observed pH, osmolality, protein concentration, viscosity, and visual appearance are shown in Table 9.

TABLE 9

|  | Units | F101 | F102 | F103 |
|---|---|---|---|---|
| pH | — | 5.5 | 6.0 | 6.5 |
| Osmolality | mOsm/kg | 556 | 516 | 469 |
| Protein conc. | mg/mL | 254 | 251 | 272 |
| Viscosity D 0 measured at 5° C. | mPA·s | 169 | 95 | 24 |
| Viscosity D 0 measured at 25° C. | mPA·s | 110 | 96 | 12 |
| Viscosity D 3 5° C. storage measured at 5° C. | mPA·s | nd | 69 | nd |
| Viscosity D 3 5° C. storage measured at 25° | mPA·s | 44 52 | 28 28 | 11 11 |
| Visual Appearance 7 days at 5° C. or 25° C. | — | Liquid with gel particles | Homogeneous, clear at both temperatures | Homogeneous, clear at both temperatures |
| Visual Appearance 14 days at 5° C. or 25° C. | — | Liquid with gel particles | Homogeneous, clear at both temperatures | Homogeneous, clear at both temperatures |
| Filtration D 14 5° C. storage | — | Not possible | Possible | Possible |
| Viscosity D 14 measured at 5° C. | mPA·s | — | 17 | 26 |
| Viscosity D 14 measured at 25° C. | mPA·s | — | 13 13 | 11 13 | nd: not done

To summarize:
- 3 formulations of ARGX-113 at concentration ≥250 mg/mL were prepared with Arginine 200 mM.
- The viscosity of the 3 formulations decreased with the pH value. F103 formulation was the lowest viscosity formulation at 5 and 25° C. over 2 weeks (pH=6.5 at 24 mPa·s, measured at 5° C.).
- F101 formulation could not be prepared homogeneously at small scale, due to formation of gel particles.
- F102 formulation showed unexpected variability in viscosity, that seemed to decrease with time.
- F103 formulation showed low viscosity that was quite reproducible within 2 weeks.
- The visual appearance of the stored formulations F102 and F103 remained the same over 2 weeks, whether storage was at 5° C. or 25° C.
- A whitish highly viscous solution was observed in stock solutions (270-280 mg/mL protein) containing 100 mM Arginine after 7 days. After 14 days, a solid gel was observed. (Data not shown.)
- A filtration test was performed: the viscosity of F102 and F103 stayed low (<26 mPa·s) after filtration at 5° C.

What is claimed is:

1. An aqueous formulation comprising about 100-300 mg/mL of a neonatal Fc receptor (FcRn) antagonist in 20-60 mM histidine/histidine HCl, 0-70 mM sucrose, 0-150 mM NaCl, 0-250 mM arginine HCl, 0.02%-0.05% (w/v) polysorbate 20 or polysorbate 80, 0-15 mM L-methionine, pH 6.0-6.5, wherein the FcRn antagonist consists of a variant Fc region, and wherein the variant Fc region consists of two Fc domains which form a homodimer, wherein the amino acid sequence of each of the Fc domains consists of the amino acid sequence set forth in SEQ ID NO: 1, SEQ ID NO: 2, or SEQ ID NO: 3.

2. The aqueous formulation according to claim 1, comprising about 100-200 mg/mL of the FcRn antagonist in 20 mM histidine/histidine HCl, 60 mM sucrose, 100 mM NaCl, and 0.02%-0.04% (w/v) polysorbate 20 or polysorbate 80, pH 6.0.

3. The aqueous formulation according to claim 1, comprising 150 mg/mL of the FcRn antagonist in 20 mM histidine/histidine HCl, 60 mM sucrose, 100 mM NaCl, and 0.04% (w/v) polysorbate 20, pH 6.0, wherein the amino acid sequence of each of the Fc domains of the FcRn antagonist consists of the amino acid sequence set forth in SEQ ID NO: 1.

4. The aqueous formulation according to claim 1, comprising 175 mg/mL of the FcRn antagonist in 20 mM histidine/histidine HCl, 60 mM sucrose, 100 mM NaCl, and 0.04% (w/v) polysorbate 20, pH 6.0, wherein the amino acid sequence of each of the Fc domains of the FcRn antagonist consists of the amino acid sequence set forth in SEQ ID NO: 1.

5. The aqueous formulation according to claim 1, comprising 200 mg/mL of the FcRn antagonist in 20 mM histidine/histidine HCl, 60 mM sucrose, 100 mM NaCl, and 0.04% (w/v) polysorbate 20, pH 6.0, wherein the amino acid sequence of each of the Fc domains of the FcRn antagonist consists of the amino acid sequence set forth in SEQ ID NO: 1.

6. The aqueous formulation according to claim 1, comprising about 100-200 mg/mL of the FcRn antagonist in 20 mM histidine/histidine HCl, 60 mM sucrose, 100 mM NaCl, 10 mM L-methionine, and 0.02%-0.04% (w/v) polysorbate 20 or polysorbate 80, pH 6.0.

7. The aqueous formulation according to claim 1, comprising about 165 mg/mL of the FcRn antagonist in 20 mM histidine/histidine HCl, 60 mM sucrose, 100 mM NaCl, 10 mM L-methionine, and 0.04% (w/v) polysorbate 20, pH 6.0.

8. The aqueous formulation according to claim 1, comprising 175 mg/mL of the FcRn antagonist in 20 mM histidine/histidine HCl, 60 mM sucrose, 100 mM NaCl, 10 mM L-methionine, and 0.03% (w/v) polysorbate 20, pH 6.0, wherein ARGX-113 is the isolated FcRn antagonist, wherein the amino acid sequence of each of the Fc domains consists of SEQ ID NO: 1.

9. The aqueous formulation according to claim 1, comprising 200 mg/mL ARGX-113 in 20 mM histidine/histidine HCl, 60 mM sucrose, 100 mM NaCl, 10 mM L-methionine, and 0.03% (w/v) polysorbate 20, pH 6.0, wherein the amino acid sequence of each of the Fc domains of the FcRn antagonist consists of the amino acid sequence set forth in SEQ ID NO: 1.

10. The aqueous formulation according to claim 1, comprising about 100-200 mg/mL of the FcRn antagonist in 50 mM histidine/histidine HCl, 60 mM sucrose, 150 mM arginine HCl, and 0.02%-0.04% (w/v) polysorbate 20 or polysorbate 80, pH 6.0.

11. The aqueous formulation according to claim 1, comprising about 100-200 mg/mL of the FcRn antagonist in 20 mM histidine/histidine HCl, 60 mM sucrose, 100 mM arginine HCl, 10 mM L-methionine, and 0.02%-0.04% (w/v) polysorbate 20 or polysorbate 80, pH 6.0.

12. An aqueous formulation comprising 175 mg/mL of an FcRn antagonist in 20 mM histidine/histidine HCl, 60 mM sucrose, 100 mM arginine HCl, 10 mM L-methionine, and 0.03% (w/v) polysorbate 20, pH 6.0, wherein the FcRn antagonist consists of a variant Fc region, and wherein the variant Fc region consists of two Fc domains which form a homodimer, wherein the amino acid sequence of each of the Fc domains consists of the amino acid sequence set forth in SEQ ID NO: 1.

13. The aqueous formulation according to claim 1, comprising 200 mg/mL of the FcRn antagonist in 20 mM histidine/histidine HCl, 60 mM sucrose, 100 mM arginine HCl, 10 mM L-methionine, and 0.03% (w/v) polysorbate 20, pH 6.0, wherein the amino acid sequence of each of the Fc domains of the FcRn antagonist consists of the amino acid sequence set forth in SEQ ID NO: 1.

14. The aqueous formulation according to claim 1, comprising about 100-300 mg/mL of the FcRn antagonist in 50 mM histidine/histidine HCl, 200 mM arginine HCl, pH 6.5.

15. A packaged pharmaceutical product comprising a sterile container comprising a therapeutically effective amount of the aqueous formulation of claim 1.

16. A device comprising a therapeutically effective amount of the aqueous formulation of claim 1.

17. The device according to claim 16, wherein the device comprises a syringe comprising the aqueous formulation.

18. A packaged pharmaceutical product comprising a sterile container comprising a therapeutically effective amount of the aqueous formulation of claim 12.

19. A device comprising a therapeutically effective amount of the aqueous formulation of claim 12.

20. The device according to claim 19, wherein the device comprises a syringe comprising the aqueous formulation.

21. An aqueous formulation comprising 100-200 mg/mL of an FcRn antagonist in 20 mM L-histidine/L-histidine HCl, 100 mM NaCl, 60 mM sucrose, 10 mM L-methionine, and 0.04% (w/v) polysorbate 20, pH 6.0-6.5, wherein the FcRn antagonist consists of a variant Fc region, and wherein the variant Fc region consists of two Fc domains which form a homodimer, wherein the amino acid sequence of each of the Fc domains consists of the amino acid sequence set forth in SEQ ID NO: 1.

* * * * *

UNITED STATES PATENT AND TRADEMARK OFFICE
CERTIFICATE OF CORRECTION

PATENT NO. : 11,591,388 B2
APPLICATION NO. : 16/893863
DATED : February 28, 2023
INVENTOR(S) : Filip Borgions et al.

It is certified that error appears in the above-identified patent and that said Letters Patent is hereby corrected as shown below:

In the Claims

Column 43, Lines 24-26, for Claim reference numeral "8" replace:
"wherein ARGX-113 is the isolated FcRn antagonist, wherein the amino acid sequence of each of the Fc domains consists of SEQ ID NO: 1."
With:
--wherein the amino acid sequence of each of the Fc domains of the FcRn antagonist consists of the amino acid sequence set forth in SEQ ID NO: 1.--

Column 43, Line 28, for Claim reference number "9" replace:
"200 mg/mL ARGX-113"
With:
--200 mg/mL of the FcRn antagonist--

Signed and Sealed this
Twenty-fifth Day of April, 2023

Katherine Kelly Vidal
*Director of the United States Patent and Trademark Office*

SEQUENCE LISTING

```
<160> NUMBER OF SEQ ID NOS: 3

<210> SEQ ID NO 1
<211> LENGTH: 226
<212> TYPE: PRT
<213> ORGANISM: Artificial sequence
<220> FEATURE:
<223> OTHER INFORMATION: Synthetic peptide

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
            85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                    165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
            195                 200                 205
His Glu Ala Leu Lys Phe His Tyr Thr Gln Lys Ser Leu Ser Leu Ser
            210                 215                 220
Pro Gly
225
```

<210> SEQ ID NO 2
<211> LENGTH: 227
<212> TYPE: PRT
<213> ORGANISM: Artificial sequence
<220> FEATURE:
<223> OTHER INFORMATION: Synthetic peptide

<400> SEQUENCE: 2

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Tyr
            20                  25                  30
Ile Thr Arg Glu Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
            85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                    165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
            195                 200                 205
```

```
His Glu Ala Leu Lys Phe His Tyr Thr Gln Lys Ser Leu Ser Leu Ser
    210                 215                 220

Pro Gly Lys
225

<210> SEQ ID NO 3
<211> LENGTH: 231
<212> TYPE: PRT
<213> ORGANISM: Artificial sequence
<220> FEATURE:
<223> OTHER INFORMATION: Synthetic peptide

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu Lys Phe His Tyr Thr Gln Lys Ser Leu Ser Leu Ser
    210                 215                 220

Pro Asp Ser Asn Leu Trp Asn
225                 230
```